(12) United States Patent
Netzel et al.

(10) Patent No.: US 12,011,560 B2
(45) Date of Patent: **\*Jun. 18, 2024**

(54) DRUG DELIVERY METHODS AND SYSTEMS

(71) Applicant: Morningside Venture Investments Limited, Monaco (MC)

(72) Inventors: Zita S. Netzel, Los Altos, CA (US); Gary Stacey, Cambridge (GB); Alexander David Norman, Trumpington (GB); Congyi Huang, Cambridge (GB); Timothy Charles Frearson, Hartley Wintney (GB); Charles Frazer Kilby, St. Neots (GB); Patrick H. Ruane, Dublin, CA (US); Alan J. Levy, Bellevue, WA (US); Kevin W. Gelston, Moraga, CA (US); Jennifer Darmour, Seattle, WA (US); Jenny E. Hapgood, Tacoma, WA (US); David Evans Roth, Issaquah, WA (US); Ronald A. Overbeck, Winthrop, WA (US); Ling-Kang Tong, Hayward, CA (US)

(73) Assignee: Morningside Venture Investments Limited, Monaco (MC)

(\*) Notice: Subject to any disclaimer, the term of this patent is extended or adjusted under 35 U.S.C. 154(b) by 0 days.

This patent is subject to a terminal disclaimer.

(21) Appl. No.: 17/815,879

(22) Filed: Jul. 28, 2022

(65) Prior Publication Data

US 2023/0191097 A1 Jun. 22, 2023

Related U.S. Application Data

(60) Continuation of application No. 16/284,933, filed on Feb. 25, 2019, now Pat. No. 11,400,266, which is a
(Continued)

(51) Int. Cl.
*A61M 35/00* (2006.01)
*A61M 5/142* (2006.01)
(Continued)

(52) U.S. Cl.
CPC ........ *A61M 35/00* (2013.01); *A61M 5/14244* (2013.01); *A61M 5/14248* (2013.01);
(Continued)

(58) Field of Classification Search
CPC .............. A61M 35/00; A61M 5/14244; A61M 5/14248; A61M 5/145; A61M 5/1456;
(Continued)

(56) References Cited

U.S. PATENT DOCUMENTS

| | | | |
|---|---|---|---|
| 2,183,482 | A | 12/1939 | Kurkjian |
| 3,279,653 | A | 10/1966 | Pfleger |

(Continued)

FOREIGN PATENT DOCUMENTS

| | | |
|---|---|---|
| AU | 662877 B3 | 9/1995 |
| BE | 899037 A | 6/1984 |

(Continued)

OTHER PUBLICATIONS

Dipierro et al.; U.S. Appl. No. 17/936,750 entitled "Optimized bio-synchronous bioactive agent delivery system," filed Sep. 29, 2022.
(Continued)

*Primary Examiner* — Dung T Ulsh
(74) *Attorney, Agent, or Firm* — Shay Glenn LLP

(57) ABSTRACT

A two-part bioactive agent delivery system, the system including a disposable part comprising an agent reservoir, a bolus chamber, the volume of the bolus chamber being less than the volume of the agent reservoir, an agent outlet, and a valve having a first position communicating the agent reservoir with the bolus chamber and a second position
(Continued)

communicating the bolus chamber with the outlet; and a reusable part including a valve driver, a power source and control electronics, the control electronics being adapted to control the valve driver to actuate the valve to deliver bioactive agent from the agent reservoir to the agent outlet; the system further having a spring extending between the agent reservoir piston and a surface of the reusable part or of the disposable part to pressurize the agent reservoir when the spring is compressed and the agent reservoir contains a quantity of bioactive agent.

1 Claim, 50 Drawing Sheets

Related U.S. Application Data continuation of application No. 15/699,382, filed on Sep. 8, 2017, now Pat. No. 10,232,156, which is a division of application No. 15/009,683, filed on Jan. 28, 2016, now Pat. No. 10,213,586.

(60) Provisional application No. 62/263,516, filed on Dec. 4, 2015, provisional application No. 62/132,436, filed on Mar. 12, 2015, provisional application No. 62/108,959, filed on Jan. 28, 2015.

(51) Int. Cl.
*A61M 5/145* (2006.01)
*A61M 5/168* (2006.01)

(52) U.S. Cl.
CPC .......... *A61M 5/145* (2013.01); *A61M 5/1456* (2013.01); *A61M 5/16877* (2013.01); *A61M 5/16881* (2013.01); *A61M 2005/14268* (2013.01); *A61M 2005/14506* (2013.01); *A61M 2005/14573* (2013.01)

(58) Field of Classification Search
CPC .......... A61M 5/16877; A61M 5/16881; A61M 2005/14506; A61M 2005/14268; A61M 2005/14573
See application file for complete search history.

(56) References Cited

U.S. PATENT DOCUMENTS 3,845,217 A 10/1974 Ferno et al.
4,313,439 A 2/1982 Babb et al.
4,321,387 A 3/1982 Chavdarian et al.
4,327,725 A 5/1982 Cortese et al.
4,332,945 A 6/1982 Edwards
4,379,454 A 4/1983 Campbell et al.
4,545,990 A 10/1985 Le Foyer de Costil et al.
4,579,858 A 4/1986 Femo et al.
4,590,278 A 5/1986 Edwards
4,597,961 A 7/1986 Etscorn
4,708,716 A 11/1987 Sibalis
4,772,263 A 9/1988 Dorman et al.
4,806,356 A 2/1989 Shaw
4,853,854 A 8/1989 Behar et al.
4,885,154 A 12/1989 Cormier et al.
4,908,213 A 3/1990 Govil et al.
4,917,676 A 4/1990 Heiber et al.
4,917,895 A 4/1990 Lee et al.
4,920,989 A 5/1990 Rose et al.
4,952,928 A 8/1990 Carroll et al.
4,953,572 A 9/1990 Rose et al.
4,992,445 A 2/1991 Lawter et al.
4,994,278 A 2/1991 Sablotsky et al.
5,000,956 A 3/1991 Amkraut et al.
5,001,139 A 3/1991 Lawter et al.
5,013,293 A 5/1991 Sibalis
5,023,252 A 6/1991 Hseih
5,049,387 A 9/1991 Amkraut
5,069,904 A 12/1991 Masterson
5,073,380 A 12/1991 Babu et al.
5,097,834 A 3/1992 Skrabal
5,120,545 A 6/1992 Ledger et al.
5,130,139 A 7/1992 Cormier et al.
5,149,538 A 9/1992 Granger et al.
5,149,719 A 9/1992 Ferber et al.
5,212,188 A 5/1993 Caldwell et al.
5,221,254 A 6/1993 Phipps
5,227,391 A 7/1993 Caldwell et al.
5,232,704 A 8/1993 Franz et al.
5,232,933 A 8/1993 Lippiello et al.
5,236,714 A 8/1993 Lee et al.
5,242,934 A 9/1993 Lippiello et al.
5,242,935 A 9/1993 Lippiello et al.
5,242,941 A 9/1993 Lewy et al.
5,248,690 A 9/1993 Caldwel et al.
5,252,604 A 10/1993 Nagy et al.
5,262,165 A 11/1993 Govil et al.
5,273,755 A 12/1993 Venkatraman et al.
5,273,756 A 12/1993 Fallon et al.
5,304,739 A 4/1994 Klug et al.
5,310,404 A 5/1994 Gyory et al.
5,352,456 A 10/1994 Fallon et al.
5,364,630 A 11/1994 Osborne et al.
5,370,635 A 12/1994 Strausak et al.
5,388,571 A 2/1995 Roberts et al.
5,389,679 A 2/1995 Alliger
5,393,526 A 2/1995 Castro
5,405,614 A 4/1995 D'Angelo et al.
5,415,629 A 5/1995 Henley
5,445,609 A 8/1995 Lattin et al.
5,451,407 A 9/1995 Cormier et al.
5,464,387 A 11/1995 Haak et al.
5,472,946 A 12/1995 Peck et al.
5,501,697 A 3/1996 Fisher
5,505,958 A 4/1996 Bello et al.
5,512,306 A 4/1996 Carlsson et al.
5,516,793 A 5/1996 Duffy
5,525,351 A 6/1996 Dam
5,545,407 A 8/1996 Hall et al.
5,562,607 A 10/1996 Gyory
5,596,994 A 1/1997 Bro
5,601,839 A 2/1997 Quan et al.
5,616,332 A 4/1997 Herstein
5,618,557 A 4/1997 Wille et al.
5,653,682 A 8/1997 Sibalis
5,656,255 A 8/1997 Jones
5,662,920 A 9/1997 Santus
5,686,100 A 11/1997 Wille et al.
5,688,232 A 11/1997 Flower
5,697,896 A 12/1997 McNichols et al.
5,716,987 A 2/1998 Wille
5,722,418 A 3/1998 Bro
5,733,259 A 3/1998 Valcke et al.
5,785,688 A 7/1998 Joshi et al.
5,797,867 A 8/1998 Guerrera et al.
5,820,875 A 10/1998 Fallon et al.
5,833,466 A 11/1998 Borg
5,843,979 A 12/1998 Wille et al.
5,846,559 A 12/1998 Hopp
5,865,786 A 2/1999 Sibalis et al.
5,876,368 A 3/1999 Flower
5,879,292 A 3/1999 Sternberg et al.
5,879,322 A 3/1999 Lattin et al.
5,882,676 A 3/1999 Lee et al.
5,908,301 A 6/1999 Lutz
5,919,156 A 7/1999 Stropkay et al.
5,932,240 A 8/1999 D'Angelo et al.
5,945,123 A 8/1999 Hermelin
5,967,789 A 10/1999 Segel et al.
5,972,389 A 10/1999 Shell et al.
5,993,435 A 11/1999 Haak et al.
5,997,501 A 12/1999 Gross et al.
6,018,679 A 1/2000 Dinh et al.
6,019,997 A 2/2000 Scholz et al.

(56) References Cited

U.S. PATENT DOCUMENTS

| | | | |
|---|---|---|---|
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Wolas et al. |
| 6,162,214 A | 12/2000 | Mueller et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,221,394 B1 | 4/2001 | Gilbert et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,488,959 B2 | 12/2002 | Stanley et al. |
| 6,492,399 B1 | 12/2002 | Dull et al. |
| 6,539,250 B1 | 3/2003 | Bettinger |
| 6,546,281 B1 | 4/2003 | Zhang et al. |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,011,849 B2 | 3/2006 | Storm et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,931,563 B2 | 4/2011 | Shaw et al. |
| 7,988,660 B2 | 8/2011 | Byland et al. |
| 8,003,080 B2 | 8/2011 | Rabinowitz et al. |
| 8,021,334 B2 | 9/2011 | Shekalim |
| 8,137,314 B2 | 3/2012 | Mounce et al. |
| 8,140,143 B2 | 3/2012 | Picard et al. |
| 8,192,756 B2 | 6/2012 | Berner et al. |
| 8,246,581 B2 | 8/2012 | Adams et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,285,328 B2 | 10/2012 | Caffey et al. |
| 8,303,500 B2 | 11/2012 | Raheman |
| 8,309,568 B2 | 11/2012 | Stinchcomb et al. |
| 8,372,040 B2 | 2/2013 | Huang et al. |
| 8,414,532 B2 | 4/2013 | Brandt et al. |
| 8,440,220 B2 | 5/2013 | Gale et al. |
| 8,440,221 B2 | 5/2013 | Zumbrunn et al. |
| 8,441,411 B2 | 5/2013 | Tucholski et al. |
| 8,445,010 B2 | 5/2013 | Anderson et al. |
| 8,449,471 B2 | 5/2013 | Tran |
| 8,517,988 B2 | 8/2013 | Smith |
| 8,545,445 B2 | 10/2013 | Kamen et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,614,278 B2 | 12/2013 | Loubert et al. |
| 8,632,497 B2 | 1/2014 | Yodfat et al. |
| 8,666,781 B2 | 3/2014 | Hanina et al. |
| 8,673,346 B2 | 3/2014 | Zumbrunn et al. |
| 8,684,922 B2 | 4/2014 | Tran |
| 8,688,189 B2 | 4/2014 | Shennib |
| 8,690,827 B2 | 4/2014 | Edwards et al. |
| 8,690,865 B2 | 4/2014 | Prausnitz et al. |
| 8,696,637 B2 | 4/2014 | Ross |
| 8,703,175 B2 | 4/2014 | Kanios et al. |
| 8,703,177 B2 | 4/2014 | Finn et al. |
| 8,722,233 B2 | 5/2014 | Tucholski |
| 8,727,745 B2 | 5/2014 | Rush et al. |
| 8,741,336 B2 | 6/2014 | DiPierro et al. |
| 8,747,348 B2 | 6/2014 | Yodfat et al. |
| 8,753,315 B2 | 6/2014 | Alferness et al. |
| 8,773,257 B2 | 7/2014 | Yodfat et al. |
| 8,814,822 B2 | 8/2014 | Yodfat et al. |
| 8,862,223 B2 | 10/2014 | Yanaki |
| 8,864,727 B2 | 10/2014 | Lee |
| 8,865,207 B2 | 10/2014 | Kanios et al. |
| 8,872,663 B2 | 10/2014 | Forster |
| 8,876,802 B2 | 11/2014 | Grigorov |
| 8,956,644 B2 | 2/2015 | Yum et al. |
| 8,962,014 B2 | 2/2015 | Prinz et al. |
| 8,986,253 B2 | 3/2015 | DiPerna |
| 8,999,356 B1 | 4/2015 | Ramirez et al. |
| 8,999,372 B2 | 4/2015 | Davidson et al. |
| 9,023,392 B2 | 5/2015 | Koo et al. |
| 9,044,582 B2 | 6/2015 | Chang et al. |
| 9,050,348 B2 | 6/2015 | Kydonieus et al. |
| 9,078,833 B2 | 7/2015 | Audett |
| 9,111,085 B1 | 8/2015 | Darmour et al. |
| 9,114,240 B2 | 8/2015 | Horstmann et al. |
| 9,155,712 B2 | 10/2015 | Kanios et al. |
| 9,233,203 B2 | 1/2016 | Moberg et al. |
| 9,238,001 B2 | 1/2016 | Weyer et al. |
| 9,238,108 B2 | 1/2016 | Edwards et al. |
| 9,248,104 B2 | 2/2016 | Valia et al. |
| 9,289,397 B2 | 3/2016 | Wright |
| 9,308,202 B2 | 4/2016 | Hille et al. |
| 9,314,527 B2 | 4/2016 | Cottrell et al. |
| 9,373,269 B2 | 6/2016 | Bergman et al. |
| 9,380,698 B1 | 6/2016 | Li et al. |
| RE46,217 E | 11/2016 | Huang et al. |
| 9,513,666 B2 | 12/2016 | Li et al. |
| 9,549,903 B2 | 1/2017 | Hille et al. |
| 9,555,226 B2 | 1/2017 | Zumbrunn et al. |
| 9,555,227 B2 | 1/2017 | Dipierro |
| 9,555,277 B2 | 1/2017 | Yeh |
| 9,623,017 B2 | 4/2017 | Barbier et al. |
| 9,636,457 B2 | 5/2017 | Newberry et al. |
| 9,655,843 B2 | 5/2017 | Finn et al. |
| 9,656,441 B2 | 5/2017 | LeDonne et al. |
| 9,669,199 B2 | 6/2017 | DiPierro et al. |
| 9,687,186 B2 | 6/2017 | Goldstein et al. |
| 9,693,689 B2 | 7/2017 | Gannon et al. |

(56) References Cited

U.S. PATENT DOCUMENTS

| | | | |
|---|---|---|---|
| 9,700,552 B2 | 7/2017 | Weimann |
| 9,717,698 B2 | 8/2017 | Horstmann et al. |
| 9,782,082 B2 | 10/2017 | Gannon et al. |
| 9,795,681 B2 | 10/2017 | Abreu |
| 9,867,539 B2 | 1/2018 | Heikenfeld et al. |
| 9,895,320 B2 | 2/2018 | Ogino et al. |
| 9,949,935 B2 | 4/2018 | Murata |
| 9,974,492 B1 | 5/2018 | Dicks et al. |
| 9,993,203 B2 | 6/2018 | Mei et al. |
| 10,004,447 B2 | 6/2018 | Shen et al. |
| 10,034,841 B2 | 7/2018 | Müller et al. |
| 10,105,487 B2 | 10/2018 | Dipierro et al. |
| 10,213,586 B2 | 2/2019 | Netzel et al. |
| 10,232,156 B2 | 3/2019 | Netzel et al. |
| 10,258,738 B2 | 4/2019 | Dipierro et al. |
| 10,258,778 B2 | 4/2019 | DiPierro et al. |
| 10,679,516 B2 | 6/2020 | Darmour et al. |
| 10,716,764 B2 | 7/2020 | Zumbrunn et al. |
| 11,285,306 B2 | 3/2022 | Johnson et al. |
| 11,400,266 B2 | 8/2022 | Netzel et al. |
| 11,471,424 B2 | 10/2022 | Dipierro |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0034535 A1 | 3/2002 | Kleiner et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Creton |
| 2003/0004187 A1 | 1/2003 | Bedard et al. |
| 2003/0065294 A1 | 4/2003 | Pickup et al. |
| 2003/0065924 A1 | 4/2003 | Wuldart et al. |
| 2003/0083645 A1 | 5/2003 | Angel et al. |
| 2003/0087937 A1 | 5/2003 | Lindberg |
| 2003/0119879 A1 | 6/2003 | Landh et al. |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0219192 A1 | 11/2004 | Horstmann et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2005/0197625 A1 | 9/2005 | Haueter et al. |
| 2005/0266032 A1 | 12/2005 | Srinivasan et al. |
| 2005/0276852 A1 | 12/2005 | Davis et al. |
| 2006/0024358 A1 | 2/2006 | Santini et al. |
| 2006/0036209 A1 | 2/2006 | Subramony et al. |
| 2006/0057202 A1 | 3/2006 | Antarkar et al. |
| 2006/0122577 A1 | 6/2006 | Poulsen et al. |
| 2006/0135911 A1 | 6/2006 | Mittur |
| 2006/0167039 A1 | 7/2006 | Nguyen et al. |
| 2006/0184093 A1 | 8/2006 | Phipps et al. |
| 2006/0188859 A1 | 8/2006 | Yakobi |
| 2006/0204578 A1 | 9/2006 | Vergez et al. |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0104787 A1 | 5/2007 | Posey Dowty et al. |
| 2007/0149952 A1 | 6/2007 | Bland et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |
| 2007/0191815 A1 | 8/2007 | DiPierro |
| 2007/0250018 A1 | 10/2007 | Adachi et al. |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alferness et al. |
| 2008/0008747 A1 | 1/2008 | Royds |
| 2008/0015494 A1 | 1/2008 | Santini et al. |
| 2008/0131494 A1 | 6/2008 | Reed et al. |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0139907 A1 | 6/2008 | Rao et al. |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0233178 A1 | 9/2008 | Reidenberg et al. |
| 2008/0274168 A1 | 11/2008 | Baker et al. |
| 2008/0319272 A1 | 12/2008 | Patangay et al. |
| 2009/0005009 A1 | 1/2009 | Marsili |
| 2009/0010998 A1 | 1/2009 | Marchitto et al. |
| 2009/0024004 A1 | 1/2009 | Yang |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2009/0299156 A1 | 12/2009 | Simpson et al. |
| 2010/0003653 A1 | 1/2010 | Brown |
| 2010/0010443 A1 | 1/2010 | Morgan et al. |
| 2010/0068250 A1 | 3/2010 | Anderson et al. |
| 2010/0114008 A1 | 5/2010 | Marchitto et al. |
| 2010/0130932 A1* | 5/2010 | Yodfat .............. A61M 5/14248 604/151 |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0198187 A1 | 8/2010 | Yodfat et al. |
| 2010/0211005 A1 | 8/2010 | Edwards et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1 | 1/2011 | Fletcher et al. |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0160655 A1 | 6/2011 | Hanson et al. |
| 2011/0212027 A1 | 9/2011 | Hoare et al. |
| 2011/0241446 A1 | 10/2011 | Tucholski |
| 2011/0245633 A1 | 10/2011 | Goldberg et al. |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 | 11/2011 | Brinkley et al. |
| 2011/0275987 A1 | 11/2011 | Caffey et al. |
| 2012/0046644 A1 | 2/2012 | Ziale et al. |
| 2012/0078216 A1 | 3/2012 | Smith et al. |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0191043 A1 | 7/2012 | Yodfat et al. |
| 2012/0203573 A1 | 8/2012 | Mayer et al. |

(56) References Cited

U.S. PATENT DOCUMENTS

| | | |
|---|---|---|
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |
| 2012/0316896 A1 | 12/2012 | Rahman et al. |
| 2012/0329017 A1 | 12/2012 | Pham |
| 2013/0017259 A1 | 1/2013 | Azhil |
| 2013/0041258 A1 | 2/2013 | Patrick et al. |
| 2013/0096495 A1 | 4/2013 | Holmqvist et al. |
| 2013/0123719 A1 | 5/2013 | Mao et al. |
| 2013/0158430 A1 | 6/2013 | Aceti et al. |
| 2013/0178826 A1 | 7/2013 | Li |
| 2013/0190683 A1 | 7/2013 | Hanson et al. |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-Or et al. |
| 2013/0317384 A1 | 11/2013 | Le |
| 2013/0328572 A1 | 12/2013 | Wang et al. |
| 2013/0345633 A1 | 12/2013 | Hong |
| 2014/0046288 A1 | 2/2014 | Geipel et al. |
| 2014/0073883 A1 | 3/2014 | Rao et al. |
| 2014/0088554 A1 | 3/2014 | Li et al. |
| 2014/0099614 A1 | 4/2014 | Hu et al. |
| 2014/0100241 A1 | 4/2014 | Slater et al. |
| 2014/0163521 A1 | 6/2014 | O'Conner |
| 2014/0200525 A1 | 7/2014 | DiPierro |
| 2014/0206327 A1 | 7/2014 | Ziemianska et al. |
| 2014/0207047 A1 | 7/2014 | DiPierro et al. |
| 2014/0228736 A1 | 8/2014 | Eppstein et al. |
| 2014/0237028 A1 | 8/2014 | Messenger et al. |
| 2014/0240124 A1 | 8/2014 | Bychkov |
| 2014/0266584 A1 | 9/2014 | Ingle et al. |
| 2014/0272844 A1 | 9/2014 | Hendriks et al. |
| 2014/0272845 A1 | 9/2014 | Hendriks et al. |
| 2014/0272846 A1 | 9/2014 | Richling |
| 2014/0275135 A1 | 9/2014 | Genov et al. |
| 2014/0275932 A1 | 9/2014 | Zadig |
| 2014/0276127 A1 | 9/2014 | Ferdosi et al. |
| 2014/0279740 A1 | 9/2014 | Wernevi et al. |
| 2014/0302121 A1 | 10/2014 | Bevier |
| 2014/0303574 A1 | 10/2014 | Knutson |
| 2014/0365408 A1 | 12/2014 | Snyder et al. |
| 2014/0378943 A1 | 12/2014 | Geipel |
| 2015/0057616 A1* | 2/2015 | Shergold ............ A61M 5/31593 604/152 |
| 2015/0209783 A1 | 7/2015 | Ingber et al. |
| 2015/0273148 A1 | 10/2015 | Sexton et al. |
| 2015/0310760 A1 | 10/2015 | Knotts et al. |
| 2015/0322939 A1 | 11/2015 | Katase |
| 2015/0342900 A1 | 12/2015 | Putnins |
| 2016/0030412 A1 | 2/2016 | Azhir |
| 2016/0058939 A1* | 3/2016 | Brewer ............ A61M 5/31515 604/500 |
| 2016/0220553 A1 | 8/2016 | Azhir |
| 2016/0227361 A1 | 8/2016 | Booth et al. |
| 2016/0228383 A1 | 8/2016 | Zhang et al. |
| 2016/0235732 A1 | 8/2016 | Quik et al. |
| 2016/0235916 A1 | 8/2016 | Edwards et al. |
| 2016/0263312 A1 | 9/2016 | Junod et al. |
| 2016/0310664 A1 | 10/2016 | McKenzie et al. |
| 2016/0317057 A1 | 11/2016 | Li et al. |
| 2016/0317738 A1 | 11/2016 | Cross et al. |
| 2016/0339174 A1 | 11/2016 | Shapley et al. |
| 2016/0346462 A1 | 12/2016 | Adams et al. |
| 2017/0007550 A1 | 1/2017 | Enscore et al. |
| 2017/0079932 A1 | 3/2017 | Emgenbroich et al. |
| 2017/0100573 A1 | 4/2017 | DiPierro |
| 2017/0189348 A1 | 7/2017 | Lee et al. |
| 2017/0189534 A1 | 7/2017 | Lee et al. |
| 2017/0207825 A1 | 7/2017 | Belogolovy |
| 2017/0209429 A1 | 7/2017 | Stinchcomb et al. |
| 2017/0232192 A1 | 8/2017 | Sasaki |
| 2017/0249433 A1 | 8/2017 | Hagen et al. |
| 2017/0296317 A1 | 10/2017 | Gordon |
| 2017/0351840 A1 | 12/2017 | Goguen |
| 2018/0110768 A1 | 4/2018 | Quik et al. |
| 2018/0110975 A1 | 4/2018 | Ivanoff et al. |
| 2018/0165566 A1 | 6/2018 | Rogers et al. |
| 2018/0197637 A1 | 7/2018 | Chowdhury |
| 2018/0374381 A1 | 12/2018 | Darmour et al. |
| 2019/0054078 A1 | 2/2019 | Azhir et al. |
| 2019/0054235 A1 | 2/2019 | DiPierro et al. |
| 2019/0231707 A1 | 8/2019 | Stiles et al. |
| 2019/0374482 A1 | 12/2019 | Schaller et al. |
| 2020/0030590 A1 | 1/2020 | Buchman et al. |
| 2020/0368175 A1 | 11/2020 | Arora et al. |
| 2021/0169822 A1 | 6/2021 | Zumbrunn et al. |
| 2021/0196935 A1 | 7/2021 | Tong et al. |
| 2022/0001158 A1 | 1/2022 | Ruane et al. |
| 2022/0280763 A1 | 9/2022 | Johnston et al. |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 311313 A2 | 4/1989 |
| EP | 0314528 B1 | 12/1992 |
| EP | 0354554 B1 | 1/1994 |
| EP | 0726005 A1 | 8/1996 |
| EP | 857725 A1 | 8/1998 |
| EP | 870768 A1 | 10/1998 |
| EP | 955301 A2 | 11/1999 |
| EP | 0612525 B1 | 9/2001 |
| EP | 1815784 A1 | 8/2007 |
| EP | 1977746 B1 | 7/2014 |
| EP | 1662989 B1 | 9/2014 |
| EP | 3016586 A2 | 5/2016 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | H09504974 A | 5/1997 |
| JP | 09512006 A | 12/1997 |
| JP | 2000515394 A | 11/2000 |
| JP | 2001505491 A | 4/2001 |
| JP | 2002092180 A | 3/2002 |
| JP | 2003506477 A | 2/2003 |
| JP | 2005521526 A | 7/2005 |
| JP | 2005525147 A | 8/2005 |
| JP | 2007509661 A | 4/2007 |
| JP | 2008523918 A | 7/2008 |
| JP | 2009544338 A | 12/2009 |
| JP | 2010518914 A | 6/2010 |
| JP | 2010279808 A | 12/2010 |
| JP | 2011036491 A | 2/2011 |
| JP | 2013524951 A | 6/2013 |
| JP | 2015070868 A | 4/2015 |
| JP | 2016202904 A | 12/2016 |
| WO | WO86/07269 A1 | 12/1986 |
| WO | WO88/003803 A1 | 6/1988 |
| WO | WO91/14441 A1 | 10/1991 |
| WO | WO92/021339 A1 | 12/1992 |
| WO | WO94/008992 A1 | 4/1994 |
| WO | WO94/010987 A1 | 5/1994 |
| WO | WO95/06497 A1 | 3/1995 |
| WO | WO96/015123 A1 | 5/1996 |
| WO | WO96/040682 A1 | 12/1996 |
| WO | WO97/011072 A1 | 3/1997 |
| WO | WO97/011073 A1 | 3/1997 |
| WO | WO97/11741 A1 | 4/1997 |
| WO | WO97/18782 A1 | 5/1997 |
| WO | WO97/019059 A1 | 5/1997 |
| WO | WO97/028801 A1 | 8/1997 |
| WO | WO97/034605 A1 | 9/1997 |
| WO | WO97/042941 A2 | 11/1997 |
| WO | WO97/046554 A1 | 12/1997 |
| WO | WO98/042713 A1 | 10/1998 |
| WO | WO98/46093 A1 | 10/1998 |
| WO | WO98/054152 A1 | 12/1998 |

(56) References Cited

FOREIGN PATENT DOCUMENTS

| | | |
|---|---|---|
| WO | WO98/054181 A1 | 12/1998 |
| WO | WO98/054182 A1 | 12/1998 |
| WO | WO98/054189 A1 | 12/1998 |
| WO | WO98/55107 A1 | 12/1998 |
| WO | WO99/002517 A1 | 1/1999 |
| WO | WO99/003859 A1 | 1/1999 |
| WO | WO99/021834 A1 | 5/1999 |
| WO | WO99/024422 A1 | 5/1999 |
| WO | WO99/066916 A1 | 12/1999 |
| WO | WO00/010997 A1 | 3/2000 |
| WO | WO00/032600 A1 | 6/2000 |
| WO | WO00/034279 A1 | 6/2000 |
| WO | WO00/034284 A1 | 6/2000 |
| WO | WO00/035279 A1 | 6/2000 |
| WO | WO00/035456 A1 | 6/2000 |
| WO | WO00/044755 A1 | 8/2000 |
| WO | WO00/064885 A1 | 11/2000 |
| WO | WO00/066596 A1 | 11/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/041544 A1 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/122049 A2 | 10/2008 |
| WO | WO2008/135283 A1 | 11/2008 |
| WO | WO2009/136304 A2 | 11/2009 |
| WO | WO2011/088072 A2 | 7/2011 |
| WO | WO2012/012846 A1 | 2/2012 |
| WO | WO2012/101060 A1 | 8/2012 |
| WO | WO2013/093666 A1 | 6/2013 |
| WO | WO2013/168068 A1 | 11/2013 |
| WO | WO2014/001877 A1 | 1/2014 |
| WO | WO2014/043502 A1 | 3/2014 |
| WO | WO2016/081616 A2 | 5/2016 |
| WO | WO2016/132368 A1 | 8/2016 |
| WO | WO2016/161416 A1 | 10/2016 |
| WO | WO2017/053938 A1 | 3/2017 |
| WO | WO2017/125455 A1 | 7/2017 |
| WO | WO2018/026759 A1 | 2/2018 |

OTHER PUBLICATIONS

Abood et al.; Structure-activity studies of carbamate and other esters: agonists and antagonists to nicotine; Pharmacology Biochemistry and Behavior; 30(2); pp. 403-408; Jun. 1988.

Ahlskog et al.; Frequency of levodopa-related dyskinesias and motor fluctuations as estimated from the cumulative literature; Movement Disorders; 16(3); pp. 448-458; May 1, 2001.

Angulo et al.; Oral nicotine in treatment of primary sclerosing cholangitis: a pilot study; Digestive diseases and sciences; 44(3); pp. 602-607; Mar. 1, 1999.

Baldessarini et al.; Preclinical studies of the pharmacology of aporphines; in: Gessa GL, Corsini GU, eds.; Apomorphine and other dopaminomi-'metics vol. 1, Basic pharmacology; New York: Raven Press; pp. 219-228; (the year of publication is sufficiently earlier than the effective U.S. filing date and any foreign priority date so that the particular month of publication is not in issue) 1981.

Balfour et al.; Pharmacology of nicotine and its therapeutic use in smoking cessation and neurodegenerative disorders; Pharmacology and Therapeutics; 72(1); pp. 51-81; Jan. 1, 1996.

Benowitz et al.; Sources of variability in nicotine and cotinine levels with use of nicotine nasal spray, transdermal nicotine, and cigarette smoking; British Journal of Clinical Pharmacology: 43(3); pp. 259-267; Mar. 1, 1997.

Benowitz et al.; Stable isotope studies of nicotine kinetics and bioavailability; Clin Pharm and Ther; 49(3); pp. 270-277; Mar. 1991.

Bordia et al.; Continuous and intermittent nicotine treatment reduces L-3 4-dihydroxyphenyalanine (L-DOPA)-induced dyskinesias in rat model of Parkinson's diseases; Journal of Pharmacology ans Experimental Therapeutics; 327(1); pp. 239-247; Oct. 1, 2008.

Bordia et al.; Partial recovery of striatal nicotinic receptors in l-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.

Bove et al.; Toxin-induced models of Parkinson's disease; NeuroRx; 2(3); pp. 484-494; Jul. 31, 2005.

Bricker et al.; Randomized controlled pilot trial of a smartphone app for smoking cessation using acceptance and commitment therapy; Drug and Alcohol Dependence; 143; pp. 87-94; Oct. 1, 2014 (Author Manuscript).

Brotchie et al.; Levodopa-induced dyskinesia in Parkinson's disease; Journal of Neural Transmission; 112(3); pp. 359-391; Mar. 1, 2005.

Bruguerolle; Chronopharmacokinetics; Clin Pharmacokinet; 35(2); pp. 83-94; Aug. 1998.

Calabresi et al.; Levodopa-induced dyskinesias inpatients with parkinson's disease: filling the bench-to-bedside gap; The Lancet Neurology; 9(11); pp. 1106-1117; Nov. 1, 2010.

Carta et al.; Role of striatal L-DOPA in the production of dyskinesia in 6-hydroxydopamine lesioned rats; Journal of Neurochemistry; 96(6); pp. 1718-1727; Mar. 2006.

Chen et al.; Enhanced striatal opioid receptor-mediated G-protein activation in L-DOPA-treated dyskinetic monkeys; Neuroscience; 132(2); pp. 409-420; Dec. 31, 2005.

Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.

Davie; A review of Parkinson's disease. British Medical Bulletin 2008 86 (1): 109-127; Apr. 8, 2008.

De La Fuente et al.; The placebo effect in Parkinson's disease; Trends in Neuroscience; 25(6); pp. 302-306; Jun. 1, 2002.

Di Monte et al.; Relationship among nigrostriatal denervation, parkinsonism, and dyskinesias in the MPTP primate model; Movement Disorders; 15(3); pp. 459-466; May 1, 2000.

Dockser-Marcus, A.; New research shows drugs work best at certain times; The Wall Street Journal; 6 pgs.; May 27, 2003; (http://www.wsj.com/articles/SB105397312486508700).

Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.

Dutil; Benzoyl Peroxide: Enhancing antibiotic efficacy in acne management; Skin Therapy Letter; 15(1); pp. 5-7; Nov./Dec. 2010.

Ebersbach et al.; Worsening of motor performance in patients with Parkinson's disease following transdermal nicotine administration; Movement Disorders; 14(6); pp. 1011-1013; Nov. 1, 1999.

Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.

Fagerstrom et al.; Nicotine may relieve symptoms of Parkinson's disease; Psychopharmacology; 116(1); pp. 117-119; Sep. 16, 1994.

Food and Drug Administration; Guidance for Industry—Dissolution Testing of Immediate Release Solid Oral Dosage Forms; 17 pages;

(56) References Cited

OTHER PUBLICATIONS retrieved from the internet (https://www.fda.gov/downloads/drugs/guidances/ucm070237.pdf); Aug. 1997.
Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.
Gennaro (Editor); Remington: The Science and Practice of Pharmacy; 19th Ed.; Mack Publishing Co.; Easton, PA; p. 1582-1584; Jun. 1995.
Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.
Gora; Nicotine transdermal systems; The Annals of Pharmacotherapy; 27(6); pp. 742-750; Jun. 1993.
Gotti et al.; Brain nicotinic acetylcholine receptors: native subtypes and their relevance; Treands in Pharmacological Sciences; 27(9); pp. 482-491; Sep. 30, 2006.
Green et al.; An oral formulation of nicotine for release and absorption in the colon: its development and pharmacokinetics. British Journal of Clinical Pharmacology; 48(4); pp. 485-493; Oct. 1999.
Gries et al.; Importance of Chronopharmacokinetics in Design and Evaluation of Transdermal Drug Delivery Systems; J Pharmoacol Exp Ther; 285(2); pp. 457-463; May 1998.
Guy; Current status and future prospects of transdermal drug delivery; Pharm Res; 13(12); pp. 1765-1769; Dec. 1996.
Halberg et al.; Chronomics: circadian and circaseptan timing of radiotherapy, drugs, calories, perhaps nutriceuticals and beyond; Journal of Experimental Therapeutics and Oncology; 3(5): pp. 223-260; Sep. 2003.
He et al.; Autoradiographic analysis of dopamine receptor-stimulated [35S]GTPtS binding in rat striatum; Brain Research; 885(1); pp. 133-136; Dec. 1, 2000.
He et al; Autoradiographic analysis of N-methyl-D-aspartate receptor binding in monkey brain: Effects of 1-methyl-4-phenyl-1,2,3,6-tetrahydropyridine andlevodopa treatment; Neuroscience; 99(4); pp. 697-704; Aug. 23, 2000.
Heffner et al.; Feature-level analysis of a novel smartphone applicationn for smoking cessation; Am. J. Drug Alcohol Abuse; 41(1); pp. 68-73; Jan. 2015 (Author Manuscript).
Hrushesky; Temporally optimizable delivery systems: sine qua non for the next therapeutic revolution; J Cont Rel; 19(1-3); pp. 363-368; Mar. 1992.
Hsu et al.; Effect of the D3 dopamine receptor partial agonist BP897 [N-[4-(4-(2-methoxyphenyl)piperaziny!)butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.
Huang et al.; Inhibitory effects of curcumin on in vitro lipoxygenase and cyclooxygenase activities in mouse epidermis; Cancer Res; 51(3); pp. 813-819; Feb. 1991.
Hukkanen et al.; Metabolism and disposition kinetics of nicotine; Pharmacological Reviews; 57(1); pp. 79-115; Mar. 1, 2005.
Hurley; Growing list of positive effects of nicotine seen in neurodegenerative disorders; Neurology Today; 12(2); pp. 37-38; Jan. 19, 2012.
Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.
Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.
Jarvik et al.; Inhibition of cigarette smoking by orally administered nicotine; Clinical Pharmacology and Therapeutics; 11(4); pp. 574-576; Jul. 1, 1970.
Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.
Jeyarasasingam et al.; Stimulation of non-o7 nicotinic receptors partially protects dopaminergic neurons from 1-methyl-4-phenylpyridinium-induced toxicity in culture; Neuroscience; 109(2); pp. 275-285; Jan. 28, 2002.
Jeyarasasingam et al.; Tacrine, a reversible acetylcholinesterase inhibitor, induces myopathy; Neuroreport; 11(6); pp. 1173-1176; Apr. 27, 2000.
Kalish et al.; Prevention of contact hypersensitivity to topically applied drugs by ethacrynic acid: potential application to transdermal drug delivery; J. Controll Rel; 48(1); pp. 79-87; Sep. 1997.
Kalish et al.; Sensitization of mice to topically applied drugs: albuterol, chlorpheniramine, clonidine and nadolol; Contact Dermatitis; 35(2); pp. 76-82; Aug. 1996.
Kelton et al.; The effects of nicotine on Parkinson's disease; Brain Cognition; 43(1-3); pp. 274-282; Jun. 2000.
Kennelly; Microcontrollers drive home drug delivery; 3 pgs; posted Jul. 2014; (retrieved Jul. 26, 2016 from the internet: http://electronicsmaker.com/microcontrollers-drive-home-drug-delivery-2.
Kiwi Drug; Buy nicorette microtabs; 3 pages; retrieved from the internet (www.kiwidrug.com/search/nicorette_microtabs); on Jul. 26, 2018.
Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.
Kulak et al.; 5-Iodo-A-85380 binds to oconotoxin Mil-sensitive nicotinic acetylcholine receptors (nAChRs) as well as 04j32* subtypes; Journal of Neurochemistry; 81(2); pp. 403-406; Apr. 1, 2002.
Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.
Kulak et al.; Loss of nicotinic receptors in monkey striatum after 1-methyl-4-phenyl-1,2,3,6-tetrahydropyridine treatment is due to a decline in oconotoxin Mil sites; Molecular Pharmacology; 61(1); pp. 230-238; Jan. 1, 2002.
Kumar et al.; Levodopa-dyskinesia incidence by age of Parkinson's disease onset; Movement disorders; 20(3); pp. 342-344; Mar. 2005.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4(2); pp. 17-21; (year of pub. sufficiently earlier than effective US filing date and any foreign priority date) 1997.
Lai et al.; Long-term nicotine treatment decreases striatal a6* nicotinic acetylcholine receptor sites and function in mice; Molecular Pharmacology; 67(5); pp. 1639-1647; May 1, 2005.
Lai et al.; Selective recovery of striatal 1251-a-conotoxinMII nicotinic receptors after nigrostriatal damage in monkeys; Neuroscience; 127(2); pp. 399-408; Dec. 31, 2004.
Lamberg; Chronotherapeutics: Implications for drug therapy; American Pharmacy; NS31(11); pp. 20-23; Nov. 1991.
Langston et al.; Investigating levodopa-induced dyskinesias in the parkinsonian primate; Annals of Neurology; 47(4 Suppl 1); pp. S79-S88; Apr. 2000.
Laser et al.; A review of micropumps; J. of Micromech. And Microeng.; 14; pp. R35-R64; Apr. 2004.
Lee et al.; A comprehensive review of opioid-induced hyperalgesia; Pain Physician; 14; pp. 145-161; Mar. 2011.
Lemay et al.; Lack of efficacy of a nicotine transdermal treatment on motor and cognitive deficits in Parkinson's disease; Prog Neuropsychopharmacol Biol Psychiatry: 28(1); pp. 31-39; Jan. 2004.
Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev, 6(1); pp. 83-100; Jan./Feb. 1991.

(56) References Cited

OTHER PUBLICATIONS

Lemmer; The clinical relevance of chronopharmacology in therapeutics; Pharmacological Research; 33(2); pp. 107-115; Feb. 1996.
Lewitt et al.; New developments in levodopa therapy; Neurology; 62(No. 1, Suppl. 1); pp. S9-S16; Jan. 2004.
Lieber Man; Compressed tablets by direct compression; Pharmaceutical Dosage forms; vol. 1, 2nd ed.; Marcel Dekker Inc.; pp. 195-246; (the year of publication is sufficiently earlier than the effective U.S. filing date and any foreign priority date so that the particular month of publication is not in issue) 1989.
Lieberman; Compression-coated and layer tablets; Pharmaceutical Dosage forms; vol. 1, 2nd ed.; Marcel Dekker Inc.; pp. 266-271; (the year of publication is sufficiently earlier than the effective U.S. filing date and any foreign priority date so that the particular month of publication is not in issue) 1989.
Lundblad et al.; Cellular and behavioural effects of the adenosine A2a receptor antagonist KW-6002 in a rat model of I-DOPA-induces Dyskinesia; Journal of Neurochemistry; 84(6); pp. 1398-1410; Mar. 2003.
Madandla et al,; Voluntary running provides neuroprotection in rats after 6-hydroxydopamine injection into the medial forebrain bundle; Metabolic Brain Disease; 19(1-2); pp. 43-50; Jun. 2004.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Matta et al.; Guidelines on nicotine dose selection for in vivo research; Psychopharmacology (Berl.); 190(3); pp. 269-319; Feb. 1, 2007.
Mccallum et al,; Decrease in alpha3*/alpha6* nicotinic receptors in monkey brain after nigrostriatal damage; Molecular Pharmacology; 68(3); pp. 737-746; Sep. 2005.
Mccallum et al.; Compensation in pre-synaptic dopaminergic function following nigrostriatal damage in primates; Journal of Neurochemistry; 96(4); pp. 960-972; Feb. 1, 2006.
Mccallum et al.; Differential regulation of mesolimbio alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.
Mccallum et al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.
McNeil Sweden AB. Package Leaflet: Information for the user. Nicorette Microtab Lemon 2mg sublingual tablets. (This leaflet was last approved in Apr. 16, 2008). retrived from ( www.lakemedelsverket.se/SPC_PIL/Pdf/enhumpil/Nicorette%20Microtab%20Lemon%202mg%20sublingual%20tablet%20ENG.pdf.) Accessed Aug. 19, 2010.
Medtronic; MiniMed Paradigm® Veo(TM) System (product info.); retrieved May 12, 2015from the internet: (http://www.medtronic.co.uk/your-health/diabetes/device/insulin-pumps/paradigm-veo-pump/); 3 pgs.
Meissner et al.; Priorities in parkinson's disease research; Nature reviews Drug Discovery: 10(5); pp. 377-393; May 1, 2011.
Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.
Merck manual of therapy and diagnosis; 17th edition. Merck Research Laboratories; pp. 1466-1471; (the year of publication is sufficiently earlier than the effective U.S. filing date and any foreign priority date so that the particular month of publication is not in issue) 1999.
Meredith et al.; Behavioral models of Parkinson's disease in rodents: a new look at an old problem; Movement Disorders; 21(10); pp. 1595-1606; Oct. 1, 2006.
Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; the year of publication is sufficiently earlier than the effective U.S. filing date and any foreign priority date so that the particular month of publication is not in issue) 2002.
Meshul et al.; Nicotine alters striatal glutamate function and decreases the apomorphine-induced contralateral rotations in 6-OHDA-lesioned rats; Experimental Neurology; 175(1); pp. 257-274; May 31, 2002.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16; pp. 1568-1567; Sep. 2006.
Nakadate et al.; Effects of chalcone derivatives on lipoxygenase and cyclooxygenase activities of mouse epidermis; Prostaglandins; 30(3); pp. 357-368; Sep. 1985.
National Institute of Neurological Disorders and Stroke. Parkinson's Disease: Hope Through Research. 54 pages; Retrieved from the internet (https://catalog.ninds.nih.gov/pubstatic//15-139/15-139.pdf) on Jan. 15, 2018.
Newhouse et al.; Nicotine treatment of mild cognitive impairment: a 6-month double-blind pilot clinical trial; Neurology; 78(2); pp. 91-101; Jan. 10, 2012.
Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.
OHDO; Changes in toxicity and effectiveness with timing of drug administration: implications for drug safety; Drug Safety; 26(14); pp. 999-1010; Dec. 2003.
Olanow: The scientific basis for the current treatment of Parkinson's disease; Annu. Rev. Med.; 55; pp. 41-60; Feb. 18, 2004.
Olsson et al.; A valve-less planar pump in silicon; IEEE; The 8th International Conference on Solid-State Sensors and Actuators; vol. 2; pp. 291-294, Jun. 1995.
Olsson et al.; An improved valve-less pump fabricated using deep reactive ion etching; Proc. Of the IEEE, 9th Int'l Workshop on MEMS; San Diego, CA, pp. 479-484; Feb. 11-15, 1996.
O'Neill et al.; The role of neuronal nicotinic acetylcholine receptors in acute and chronic neurodegeneration; Current Drug Targets-CNS and Neurological Disorders; 1(4); pp. 399-412; Aug. 1, 2002.
Parkinson Study Group; Levodopa and the progression of Parkinson's disease; N Engl J Med.; 351; pp. 2498-2508; Dec. 9, 2004.
Petzinger et al.; Reliability and validity of a new global dyskinesia rating scale in the MPTP-lesioned non-human primate; Movement Disorders; 16(2); pp. 202-207; Mar. 1, 2001.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; Chronic oral nicotine normalizes dopaminergic function and synaptic plasticity in l-methyl-4-phenyl-1,2,3,6-tetrahydropyridine-lesioned primates; The Journal of Neuroscience; 26(17); pp. 4681-4689; Apr. 26, 2006.
Quik et al.; Chronic oral nicotine treatment protects against striatal degeneration in MPTP-treated primates; Journal of Neurochemistry: 98(6); pp. 1866-1875; Sep. 1, 2006.
Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.
Quik et al.; Differential declines in striatal nicotinic receptor subtype function after nigrostriatal damage in mice; Molecular Pharmacology; 63(5); pp. 1169-1179; May 1, 2003.

(56) References Cited

OTHER PUBLICATIONS

Quik et al.; Differential nicotinic receptor expression in monkey basal ganglia: Effects of nigrostriatal damage; Neuroscience; 112(3); pp. 619-630; Jul. 5, 2002.
Quik et al.: Expression of D3 receptor messenger RNA and binding sites in monkey striatum and substantia nigra after nigrostriatal degeneration: Effect of levodopa treatment.; Neuroscience; 98(2); pp. 263-273; Jun. 30, 2000.
Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.
Quik et al.; L-DOPA treatment modulates nicotinic receptors in monkey striatum; Mol Pharmacol; 64(3); pp. 619-628; Sep. 2003.
Quik et al.; Localization of nicotinic receptor subunit mRNAs in monkey brain by in situ hybridization; The Journal of Comparative Neurology; 425(1); pp. 58-69; Sep. 11, 2000.
Quik et al.; Loss of a-conotoxinMII- and A85380-sensitive nicotinic receptors in Parkinson's disease striatum; Journal of Neurochemistry; 88(3); pp. 668-679; Feb. 1, 2004.
Quik et al.; Nicotine administration reduces striatal MPP+ levels in mice; Brain Research; 917(2); pp. 219-224; Nov. 2, 2001.
Quik et al.; Nicotine and nicotinic receptors; relevance to Parkinson's disease; Neurotoxicology; 23(4-5); pp. 581-594; Oct. 2002.
Quik et al.; Nicotine and Parkinson's disease: implications for therapy; Movement Disorders; 23(12); pp. 1641-1652; (Author Manuscript); Sep. 1, 2008.
Quik et al.; Nicotine as a potential neuroprotective agent for Parkinson's disease; Movement disorders; 27(8); pp. 947-957; Jul. 1, 2012.
Quik et al.; Nicotine neuroprotection against nigrostriatal damage: importance of the animal model; Trends in Pharmacological sciences; 28(5); pp. 229-235; May 31, 2007.
Quik et al.; Nicotine reduces levodopa-induced dyskinesias in lesioned monkeys; Annals of neurology; 62(6); pp. 588-596; (Author Manuscript); Dec. 1, 2007.
Quik et al.; Nicotinic receptors and Parkinson's disease; European Journal of Pharmacology; 393(1); pp. 223-230; Mar. 30, 2000.
Quik et al.; Striatal a6* nicotinic acetylcholine receptors: Potential targets for Parkinson's disease therapy; The Journal of Pharmacology and Experimental Therapeutics; 316(2); pp. 481-489; Feb. 1, 2006.
Quik et al.; Subunit composition of nicotinic receptors in monkey striatum: Effect of treatments with 1-methyl-4-phenyl-1,2,3,6-tetrahydropyridine or L-DOPA; Molecular Pharmacology; 67(1); pp. 32-41; Jan. 2005.
Quik et al.; Vulnerability of 125I-a-conotoxin MiI binding sites to nigrostriatal damage in monkey; The Journal of Neuroscience; 21(15); pp. 5494-5500; Aug. 1, 2001.
QUIK; Smoking, nicotine and Parkinson's disease; Trends in Neurosciences; 27 (9); pp. 561-568; Sep. 2004.
Redfern et al.; Circadian rhythms, jet lag, and chronobiotics: An overview; Chronobiology International; 11(4); pp. 253-265; Aug. 1994.
ReinbergG; Concepts of Circadian Chronopharmacology; Annals of the New York Academy of Sciences; 618 (Temporal Control of Drug Delivery); pp. 102-115; Feb. 1991.
Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.
Samii et al.; Parkinson's disease; The Lancet; 363(9423); pp. 1783-1793; May 29, 2004.
Savitt et al.; Diagnosis and treatment of Parkinson disease: molecules to medicine; The Journal of Clinical Investigation; 116(7); pp. 1744-1754; Jul. 3, 2006.
Schapira; Disease modification in Parkinson's disease; The Lancet Neurology; 3(6); pp. 362-368; Jun. 30, 2004.

Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.
Schneider et al.; Effects of the nicotinic acetylcholine receptor agonist SIB-1508Y on object retrieval performance in MPTP-treated monkeys: Comparison with levodopa treatment; Annals of Neurology; 43(3); pp. 311-317; Mar. 1, 1998.
Schober et al.; Classic toxin-induced animal models of Parkinson's disease: 6-OHDA and MPTP; Cell and Tissue Research; 318(1); pp. 215-224; Oct. 1, 2004.
Shin et al.; Enhanced bioavailability of triprolidine from the transdermal TPX matrix system in rabbits; Int. J. Pharm.; 234(1-2); pp. 67-73; Mar. 2002.
Silver et al.; Transdermal nicotine and haloperidol in Tourette's disorder: a double-blind placebo-controlled study; Journal of Clinical Psychiatry; 62(9); pp. 707-714; Sep. 1, 2001.
Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).
Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.
Stocchi et al.; Motor fluctuations in levodopa treatment: clinical pharmacology; European Neurology; 36(Suppl 1); pp. 38-42; Jan. 1996.
Strong et al.; Genotype and smoking history affect risk of levodopa-induced dyskinesias in parkinson's disease; Movement Disorders; 21(5); pp. 654-659; May 1, 2006.
Thiele et al. (Ed.); Oxidants and Antioxidants in Cutaneous Biology: Current Problems in Dermatology (Book 29); S. Karger; 196 pgs.; Feb. 2001.
Togasaki et al.; Dyskinesias in normal squirrel monkeys induced by nomifensine and levodopa; Neuropharmacology; 48(3); pp. 398-405; Mar. 31, 2005.
Togasaki et al.; Levodopa induces dyskinesias in normal squirrel monkeys; Annals of Neurology; 50(2); pp. 254-257; Aug. 1, 2001.
Togasaki et al.; The Webcam system: A simple, automated, computer-based video system for quantitative measurement of movement of nonhuman primates; Journal of Neuroscience Methods; 145(1); pp. 159-166; Jun. 30, 2005.
Tolosa et al.; Antagonism by piperidine of levodopa effects in Parkinson disease; Neurology; 27(9); pp. 875-877; Sep. 1, 1977.
U.S. Department of Health and Human Services, Food and Drug Administration, Center for Drug Evaluation and Research (CDER); Guidance for industry: Abuse-deterrent opioids-Evaluation and labeling; 24 pages; retrieved from the internet (http://www.fda.gov/downloads/drugs/guidancecomplainceregulatoryinformation/guidances/ucm344743.pdf); Jan. 2013.
United States of America VA/DoD; Tapering and discontinuing opioids; 2 pages; retrieved from the internet (http://www.healthquality.va.gov/guidelines/Pain/cof/OpioidTaperingFactSheet23May2013v1.pdf); on Sep. 1, 2016.
Vieregge et al.; Transdermal nicotine in PD: A randomized, double-blind, placebo-controlled study; Neurology; 57(6); pp. 1032-1035; Sep. 25, 2001.
Villafane et al.; Long-term nicotine administration can improve Parkinson's disease: report of a case after three years of treatment; Revista Neurologica Argentina; 27(2); pp. 95-97; (the year of publication is sufficiently earlier than the effective U.S. filing date and any foreign priority date so that the particular month of publication is not in issue) 2002.
Warburton et al.; Facilitation of learning and state dependency with nicotine; Psychopharmacology; 89(1); pp. 55-59; May 1, 1986.
Wermuth et al.; Glossary of terms used in medicinal chemistry Pure & Appl. Chem., vol. 70(5); 1129-1143; 1998 AC recommendations 1998); Pure and Applied Chemistry: 70(5); pp. 1129-1143; Jan. 1998.
Wesnes et al.; Effects of scopolamine and nicotine on human rapid information processing performance; Psychopharmacology; 82(3); pp. 147-150; Sep. 1, 1984.

(56) References Cited

OTHER PUBLICATIONS

Westman et al.; Oral nicotine solution for smoking cessation: a pilot tolerability study; Nicotine and Tobacco Research; 3(4); pp. 391-396; Nov. 1, 2001.
Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.
Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity In mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.
Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.
Wille; Thixogel: Novel topical delivery system for hydrophobic plant actives; in ROSEN (Ed.) Delivery System Handbook for Personal Care and Cosmetic Products; 1st Ed.; ISBN: 978-0-8155-1504-3; pp. 762-794; Sep. 2005.
Youan; Chronopharmaceutics: gimmick or clinically relevant approach to drug delivery ?; J Cont Rel; 98(3); pp. 337-353; Aug. 2004.
Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.
Zubieta et al.; Placebo effects mediated by endogenous opioid activity on mu-opioid receptors; 25(34); pp. 7754-7762; Aug. 24, 2005.
Tong et al.; U.S. Appl. No. 18/178,442 entitled "Drug Delivery methods and systems," filed Mar. 3, 2023.

\* cited by examiner

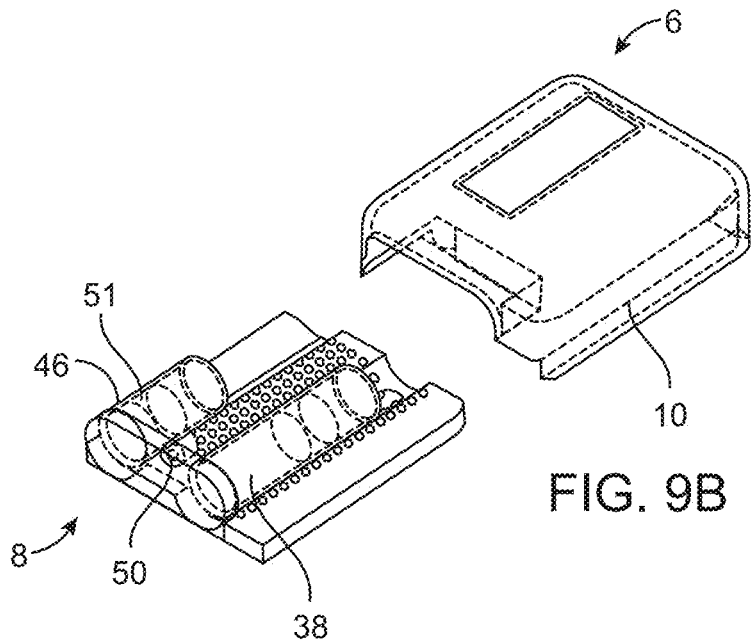
FIG. 9A
FIG. 9B
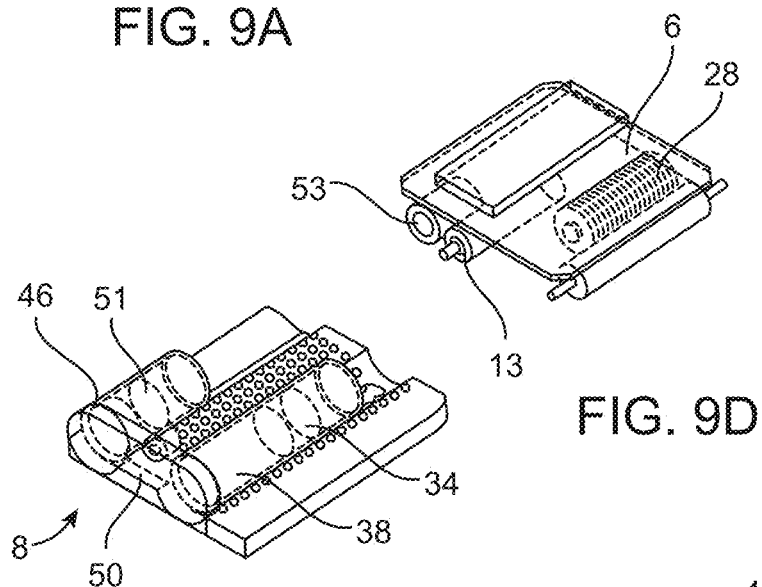
FIG. 9C
FIG. 9D
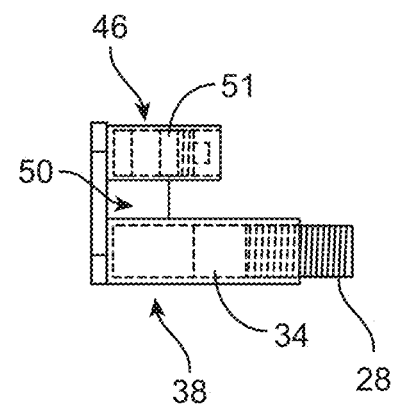
FIG. 9E

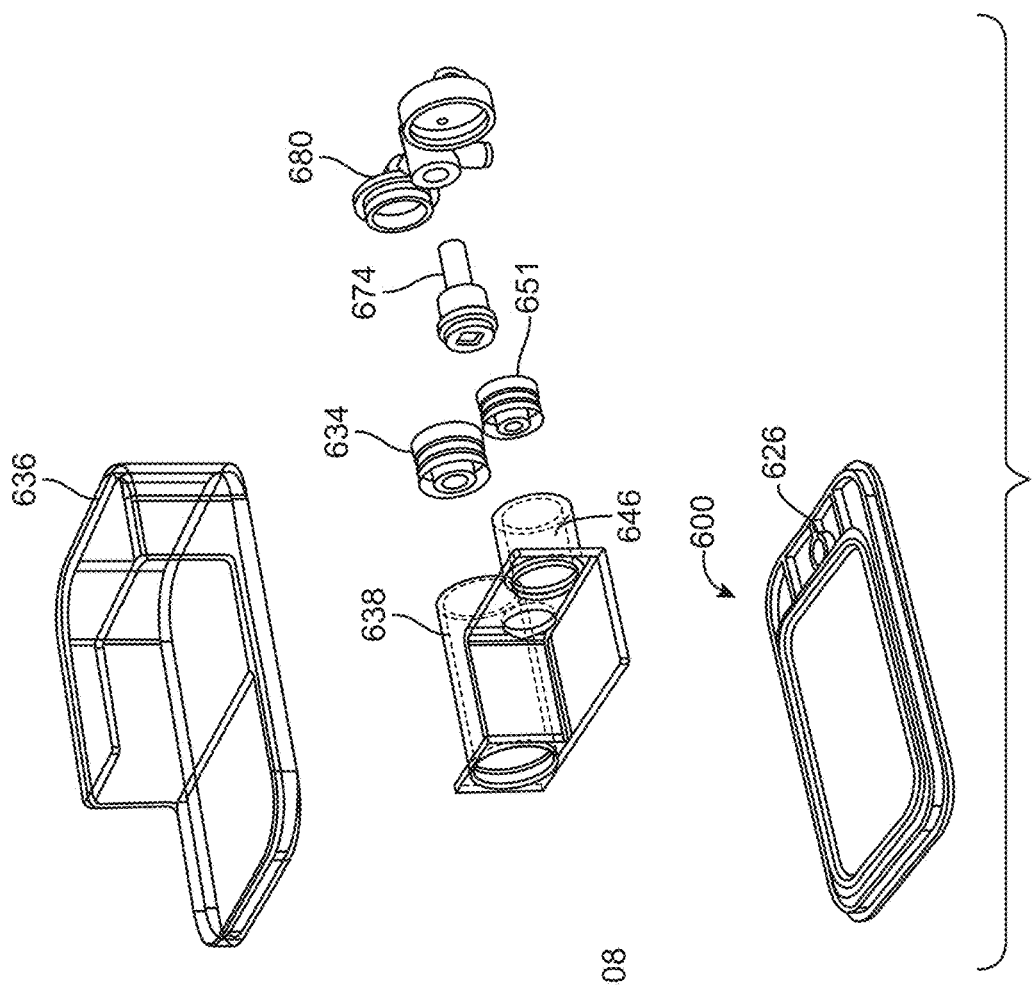
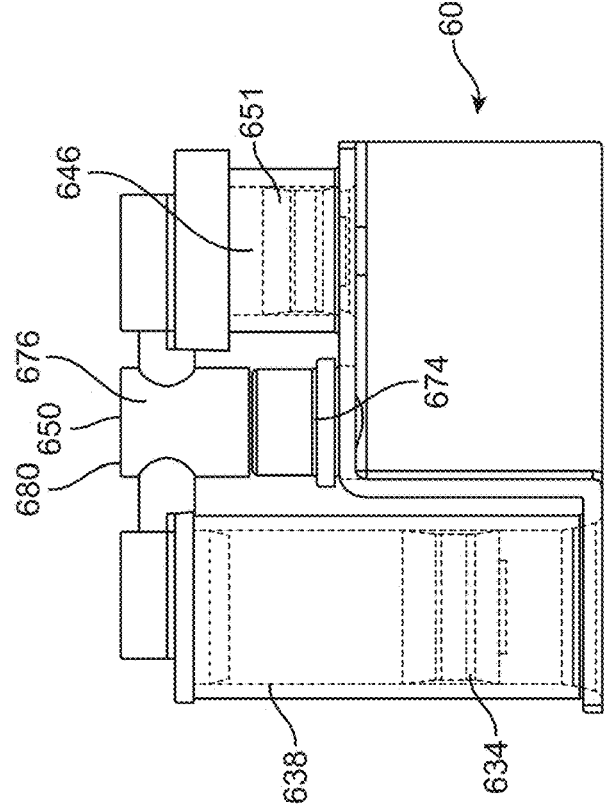
FIG. 15B
FIG. 15A

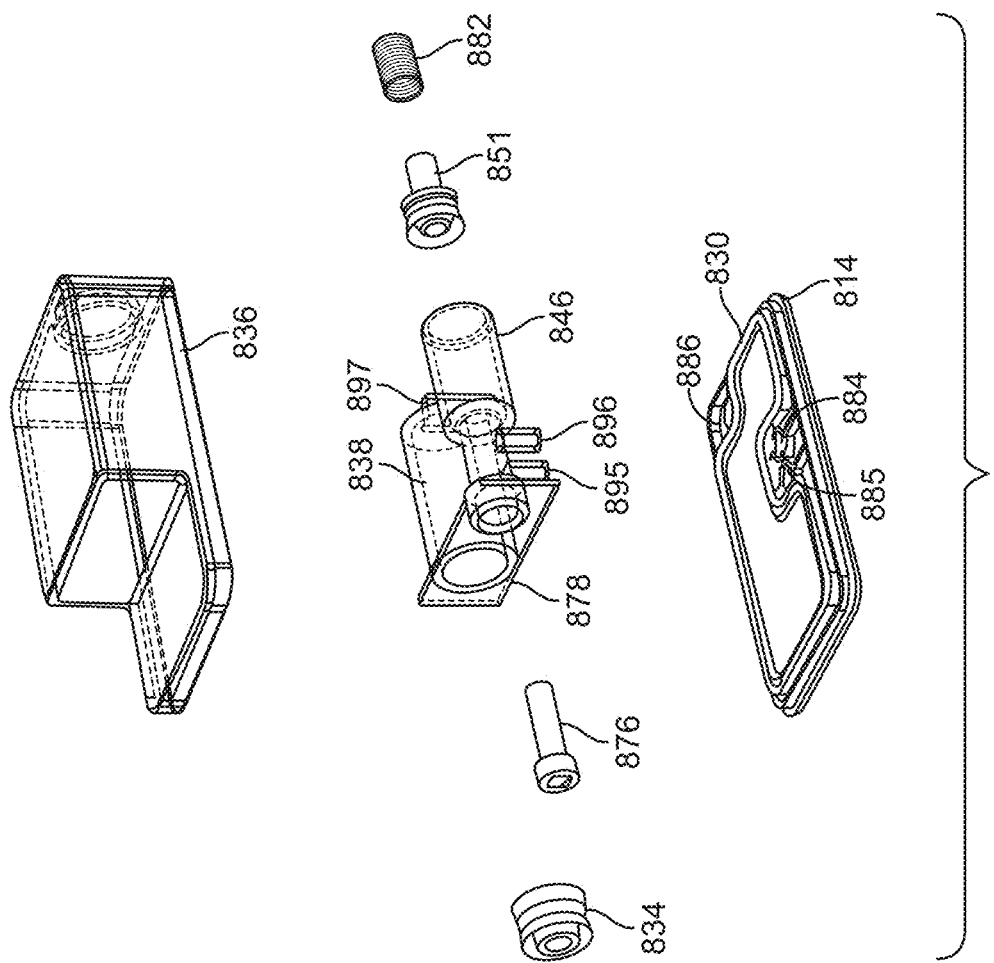
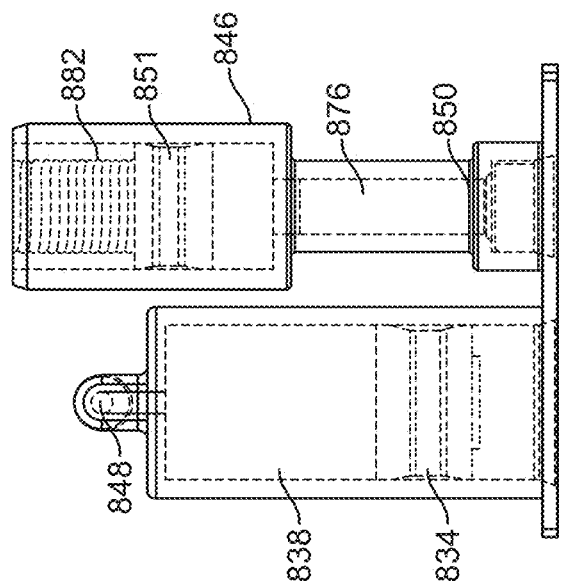
FIG. 17B
FIG. 17A

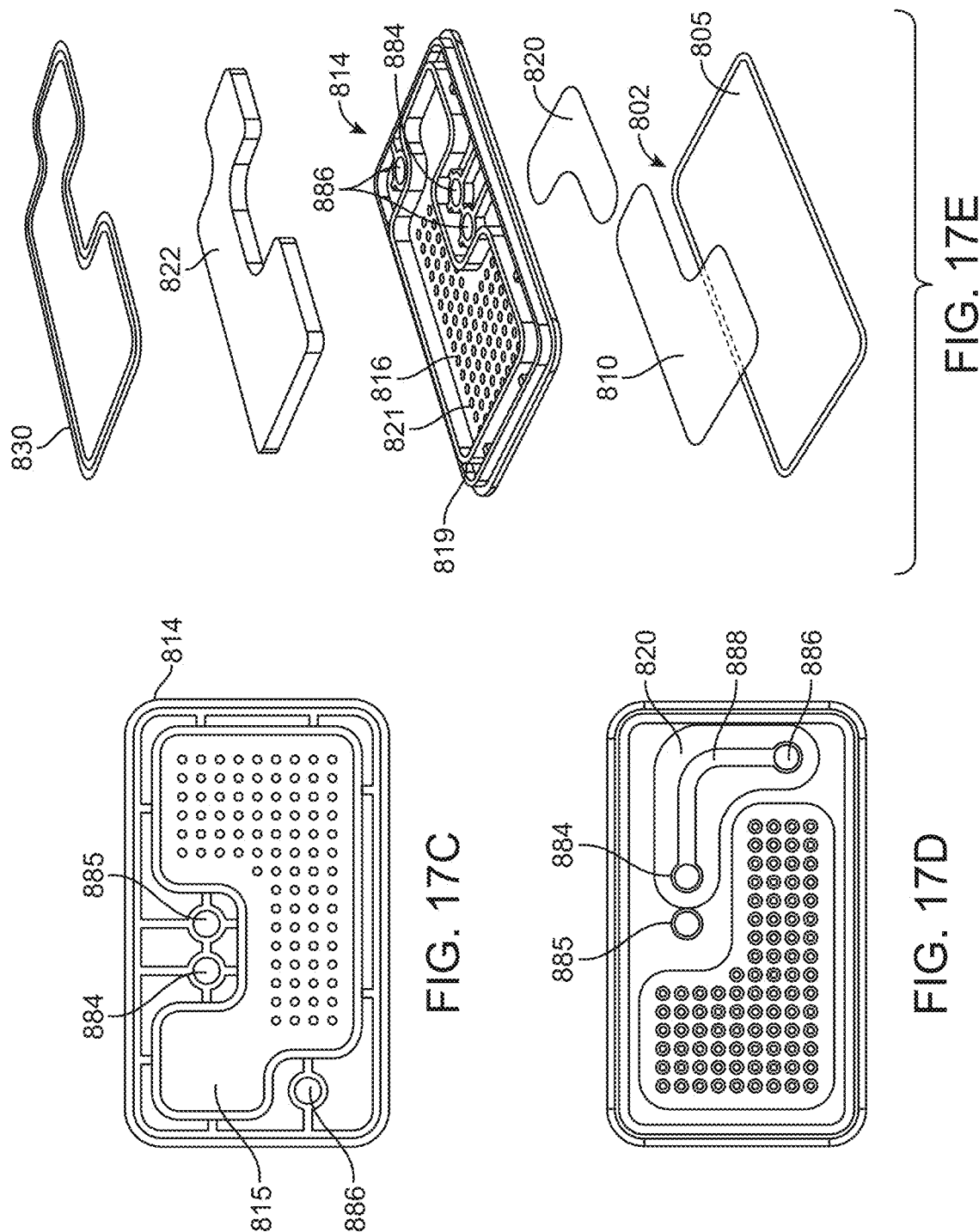

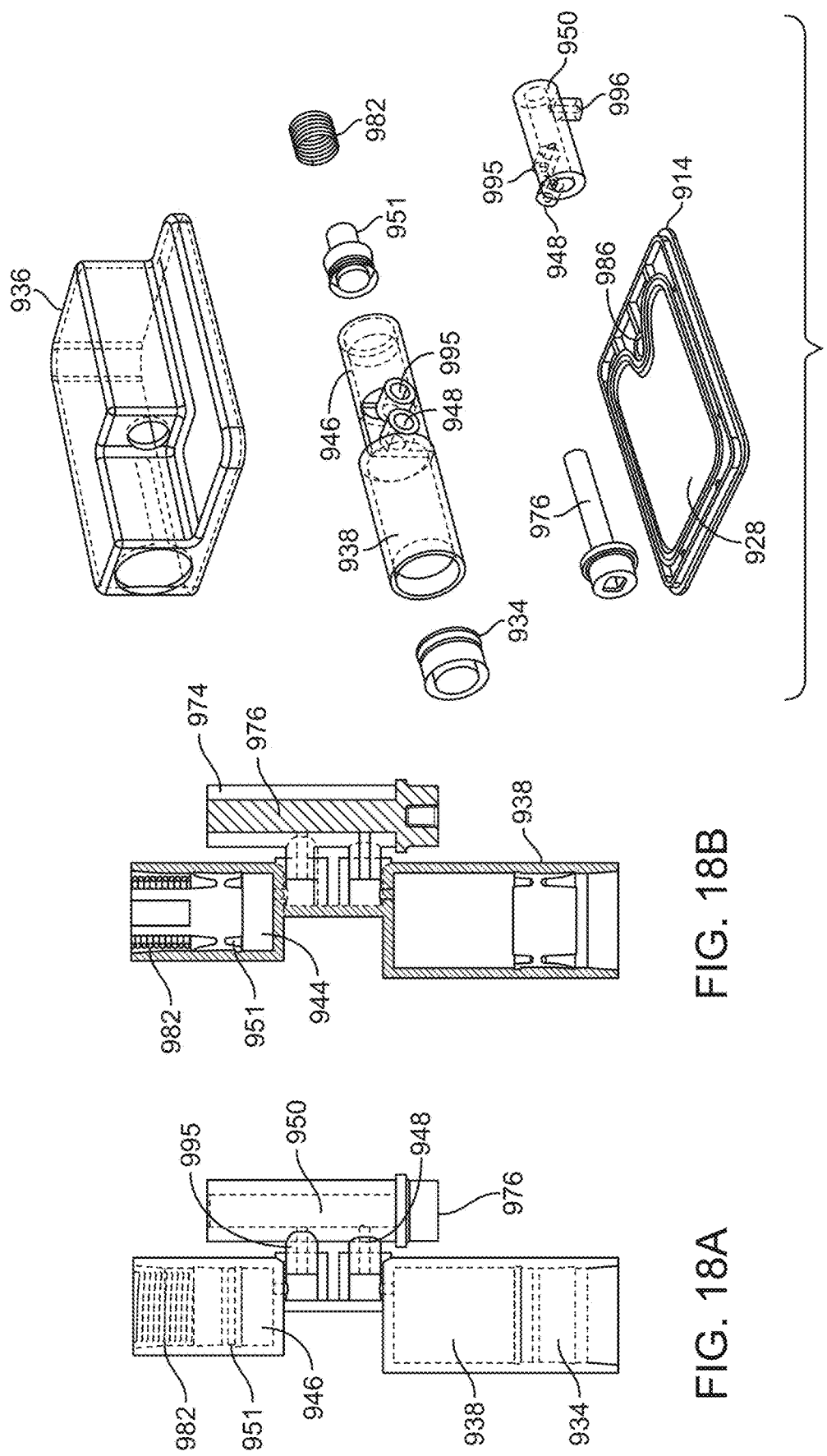

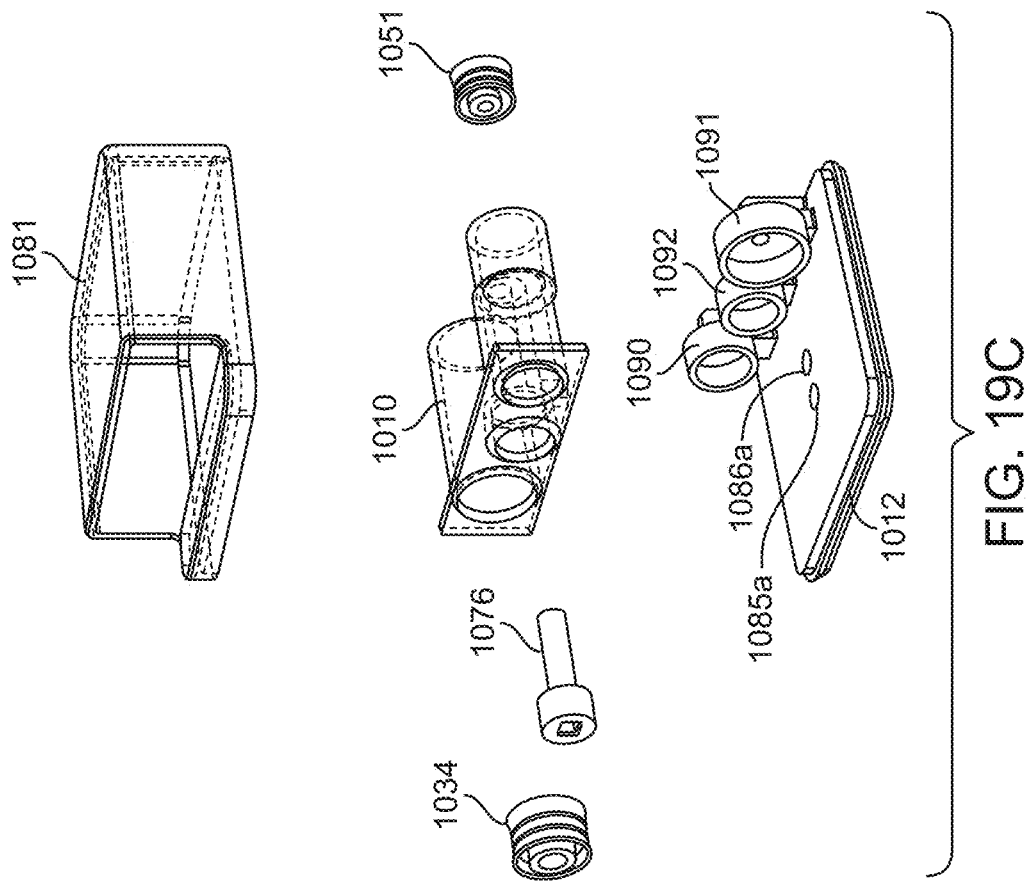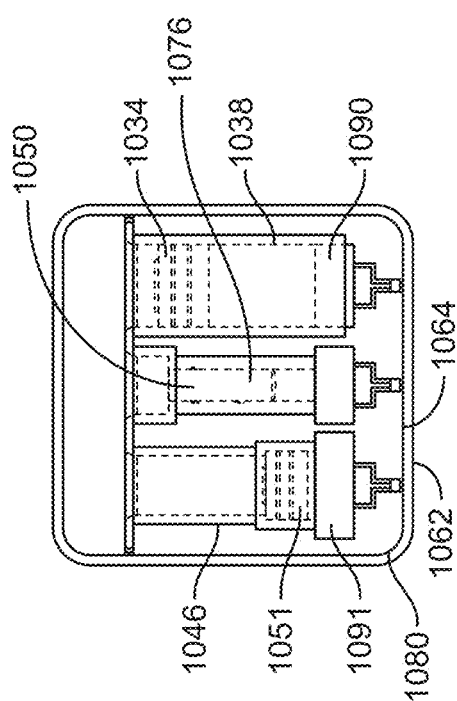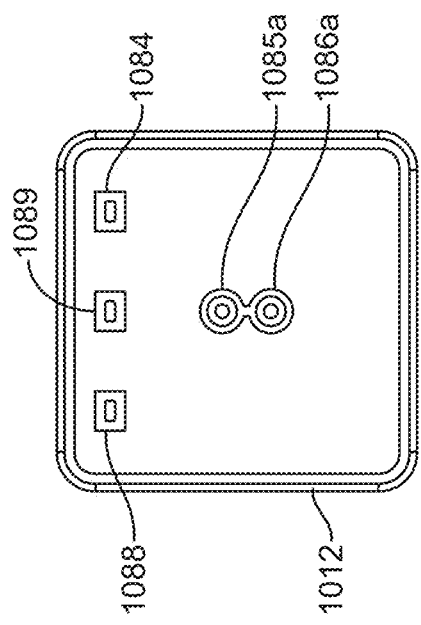

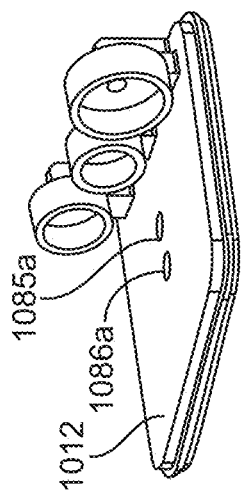
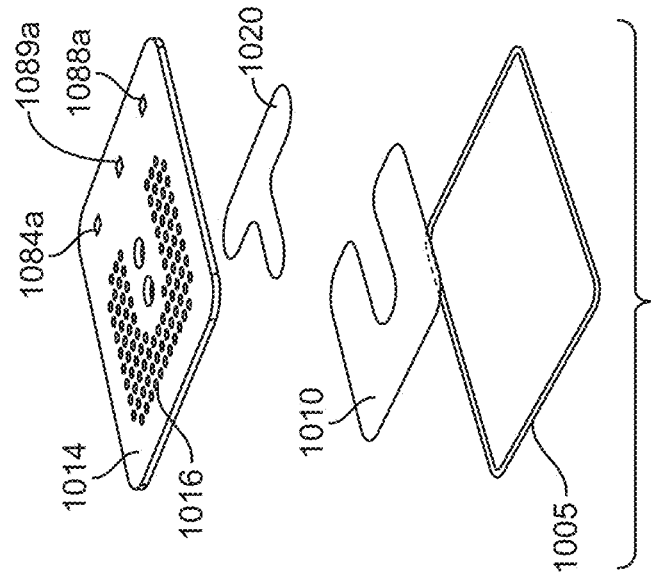
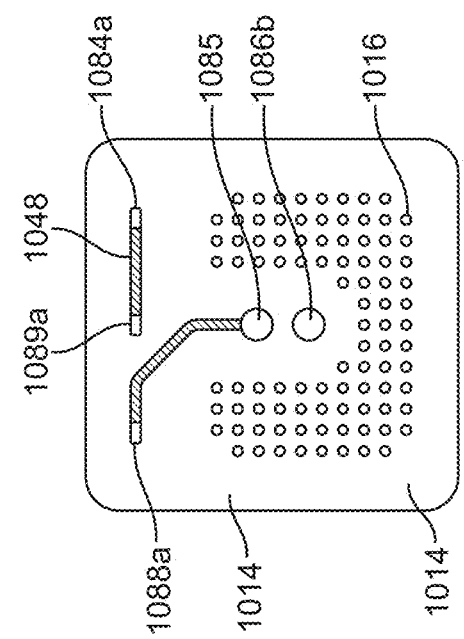
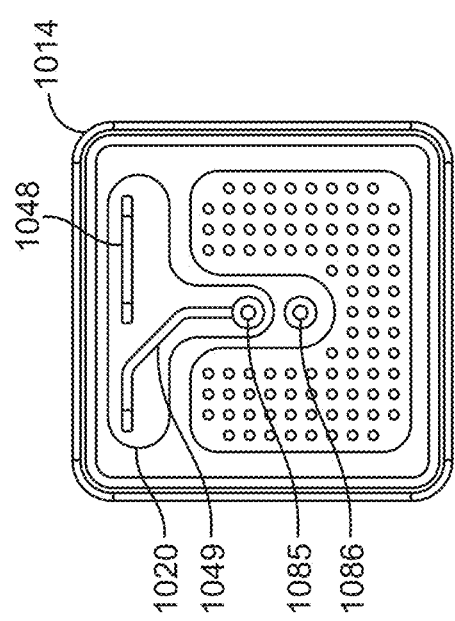
FIG. 19D
FIG. 19E
FIG. 19F

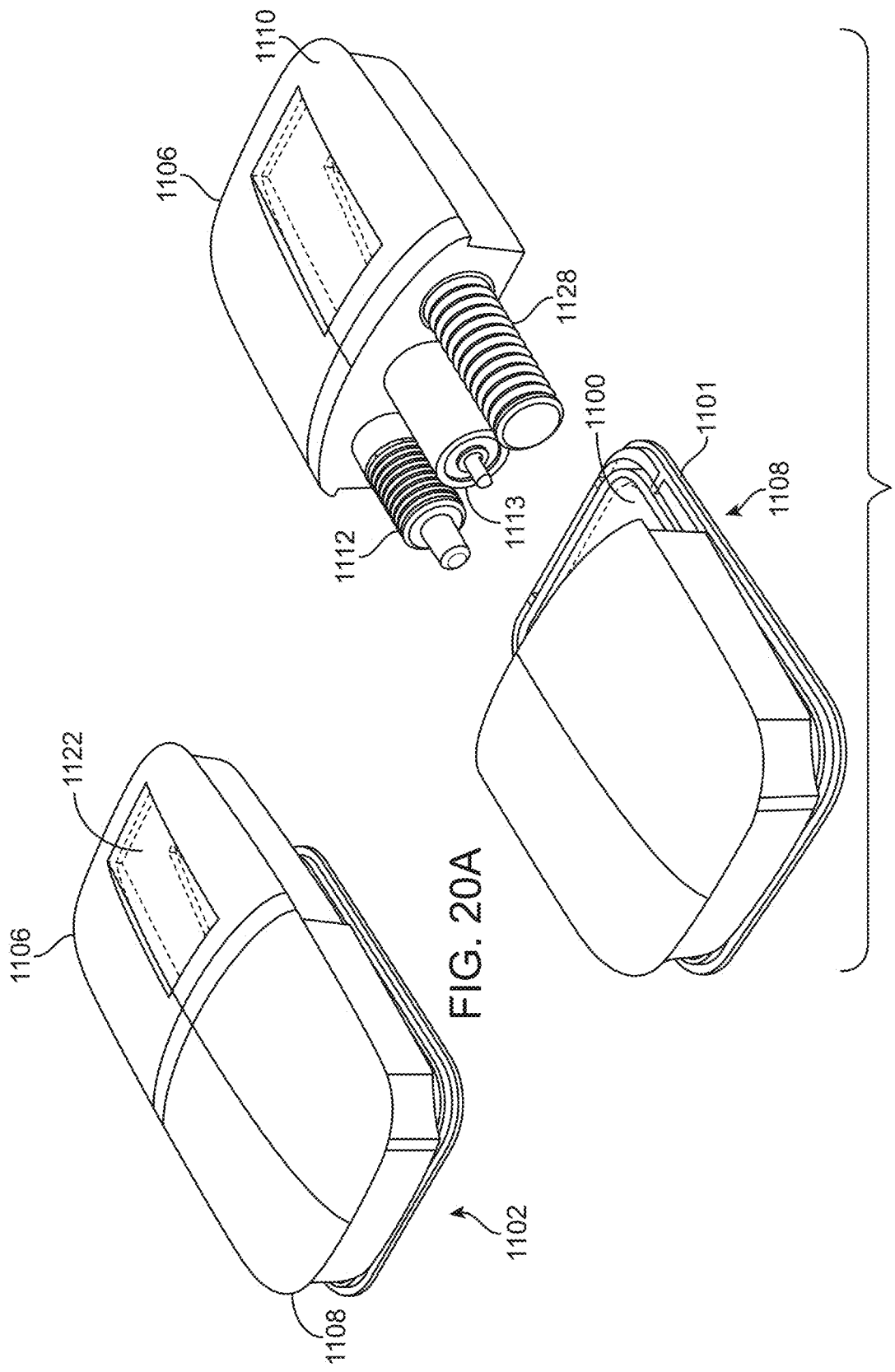

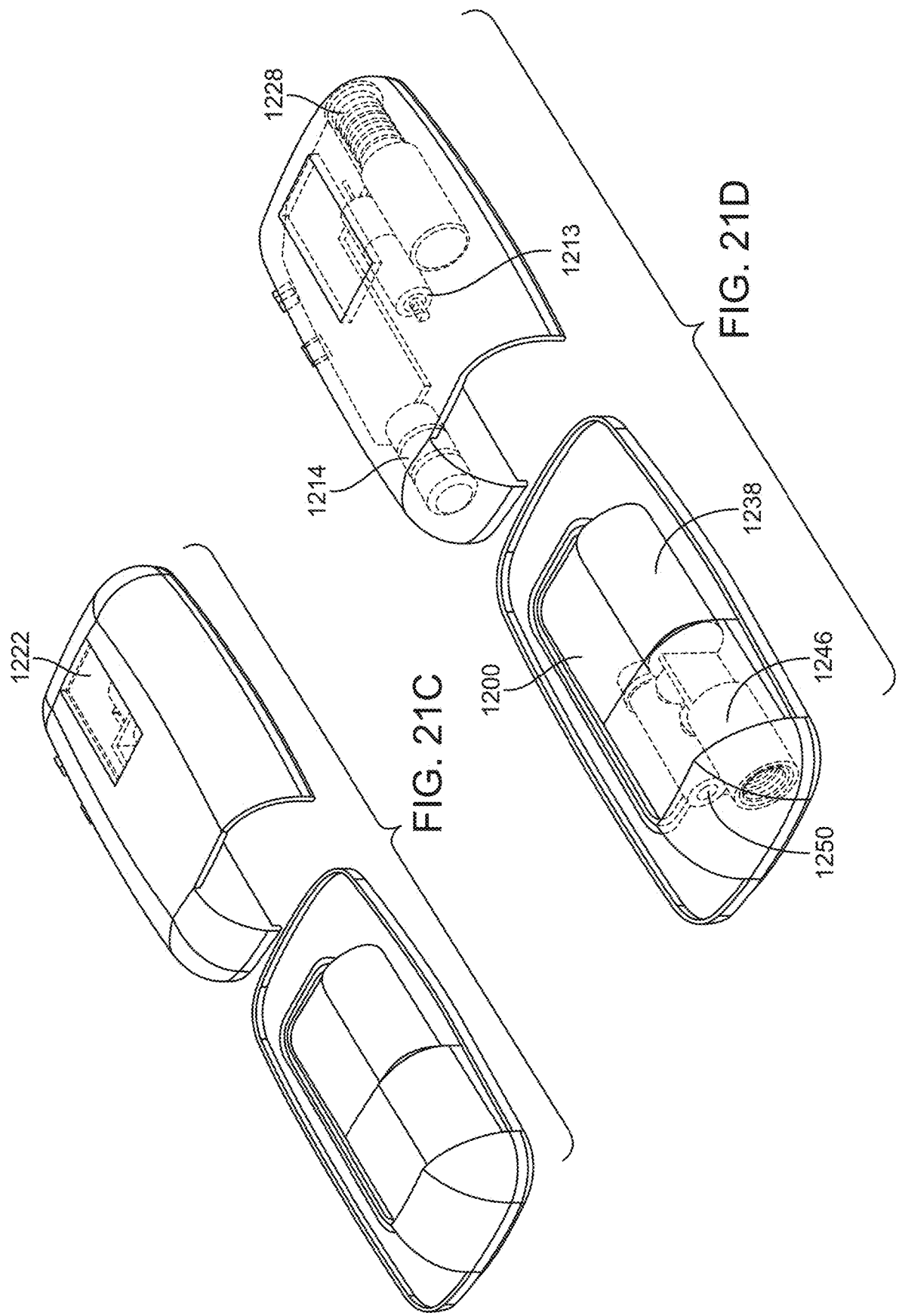

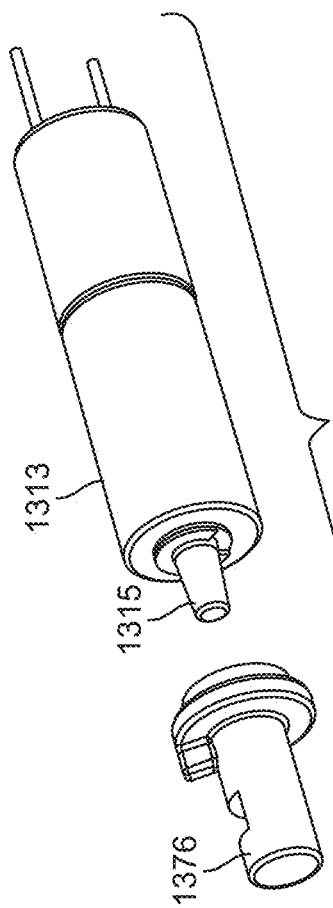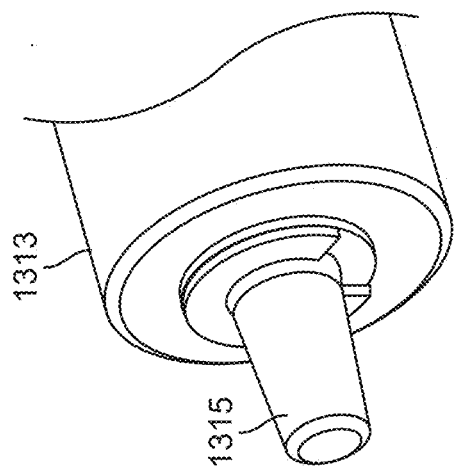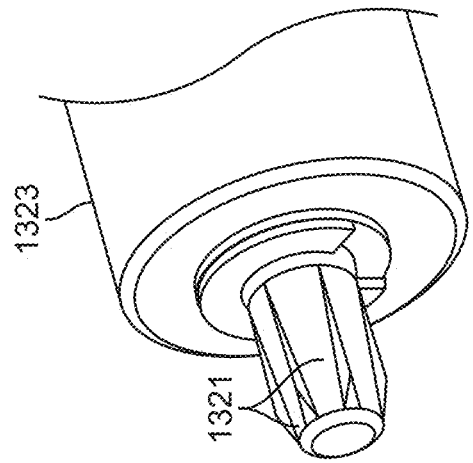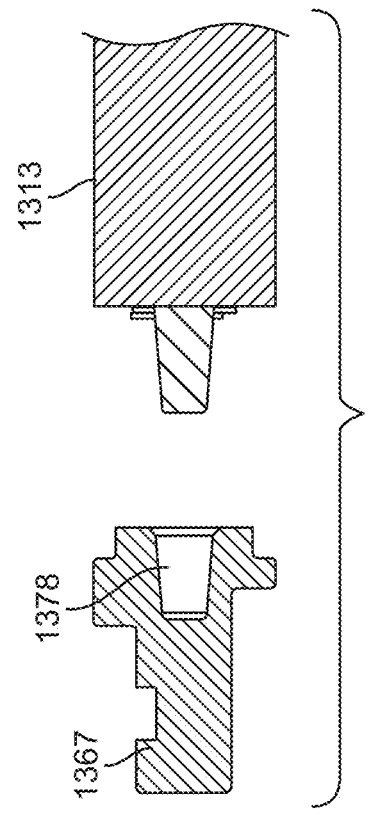

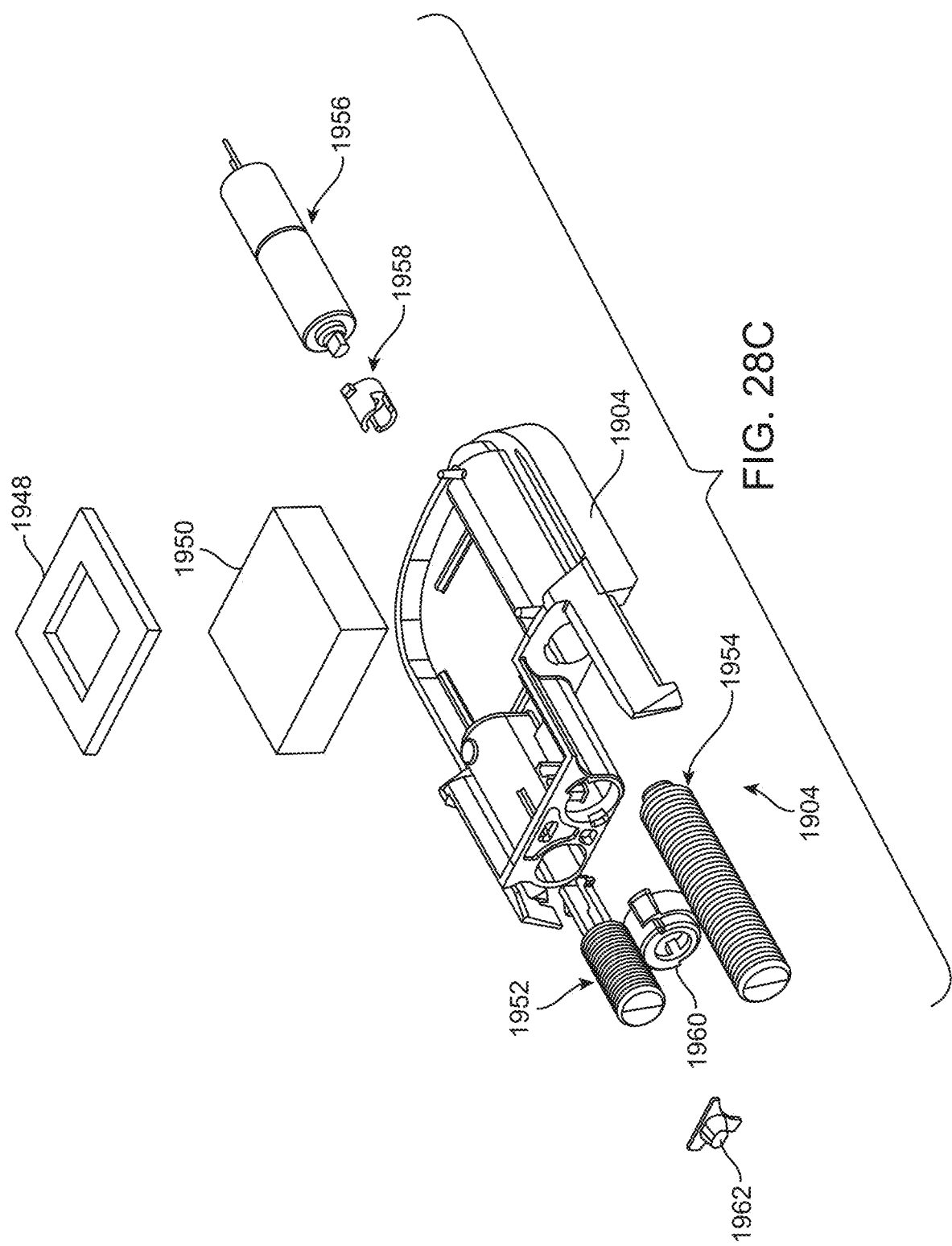

DRUG DELIVERY METHODS AND SYSTEMS

CROSS REFERENCE TO RELATED APPLICATIONS

This application is a continuation of U.S. patent application Ser. No. 16/284,933, filed Feb. 25, 2019, now U.S. Patent Application Publication No. 20190275308, which is a continuation of U.S. patent application Ser. No. 15/699,382, filed Sep. 8, 2017, now U.S. Pat. No. 10,232,156, which is a divisional of U.S. application Ser. No. 15/009,683, filed Jan. 28, 2016, now U.S. Pat. No. 10,213,586, which claims the benefit of U.S. Provisional Application No. 62/108,959, filed Jan. 28, 2015; U.S. Provisional Application No. 62/132,436, filed Mar. 12, 2015; and U.S. Provisional Application No. 62/263,516, filed Dec. 4, 2015, the disclosures of which are incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Medicinal drugs are given to people to manage or improve their health for a variety of reasons, such as to prevent or treat a medical condition or disease such as diabetes, Parkinson's disease, ulcerative colitis, or to manage nicotine or another addiction or dependency, or to manage pain.

Some medicinal drugs are rapidly metabolized by the body; multiple doses of the drug over a period of time are therefore often needed to provide a desired effect. In addition to having desired preventative or therapeutic effects, medicinal drugs can also have negative side-effects on the body that can range from irritating to life-threatening. A person's body can also develop tolerance to a drug and experience a diminished response to the drug after taking it for a period of time and require higher doses to have an effect, resulting in increased drug use and additional side-effects. Despite their negative side-effects, a person takes a medicinal drug because, on the whole, the drug causes more good than harm. It is beneficial to a person taking a drug to minimize the amount of drug they take to prevent or minimize tolerance and other unwanted side-effects while still receiving the desired therapeutic effect from the drug.

Tobacco use (such as smoking) causes serious health problems and can lead to premature death. According to the United States Center for Disease Control (CDC), tobacco use causes more than 5 million deaths per year as well as contributing to the development of serious illnesses such as cancer, diabetes, heart disease, lung disease (bronchitis, chronic airway destruction, emphysema), and stroke. Despite anti-smoking advertising campaigns, legislation, taxation, and development of smoking cessation products to stop or prevent people from using tobacco, tobacco sales remains a multibillion dollar industry, generating an estimated $35 billion dollars per year in profits. Tobacco initially causes physical and mood-altering effects that are temporarily pleasing. It is difficult for a person to stop using a tobacco product, because tobacco contains nicotine. Nicotine is highly addictive, and not having the nicotine causes harsh withdrawal symptoms. It is very difficult for a person to overcome a nicotine addiction and stop smoking.

Medicinal drugs can be taken by tobacco users to help them to overcome their nicotine addiction and stop using tobacco. Some products to help a person stop smoking contain small amounts of nicotine as a medicinal drug to minimize withdrawal symptoms and gradually wean a person from their nicotine addiction. Medicinal smoking cessation drugs such as nicotine have to be taken over an extended period of time (often over the course of many months) to give the body time to adjust to having less nicotine. Medicinal drugs, medical devices and other products, including smoking cessation products, are regulated in the United States by the U.S. Food and Drug Administration (FDA). FDA approved products on the market to help a person quit smoking include various medicinal drugs that require a doctor's prescription as well as over-the-counter products. These products include capsules or tablets, gums, inhalers, lozenges, nasal sprays, and skin patches. These products have thus far been inadequate to get people to stop smoking: 68.9% of adult cigarette smokers say they want to stop smoking, and every year some 42.7% make an attempt to stop smoking, but are unsuccessful.

These existing smoking cessation products and other therapeutic and prophylactic treatments for health issues suffer from a variety of problems. They may be inconvenient or socially awkward to use. They may require careful and troublesome tracking of when they were used and how much was used to prevent overdosing. They may act too slowly after being administered and not produce a desired effect when it's needed. They may not be readily available when they are needed (such as while a person is sleeping). None have been wholly effective to for preventing or treating various medical or other conditions. Smoking, for example, remains a significant health and social problem.

What are needed are new and improved systems, devices and methods for delivering drugs and other bioactive agents, such as smoking cessation agents, to a person. Provided herein are systems, devices and methods for delivering a drug or other bioactive agent to an individual. These may be useful for treating or preventing a medical condition, disease, addiction, dependency or for managing pain and may be especially useful for helping a tobacco user to stop using tobacco. New and improved systems with increased safety and improved efficiency for delivering the drugs and other bioactive agents are also desired and disclosed herein.

SUMMARY OF THE DISCLOSURE

The present invention relates generally to systems for delivering bioactive agents and methods for using the systems to delivery bioactive agents.

One aspect of the invention provides a two-part bioactive agent delivery system, the system including a disposable part comprising an agent reservoir (having a volume, e.g., of less than about 3 ml.), the agent reservoir having a piston movably disposed in a chamber, a bolus chamber (having a volume, e.g., of less than about 0.5 ml), the bolus chamber having a piston movably disposed in a chamber, the volume of the bolus chamber being less than the volume of the agent reservoir, an agent outlet, and a valve having a first position communicating the agent reservoir with the bolus chamber and a second position communicating the bolus chamber with the outlet; and a reusable part including a valve driver, a power source and control electronics, the control electronics being adapted to control the valve driver to actuate the valve to deliver bioactive agent from the agent reservoir to the agent outlet; the system further having a spring (or other source of stored mechanical energy) extending between the agent reservoir piston and a surface of the reusable part or of the disposable part to pressurize the agent reservoir when the spring is compressed and the agent reservoir contains a quantity of bioactive agent. The valve may be a rotatable valve having a range of motion between 60° to 90°, inclusive. In some embodiments, the bolus chamber is configured to provide a bioactive agent dissolved in a solvent to the agent outlet. The system may also have a disengagement button configured to disengage the reusable part from the disposable part.

In some embodiments, the system may also have a transdermal patch (e.g., a polypropylene membrane, optionally having pores with an average pore diameter of about 0.02 μm to about 0.10 μm) communicating with the outlet and adapted to transdermally deliver the bioactive agent to a user. In addition, some embodiments of the invention may include a solvent recovery chamber disposed in the disposable part and communicating with the transdermal patch, the solvent recovery chamber being adapted to receive gaseous phase solvent from the transdermal patch. Such embodiments of the system may also have a desiccant or absorbent material disposed in the solvent recovery chamber.

In some embodiments, the spring may be disposed in the disposable part prior to connecting the disposable part to the reusable part, and in some embodiments the spring may be disposed in the reusable part prior to connecting the disposable part to the reusable part. Some embodiments may have a second spring extending between the bolus chamber piston and a surface, the second spring being at least partially loaded when a quantity of bioactive agent is present in the bolus chamber. In some embodiments, the second spring extends between the bolus chamber piston and a surface in the disposable part, the bolus chamber piston being adapted to move and load the second spring when pressurized bioactive agent enters the bolus chamber from the agent reservoir through the valve. In other embodiments, the second spring extends between the bolus chamber piston and a surface in the reusable part.

In embodiments employing a transdermal patch, the system may also have a vapor permeable membrane in the disposable part adjacent to the transdermal patch. In such embodiments, the agent outlet may be configured to provide the bioactive agent dissolved in the solvent to a space between the transdermal patch and the vapor permeable membrane. The vapor permeable membrane may also be in fluid communication with the solvent recovery chamber. The transdermal patch may be adapted to allow the bioactive agent to pass through a plurality of openings in the transdermal patch while substantially preventing the solvent from passing through the plurality of openings of the transdermal patch.

In some embodiments, the agent reservoir and bolus chamber are configured to contain a bioactive agent and a solvent solution comprising alcohol and water, wherein the solvent solution has a ratio of water to alcohol of about 40:60 to about 60:40.

Some embodiments of the system may include a connection indicator operatively connected to the control electronics to provide an indication that the reusable part has been connected to the disposable part. The connection indicator may be, e.g., a movable switch and/or two members that cooperate to close a circuit, such as a first conductor (formed, e.g., of a conductive elastomeric material) on the reusable part and a second conductor (formed, e.g., of a conductive elastomeric material) on the disposable part, the first and second conductors being arranged and disposed to close an electric circuit when the reusable part is connected to the disposable part.

Some embodiments of the system may include a display on the reusable part, the display being operatively connected to the control electronics. The system may also include one or more user actuatable buttons operatively connected to the control electronics, the control electronics may also be further adapted to detect actuation of a button and to display a message on the display in response to detecting actuation of the button. The system may also have a wireless transmitter configured to wirelessly transmit to another device a signal indicating actuation of the button and may also have a receiver configured to receive a wireless signal from the other device, the control electronics being further configured to display a message on the display in response to the wireless signal received on the receiver.

In some embodiments, the system includes a wireless data communication module configured to send and receive data wirelessly to a network or a computing device via, e.g., a Bluetooth connection. In some embodiments, the system has one or more buttons configured to provide an input to the system, such as, e.g., to change the system operation mode and/or select inputs.

In some embodiments, the bioactive agent is selected from the group consisting of: Acamprosate, Acetaminophen, Acetaminophen+Oxycodone, Alevicyn SG, Alfentanil, Allopurinol, Almotriptan, Alprazolam, Alprazolam XR, Amitriptylinem, Amoxapine, Apomorphine, Aripiprazole, Armodafinil, Asenapine maleate, Atomoxetine, Azelastine HCL, Baclofen, Benzbromarone, Benzydamine, Brexpiprazole, Budesonide, Bupivacaine, Buprenorphine, Buprenorphine+Nalaxone, Bupropion, Bupropion Hydrobromide, Bupropion Hydrochloride, Bupropion SR, Bupropion XR, Buspirone, Cabergoline, Capsaicin, Carbamazepine CR, Carbamazepine XR, Carbidopa+Levodopa Er, Carisprodol, Celecoxib, Citalopram, Clobazam, Clonazepam, Clonidine Patch, Clonidine SR, Clopidogrel, Colchicine, Cyclobenzaprine ER, Cyclobenzaprine PO, Dalteparin sodium, Desvenlafaxine, Desvenlafaxine ER, Dexamfetamine, Dexmethylphenidate Hcl, Dexmethylphenidate Hcl LA, Diazepam, Diclofenacm, Diclofenac Gel, Diclofenac IR, Diclofenac IV, Diclofenac Potassium IR, Diclofenac Potassium XR, Diclofenac Transdermal, Disulfiram, Divalproex Sodium, Dolasetron Mesilate, Doxepin, Dronabinol, Droxidopa, Duloxetine, Eletriptan, Entacapone, Escitalopram oxalate, Eslicarbazepine Acetate, Esomeprazole/naproxen, Estradiol, Estrogen, Eszopiclone, Ethosuximide, Etodolac, Ezogabine, Febuxostat, Felbamate, Fenbufen, Fentanyl Citrate, Fentanyl Oral, Fentanyl Patch, Fentanyl SL, Flunisolide, Fluorouracil, Fluoxetine, Fluticasone propionate, Fluvoxamine Cr, Formoterol, Fosphenytoin, Frovatriptan, Gabapentin, Gabapentin ER, Granisetron ER, Guanfacine, Hydrocodone Bitartrate CR, Hydrocodone+Acetaminophen, hydrocortisone, Hydromorphone Hcl, Hydroxyzine, Hypericum Extract, Ibuprofen, Indometacin, Ketorolac, Lacosamide, Lamotrigine, Lamotrigine CDT, Lamotrigine ODT, Lamotrigine XR, Levetiracetam, Levetiracetam IR, Levetiracetam XR, Levomilnacipran, Levo salbutamol, Lidocaine Patch, Lidocaine/Tetracaine, Lisdexamfetamine, Lithium Carbonate, Lorazepam, Lorcaserin, Hydrochloride, Losartan, Loxapine, Meclizine, Meloxicam, Metaxalone, Methylphenidate, Methylphenidate Hydrochloride, Methylphenidate LA, Methylphenidate MR, Methylphenidate Patch, Milnacipran, Mirtazapine, Modafinil, Morphine, Morphine CR, Morphine ER, Nabilone, Nadolol, Naltrexone, Naproxen, Naratriptan, Nedocromil, Nefazodone, Nitroglycerin, Nitroglycerin Ointment, Olanzapine, Olanzapine IM, Olanzapine LA, Ondansetron, Ondansetron ODFS, Ondansetron ODT, Orlistat, Oxaprozin, Oxcarbazepine, Oxcarbazepine ER, Oxybutynin, Oxybutynin Gel, Oxycodone, Oxycodone+Acetominophen, Oxycodone Hydrochloride, Oxycodone IR, Oxymorphone, Oxymorphone ER, Palonosetro, Pamidronate, Paroxetine, Paroxetine Mesylate, Perampanel, Phentermine+Topiramate, Phentermine Hydrochloride, Phentolamine Mesylate, Pramipexole, Pramipexole-Er, Prasugrel, Prazepam, Prednisone, Pregabalin, Promethazine, Propofol, Quetiapine, Quetiapine Fumarate, Quetiapine Fumarate XR, Ramelteon, Rasagiline Mesylate, Remifentanil, Risperidone, Rivastigmine Tartrate, Rizatriptan, Ropinirole, Ropinirole XL, Ropivacaine, Rotigotine, Rufinamide, Salbutamol, Scopolamine, Selegiline, Selegiline ODT, Selegiline Transdermal, Sertraline, Sodium Oxybate, Strontium, Sufentanil-Ent, Sumatriptan Autoinjector, Sumatriptan Needle-free, Sumatriptan Succinate, Suvorexant, Tapentadol, Tapentadol ER, Tasimelteon, Temazepam, Testosterone, Tetracaine+Lidocaine, Theophylline, Tiagabine, Tiotropium, Tirofiban HcL, Tolcapone, Topiramate, Topiramate XR, Tramadol, Tramadol+Acetaminophen, Tramadol ER, Trazodone Cr, Triazolam, Trimipramine Maleate, Valproate Semisodium ER, Valproate Sodium, Venlafaxine, Venlafaxine ER, Vigabatrin, Vilazodone, Vortioxetine, Zaleplon, Zileuton, Ziprasidone, Zolmitriptan Oral, Zolmitriptan ZMT, Zolpidem, Zolpidem Spray, Zolpidem Tartrate CR, Zolpidem Tartrate Low dose SL, Zolpidem Tartrate SL, norethisterone acetate (NETA), enapril, ethinyl estradiol, insulin, memantine, methamphetamine, norelgestromine, pergolide, Ramipril, tecrine, timolol, tolterodine and Zonisamide.

Another aspect of the invention provides a method for delivering a bioactive agent with a two-part transdermal bioactive agent delivery system. In some embodiments, the method includes the steps of: connecting a reusable part of a delivery system to a disposable part of the delivery system; during the connecting step, compressing a spring (or other source of stored mechanical energy) extending from an agent reservoir of the disposable part to pressurize bioactive agent within the agent reservoir; actuating a valve driver in the reusable part to move a valve in the disposable part to a first position to transfer bioactive agent from the agent reservoir to a bolus chamber; and actuating the valve driver to move the valve to a second position to transfer bioactive agent from the bolus chamber to an agent outlet.

In embodiments in which the disposable part has a transdermal patch communicating with the agent outlet, the method includes the step of transferring bioactive agent from the bolus chamber to the transdermal patch. In some such embodiments in which the disposable part also has a solvent recovery chamber and the bioactive agent is dissolved in a solvent, the method may also include the step of receiving gaseous phase solvent from the from the transdermal patch in the solvent recovery chamber. In some such embodiments in which the disposable part also has a vapor permeable membrane, the receiving step may include the step of passing gaseous phase solvent through the vapor permeable membrane into the solvent recovery chamber. In some embodiments, the transdermal patch may include a polypropylene membrane with a plurality of pores having an average pore diameter of about 0.02 µm to about 0.10 µm, and the bioactive agent may be dissolved in a solution comprising alcohol and water in a ratio of alcohol to water of about 40:60 to about 60:40.

Some embodiments include the step of compressing a second spring extending from the bolus chamber to pressurize bioactive agent within the bolus chamber. In embodiments in which the system includes a piston movably disposed in the bolus chamber, the method may also include the step of moving the piston with the second spring to move bioactive agent from the bolus chamber to the agent outlet. In some embodiments, the second spring may be compressed during the connecting step. In some embodiments, the second spring may be compressed when bioactive agent is transferred from the agent reservoir into the bolus chamber.

In some embodiments, the valve rotates between 60° to 90°, inclusive, during the actuating steps. In embodiments in which the system has a piston disposed in the agent reservoir, the method may include the step of moving the piston with the spring to move bioactive agent from the agent reservoir to the bolus chamber.

In some embodiments, the method includes the step of, during or after the connecting step, providing an indication to a remote device that the disposable part has been connected to the reusable part, such as by wirelessly transmitting connection information to the remote device. Some embodiments also include the step of activating a switch during the connecting step to indicate that the disposable part has been connected to the reusable part. Some embodiments also include the step of closing a circuit during the connecting step by contacting a conductive element of the reusable part with a conductive element of the disposable part. At least one of the conductive elements may be a conductive elastomer.

Some embodiments include the step of programming delivery of the bioactive agent by actuating an input element on the reusable part. Some embodiments include the step of generating an indication that the disposable part needs to be replaced. In some such embodiments, the generating step includes the step of monitoring time elapsed after connecting the disposable part to the reusable part and providing the indication that the disposable part needs to be replaced after a predetermined time. Some embodiments include the step of sending information about operation of the delivery system from the reusable part to a remote device.

In some embodiments, the method includes the step of receiving an input from the user on the reusable part indicating that the user is experiencing a craving. In some such embodiments, the method also includes the step of wirelessly transmitting an indication of the input to a remote device. The method may also include the step of receiving a wireless signal indicating a psychological support in response to the input from the user indicating the craving. The psychological support may be displayed, e.g., on a display of the reusable part and/or on the remote device.

In any embodiments of the method, the bioactive agent may be selected from the group consisting of: Acamprosate, Acetaminophen, Acetaminophen+Oxycodone, Alevicyn SG, Alfentanil, Allopurinol, Almotriptan, Alprazolam, Alprazolam XR, Amitriptylinem, Amoxapine, Apomorphine, Aripiprazole, Armodafinil, Asenapine maleate, Atomoxetine, Azelastine HCL, Baclofen, Benzbromarone, Benzydamine, Brexpiprazole, Budesonide, Bupivacaine, Buprenorphine, Buprenorphine+Nalaxone, Bupropion, Bupropion Hydrobromide, Bupropion Hydrochloride, Bupropion SR, Bupropion XR, Buspirone, Cabergoline, Capsaicin, Carbamazepine CR, Carbamazepine XR, Carbidopa+Levodopa Er, Carisprodol, Celecoxib, Citalopram, Clobazam, Clonazepam, Clonidine Patch, Clonidine SR, Clopidogrel, Colchicine, Cyclobenzaprine ER, Cyclobenzaprine PO, Dalteparin sodium, Desvenlafaxine, Desvenlafaxine ER, Dexamfetamine, Dexmethylphenidate Hcl, Dexmethylphenidate Hcl LA, Diazepam, Diclofenacm, Diclofenac Gel, Diclofenac IR, Diclofenac IV, Diclofenac Potassium IR, Diclofenac Potassium XR, Diclofenac Transdermal, Disulfiram, Divalproex Sodium, Dolasetron Mesilate, Doxepin, Dronabinol, Droxidopa, Duloxetine, Eletriptan, Entacapone, Escitalopram oxalate, Eslicarbazepine Acetate, Esomeprazole/naproxen, Estradiol, Estrogen, Eszopiclone, Ethosuximide, Etodolac, Ezogabine, Febuxostat, Felbamate, Fenbufen, Fentanyl Citrate, Fentanyl Oral, Fentanyl Patch, Fentanyl SL, Flunisolide, Fluorouracil, Fluoxetine, Fluticasone propionate, Fluvoxamine Cr, Formoterol, Fosphenytoin, Frovatriptan, Gabapentin, Gabapentin ER, Granisetron ER, Guanfacine, Hydrocodone Bitartrate CR, Hydrocodone+Acetaminophen, hydrocortisone, Hydromorphone Hcl, Hydroxyzine, Hypericum Extract, Ibuprofen, Indometacin, Ketorolac, Lacosamide, Lamotrigine, Lamotrigine CDT, Lamotrigine ODT, Lamotrigine XR, Levetiracetam, Levetiracetam IR, Levetiracetam XR, Levomilnacipran, Levo salbutamol, Lidocaine Patch, Lidocaine/Tetracaine, Lisdexamfetamine, Lithium Carbonate, Lorazepam, Lorcaserin, Hydrochloride, Losartan, Loxapine, Meclizine, Meloxicam, Metaxalone, Methylphenidate, Methylphenidate Hydrochloride, Methylphenidate LA, Methylphenidate MR, Methylphenidate Patch, Milnacipran, Mirtazapine, Modafinil, Morphine, Morphine CR, Morphine ER, Nabilone, Nadolol, Naltrexone, Naproxen, Naratriptan, Nedocromil, Nefazodone, Nitroglycerin, Nitroglycerin Ointment, Olanzapine, Olanzapine IM, Olanzapine LA, Ondansetron, Ondansetron ODFS, Ondansetron ODT, Orlistat, Oxaprozin, Oxcarbazepine, Oxcarbazepine ER, Oxybutynin, Oxybutynin Gel, Oxycodone, Oxycodone+Acetominophen, Oxycodone Hydrochloride, Oxycodone IR, Oxymorphone, Oxymorphone ER, Palonosetro, Pamidronate, Paroxetine, Paroxetine Mesylate, Perampanel, Phentermine+Topiramate, Phentermine Hydrochloride, Phentolamine Mesylate, Pramipexole, Pramipexole-Er, Prasugrel, Prazepam, Prednisone, Pregabalin, Promethazine, Propofol, Quetiapine, Quetiapine Fumarate, Quetiapine Fumarate XR, Ramelteon, Rasagiline Mesylate, Remifentanil, Risperidone, Rivastigmine Tartrate, Rizatriptan, Ropinirole, Ropinirole XL, Ropivacaine, Rotigotine, Rufinamide, Salbutamol, Scopolamine, Selegiline, Selegiline ODT, Selegiline Transdermal, Sertraline, Sodium Oxybate, Strontium, Sufentanil-Ent, Sumatriptan Autoinjector, Sumatriptan Needle-free, Sumatriptan Succinate, Suvorexant, Tapentadol, Tapentadol ER, Tasimelteon, Temazepam, Testosterone, Tetracaine+Lidocaine, Theophylline, Tiagabine, Tiotropium, Tirofiban HcL, Tolcapone, Topiramate, Topiramate XR, Tramadol, Tramadol+Acetaminophen, Tramadol ER, Trazodone Cr, Triazolam, Trimipramine Maleate, Valproate Semisodium ER, Valproate Sodium, Venlafaxine, Venlafaxine ER, Vigabatrin, Vilazodone, Vortioxetine, Zaleplon, Zileuton, Ziprasidone, Zolmitriptan Oral, Zolmitriptan ZMT, Zolpidem, Zolpidem Spray, Zolpidem Tartrate CR, Zolpidem Tartrate Low dose SL, Zolpidem Tartrate SL, norethisterone acetate (NETA), enapril, ethinyl estradiol, insulin, memantine, methamphetamine, norelgestromine, pergolide, Ramipril, tecrine, timolol, tolterodine and Zonisamide.

Yet another aspect of the invention provides a bioactive agent delivery system having an agent reservoir containing a bioactive agent and a solvent solution of alcohol and water, wherein the solvent solution has a ratio of water to alcohol of about 40:60 to about 60:40; a membrane comprising polypropylene having a plurality of pores configured to contact a skin of the wearer of the bioactive agent delivery system; a vapor permeable membrane configured to allow vapor phase water and alcohol to pass through the vapor permeable membrane, the vapor permeable membrane in fluid communication with the membrane; and a delivery conduit extending from the agent reservoir and in fluid communication with the membrane, the delivery conduit configured to provide a dose of the bioactive agent and solvent solution from the agent reservoir to the membrane. In some embodiments, the membrane includes polypropylene having an average pore diameter of about 0.02 μm to about 0.10 μm.

Another aspect of the invention provides a bioactive agent delivery system including: an agent reservoir containing a bioactive agent and solvent solution; a membrane including polypropylene having a plurality of pores configured to contact a skin of the wearer of the bioactive agent delivery system, the plurality of pores having an average pore diameter of about 0.02 μm to about 0.10 μm; a vapor permeable membrane configured to allow vapor phase solvent solution to pass through the vapor permeable membrane, the vapor permeable membrane in fluid communication with the membrane; and a delivery conduit extending from the agent reservoir and in fluid communication with the membrane, the delivery conduit configured to provide a dose of the bioactive agent and solvent solution from the agent reservoir to the membrane. The solvent solution may include alcohol and water in a ratio of water to alcohol of about 40:60 to about 60:40.

Another aspect of the invention provides a bioactive agent delivery system including: an agent reservoir containing a bioactive agent and solvent solution including alcohol and water in a ratio of water to alcohol of about 40:60 to about 60:40; a membrane (such as, e.g., a transdermal membrane) including polypropylene having a plurality of pores configured to contact a skin of the wearer of the bioactive agent delivery system; a vapor permeable membrane configured to allow vapor phase water and alcohol to pass through the vapor permeable membrane, the vapor permeable membrane in fluid communication with the membrane; a delivery conduit extending from the agent reservoir and in fluid communication with the membrane, the delivery conduit configured to provide a dose of the bioactive agent and solvent solution from the agent reservoir to the membrane; and a control unit configured to control the bioactive agent delivery system to provide a dose of the bioactive agent and solvent solution from the agent reservoir to the membrane, the control unit further configured to provide a bio-synchronous drug delivery protocol to the wearer of the bioactive agent delivery system.

In some embodiments, the control unit is further configured to record a time of administration of the bioactive agent, a dosage amount of the bioactive agent, and a time at which dosing ceased. In some embodiments the bioactive agent delivery system may also include a wireless data transfer unit configured to wirelessly transmit the time of administration of the bioactive agent, the dosage amount of the bioactive agent, and the time at which dosing ceased to a remote network or device. In some embodiments, the bioactive agent delivery system may also include a sensor configured to determine when the agent reservoir is connected to the bioactive agent delivery system. In some embodiments, the control unit is configured to gather wearer data during the bio-synchronous drug delivery protocol and provide a psychological support based on the patient data.

In some embodiments, the solvent solution has a ratio of water to alcohol of about 45:55 to about 55:45; about 46:54 to about 54:46; about 47:53 to about 53:47; about 48:52 to about 52:48; or about 49:51 to about 51:49. In some embodiments, the solvent solution includes one or more of a: surfactant, excipient, or other component intended to enhance permeation or decrease skin sensitivity or skin reaction.

In some embodiments, the system also includes a disposable part comprising the agent reservoir, the agent reservoir having a piston movably disposed therein, a bolus chamber, the bolus chamber having a piston movably disposed therein, the volume of the bolus chamber being less than the volume of the agent reservoir, and a valve having a first position communicating the agent reservoir with the bolus chamber and a second position communicating the bolus chamber with the delivery conduit; and a reusable part including a valve driver, a power source and control electronics, the control electronics being adapted to control the valve driver to actuate the valve to deliver bioactive agent from the agent reservoir to the delivery conduit.

In some embodiments, the plurality of pores of the membrane have a non-circular cross section. In some embodiments, the plurality of pores of the membrane include longitudinal slits having a longitudinal cross section. In some embodiments, the membrane includes a surface area configured to contact the skin and the plurality of pores have an open surface area of about 25% to about 75% of the surface area of the membrane; about 35% to about 45% of the surface area of the membrane; or about 40% to about 42% of the surface area of the membrane.

In some embodiments, the alcohol is selected from the group consisting of: isopropanol, ethanol, and methanol.

Some embodiments of the system also include a solvent recovery chamber communicating with the membrane, the solvent recovery chamber being adapted to receive vapor phase solvent solution from the membrane. Some embodiments include a desiccant or an absorbent material disposed in the solvent recovery chamber. The vapor permeable membrane may have an average pore size of less than about 10 microns, and the pores may provide an open surface area of about 50% or less than the surface area of the vapor permeable membrane.

In some embodiments, the delivery conduit is configured to provide the dose of the bioactive agent and solvent solution to a space between the membrane and the vapor permeable membrane. In some embodiments, the delivery conduit is configured to provide the dose of the bioactive agent and solvent solution to a substantially centrally located section of the membrane, and in other embodiments, the delivery conduit is configured to provide the dose of the bioactive agent and solvent solution to an off-center section of the membrane.

In some embodiments, the membrane has a surface area that is less than about 15 cm$^2$, less than about 10 cm$^2$, or from about 15 cm$^2$ to about 30 cm$^2$.

In some embodiments, the delivery conduit is configured to move the dose of the bioactive agent and solvent solution from a first reservoir to the agent reservoir. The agent reservoir may have a volume of about 5 microliters to about 3 milliliters, or less than about 250 μL.

Some embodiments of the system include a delivery controller. In some such embodiments, the membrane has a surface area and the delivery controller and delivery conduit are configured to provide the dose with a volume of less than about 250 μL per 10 cm2 of surface area of the membrane. In some such embodiments, the delivery controller and delivery conduit are configured to provide the dose with a volume of between about 75 μL to about 250 μL per 10 cm$^2$ of surface area of the membrane. In some such embodiments, the delivery controller and delivery conduit are configured to provide the dose with a volume of less than about 150 μL per 10 cm$^2$ of surface area of the membrane.

In some embodiments, the bioactive agent includes nicotine. The concentration of nicotine in the solvent solution may be from about 0.5% to about 20% by volume.

In some embodiments, the system has a removable portion including the agent reservoir comprising the bioactive agent and the solvent solution. The removable portion may further include a bioactive agent source reservoir configured to provide the bioactive agent and solvent solution to the agent reservoir. In some embodiments, the bioactive agent source reservoir may have a volume of less than about 3 ml. Some embodiments of the system also include a sensor configured to determine when the removable portion is connected to the bioactive agent delivery system.

In some embodiments, the system also includes a control unit configured to control the bioactive agent delivery system to provide a dose of the bioactive agent and solvent solution from the agent reservoir to the membrane, the control unit further configured to provide a bio-synchronous drug delivery protocol to the wearer of the bioactive agent delivery system. The control unit may be further configured to record a time of administration of the bioactive agent, a dosage amount of the bioactive agent, and a time at which dosing ceased. In some embodiments, the system also includes a wireless data transfer unit configured to wirelessly transmit the time of administration of the bioactive agent, the dosage amount of the bioactive agent, and the time at which dosing ceased to a remote network or device. The control unit may also be configured to gather wearer data during the bio-synchronous drug delivery protocol and provide a psychological support based on the patient data.

In these embodiments, the bioactive agent delivery the bioactive agent may be selected from the group consisting of: Acamprosate, Acetaminophen, Acetaminophen+Oxycodone, Alevicyn SG, Alfentanil, Allopurinol, Almotriptan, Alprazolam, Alprazolam XR, Amitriptylinem, Amoxapine, Apomorphine, Aripiprazole, Armodafinil, Asenapine maleate, Atomoxetine, Azelastine HCL, Baclofen, Benzbromarone, Benzydamine, Brexpiprazole, Budesonide, Bupivacaine, Buprenorphine, Buprenorphine+Nalaxone, Bupropion, Bupropion Hydrobromide, Bupropion Hydrochloride, Bupropion SR, Bupropion XR, Buspirone, Cabergoline, Capsaicin, Carbamazepine CR, Carbamazepine XR, Carbidopa+Levodopa Er, Carisprodol, Celecoxib, Citalopram, Clobazam, Clonazepam, Clonidine Patch, Clonidine SR, Clopidogrel, Colchicine, Cyclobenzaprine ER, Cyclobenzaprine PO, Dalteparin sodium, Desvenlafaxine, Desvenlafaxine ER, Dexamfetamine, Dexmethylphenidate Hcl, Dexmethylphenidate Hcl LA, Diazepam, Diclofenacm, Diclofenac Gel, Diclofenac IR, Diclofenac IV, Diclofenac Potassium IR, Diclofenac Potassium XR, Diclofenac Transdermal, Disulfiram, Divalproex Sodium, Dolasetron Mesilate, Doxepin, Dronabinol, Droxidopa, Duloxetine, Eletriptan, Entacapone, Escitalopram oxalate, Eslicarbazepine Acetate, Esomeprazole/naproxen, Estradiol, Estrogen, Eszopiclone, Ethosuximide, Etodolac, Ezogabine, Febuxostat, Felbamate, Fenbufen, Fentanyl Citrate, Fentanyl Oral, Fentanyl Patch, Fentanyl SL, Flunisolide, Fluorouracil, Fluoxetine, Fluticasone propionate, Fluvoxamine Cr, Formoterol, Fosphenytoin, Frovatriptan, Gabapentin, Gabapentin ER, Granisetron ER, Guanfacine, Hydrocodone Bitartrate CR, Hydrocodone+Acetaminophen, hydrocortisone, Hydromorphone Hcl, Hydroxyzine, Hypericum Extract, Ibuprofen, Indometacin, Ketorolac, Lacosamide, Lamotrigine, Lamotrigine CDT, Lamotrigine ODT, Lamotrigine XR, Levetiracetam, Levetiracetam IR, Levetiracetam XR, Levomilnacipran, Levosalbutamol, Lidocaine Patch, Lidocaine/Tetracaine, Lisdexamfetamine, Lithium Carbonate, Lorazepam, Lorcaserin, Hydrochloride, Losartan, Loxapine, Meclizine, Meloxicam, Metaxalone, Methylphenidate, Methylphenidate Hydrochloride, Methylphenidate LA, Methylphenidate MR, Methylphenidate Patch, Milnacipran, Mirtazapine, Modafinil, Morphine, Morphine CR, Morphine ER, Nabilone, Nadolol, Naltrexone, Naproxen, Naratriptan, Nedocromil, Nefazodone, Nitroglycerin, Nitroglycerin Ointment, Olanzapine, Olanzapine IM, Olanzapine LA, Ondansetron, Ondansetron ODFS, Ondansetron ODT, Orlistat, Oxaprozin, Oxcarbazepine, Oxcarbazepine ER, Oxybutynin, Oxybutynin Gel, Oxycodone, Oxycodone+Acetaminophen, Oxycodone Hydrochloride, Oxycodone IR, Oxymorphone, Oxymorphone ER, Palonosetro, Pamidronate, Paroxetine, Paroxetine Mesylate, Perampanel, Phentermine+Topiramate, Phentermine Hydrochloride, Phentolamine Mesylate, Pramipexole, Pramipexole-Er, Prasugrel, Prazepam, Prednisone, Pregabalin, Promethazine, Propofol, Quetiapine, Quetiapine Fumarate, Quetiapine Fumarate XR, Rameleton, Rasagiline Mesylate, Remifentanil, Risperidone, Rivastigmine Tartrate, Rizatriptan, Ropinirole, Ropinirole XL, Ropivacaine, Rotigotine, Rufinamide, Salbutamol, Scopolamine, Selegiline, Selegiline ODT, Selegiline Transdermal, Sertraline, Sodium Oxybate, Strontium, Sufentanil-Ent, Sumatriptan Autoinjector, Sumatriptan Needle-free, Sumatriptan Succinate, Suvorexant, Tapentadol, Tapentadol ER, Tasimelteon, Temazepam, Testosterone, Tetracaine+Lidocaine, Theophylline, Tiagabine, Tiotropium, Tirofiban HcL, Tolcapone, Topiramate, Topiramate XR, Tramadol, Tramadol+Acetaminophen, Tramadol ER, Trazodone Cr, Triazolam, Trimipramine Maleate, Valproate Semisodium ER, Valproate Sodium, Venlafaxine, Venlafaxine ER, Vigabatrin, Vilazodone, Vortioxetine, Zaleplon, Zileuton, Ziprasidone, Zolmitriptan Oral, Zolmitriptan ZMT, Zolpidem, Zolpidem Spray, Zolpidem Tartrate CR, Zolpidem Tartrate Low dose SL, Zolpidem Tartrate SL, norethisterone acetate (NETA), enapril, ethinyl estradiol, insulin, memantine, methamphetamine, norelgestromine, pergolide, Ramipril, tecrine, timolol, tolterodine and Zonisamide.

Another aspect of the invention provides a method for providing a bioactive agent. In some embodiments the method includes the following steps: moving a bioactive agent in a solvent solution comprising alcohol and water from an agent reservoir of a drug delivery device into contact with a membrane of the drug delivery device, wherein the solvent solution has a ratio of water to alcohol of about 40:60 to about 60:40, the drug delivery device in contact with a skin of the wearer, the membrane comprising polypropylene having a plurality of pores configured to contact the skin of the wearer; passing bioactive agent through the plurality of pores of the membrane into contact with the skin of the wearer; and passing vapor phase solvent solution through a vapor permeable membrane of the drug delivery device while preventing liquid phase solvent solution from passing through the vapor permeable membrane.

In some embodiments, the step of passing vapor phase solvent solution includes the step of passing vapor phase solvent solution through the vapor permeable membrane into a solvent recovery chamber of the drug delivery device. The method may also include the step of collecting the solvent solution with a desiccant and/or absorbent material disposed in the solvent recovery chamber.

In some embodiments, the step of moving the bioactive agent in the solvent solution includes providing the dose of the bioactive agent and solvent solution to a space between the membrane and the vapor permeable membrane. The dose of the bioactive agent and solvent solution may be provided to a substantially centrally located section of the membrane or to an off-center section of the membrane. In some embodiments, dose of the bioactive agent and solvent solution is provided through multiple orifices onto the membrane. In some embodiments, the membrane has a surface area that is less than about 15 $cm^2$, between about 15 $cm^2$ and 30 $cm^2$, or less than about 10 $cm^2$.

In some embodiments, the method includes the step of moving the dose of the bioactive agent and solvent solution from a first reservoir of the drug delivery device to the agent reservoir. In some embodiments, the dose has a volume of less than about 250 μL per 10 $cm^2$ of surface area of the membrane, between about 75 μL to about 250 μL per 10 $cm^2$ of surface area of the membrane, or less than about 150 μL per 10 $cm^2$ of surface area of the membrane. In some embodiments, the membrane has an average pore diameter of about 0.02 μm to about 0.10 μm, and passing bioactive agent includes passing bioactive agent through the plurality of pores having the average pore diameter of about 0.02 μm to about 0.10 μm In some embodiments, the solvent solution has a ratio of water to alcohol of about 45:55 to about 55:45, about 46:54 to about 54:46, about 47:53 to about 53:47, about 48:52 to about 52:48, or about 49:51 to about 51:49.

In some embodiments, the membrane includes a surface area configured to contact the skin and the plurality of pores have an open surface area of about 35% to about 65% of the surface area of the membrane, about 35% to about 45% of the surface area of the membrane, or about 40% to about 42% of the surface area of the membrane.

In some embodiments, the alcohol is selected from the group consisting of: isopropanol, ethanol, and methanol. In some embodiments, the agent reservoir has a volume of less than about 3 ml or less than about 250 μL.

Some embodiments include the step of moving the bioactive agent in the solvent solution from the agent reservoir into contact with the membrane and passing bioactive agent through the plurality of pores of the membrane into contact with the skin of the wearer to provide a bio-synchronous drug delivery protocol to the wearer.

Some embodiments include the step of gathering patient data of the wearer, such as patient emotional state data, e.g., cravings. The method may also include the step of providing a psychological support based on the patient data.

Some embodiments include the step of analyzing wearer compliance by one or more of determining whether the drug delivery device was removed, a treatment in a drug delivery protocol was missed, or if the drug delivery protocol was interrupted.

Some embodiments include the step of treating ulcerative colitis or Parkinson's disease by providing the bioactive agent to the wearer. In any of the embodiments, the bioactive agent may be selected from the group consisting of: nicotine, Acamprosate, Acetaminophen, Acetaminophen+Oxycodone, Alevicyn SG, Alfentanil, Allopurinol, Almotriptan, Alprazolam, Alprazolam XR, Amitriptylinem, Amoxapine, Apomorphine, Aripiprazole, Armodafinil, Asenapine maleate, Atomoxetine, Azelastine HCL, Baclofen, Benzbromarone, Benzydamine, Brexpiprazole, Budesonide, Bupivacaine, Buprenorphine, Buprenorphine+Nalaxone, Bupropion, Bupropion Hydrobromide, Bupropion Hydrochloride, Bupropion SR, Bupropion XR, Buspirone, Cabergoline, Capsaicin, Carbamazepine CR, Carbamazepine XR, Carbidopa+Levodopa Er, Carisprodol, Celecoxib, Citalopram, Clobazam, Clonazepam, Clonidine Patch, Clonidine SR, Clopidogrel, Colchicine, Cyclobenzaprine ER, Cyclobenzaprine PO, Dalteparin sodium, Desvenlafaxine, Desvenlafaxine ER, Dexamfetamine, Dexmethylphenidate Hcl, Dexmethylphenidate Hcl LA, Diazepam, Diclofenacm, Diclofenac Gel, Diclofenac IR, Diclofenac IV, Diclofenac Potassium IR, Diclofenac Potassium XR, Diclofenac Transdermal, Disulfiram, Divalproex Sodium, Dolasetron Mesilate, Doxepin, Dronabinol, Droxidopa, Duloxetine, Eletriptan, Entacapone, Escitalopram oxalate, Eslicarbazepine Acetate, Esomeprazole/naproxen, Estradiol, Estrogen, Eszopiclone, Ethosuximide, Etodolac, Ezogabine, Febuxostat, Felbamate, Fenbufen, Fentanyl Citrate, Fentanyl Oral, Fentanyl Patch, Fentanyl SL, Flunisolide, Fluorouracil, Fluoxetine, Fluticasone propionate, Fluvoxamine Cr, Formoterol, Fosphenytoin, Frovatriptan, Gabapentin, Gabapentin ER, Granisetron ER, Guanfacine, Hydrocodone Bitartrate CR, Hydrocodone+Acetaminophen, hydrocortisone, Hydromorphone Hcl, Hydroxyzine, Hypericum Extract, Ibuprofen, Indometacin, Ketorolac, Lacosamide, Lamotrigine, Lamotrigine CDT, Lamotrigine ODT, Lamotrigine XR, Levetiracetam, Levetiracetam IR, Levetiracetam XR, Levomilnacipran, Levosalbutamol, Lidocaine Patch, Lidocaine/Tetracaine, Lisdexamfetamine, Lithium Carbonate, Lorazepam, Lorcaserin, Hydrochloride, Losartan, Loxapine, Meclizine, Meloxicam, Metaxalone, Methylphenidate, Methylphenidate Hydrochloride, Methylphenidate LA, Methylphenidate MR, Methylphenidate Patch, Milnacipran, Mirtazapine, Modafinil, Morphine, Morphine CR, Morphine ER, Nabilone, Nadolol, Naltrexone, Naproxen, Naratriptan, Nedocromil, Nefazodone, Nitroglycerin, Nitroglycerin Ointment, Olanzapine, Olanzapine IM, Olanzapine LA, Ondansetron, Ondansetron ODFS, Ondansetron ODT, Orlistat, Oxaprozin, Oxcarbazepine, Oxcarbazepine ER, Oxybutynin, Oxybutynin Gel, Oxycodone, Oxycodone+Acetaminophen, Oxycodone Hydrochloride, Oxycodone IR, Oxymorphone, Oxymorphone ER, Palonosetro, Pamidronate, Paroxetine, Paroxetine Mesylate, Perampanel, Phentermine+Topiramate, Phentermine Hydrochloride, Phentolamine Mesylate, Pramipexole, Pramipexole-Er, Prasugrel, Prazepam, Prednisone, Pregabalin, Promethazine, Propofol, Quetiapine, Quetiapine Fumarate, Quetiapine Fumarate XR, Ramelteon, Rasagiline Mesylate, Remifentanil, Risperidone, Rivastigmine Tartrate, Rizatriptan, Ropinirole, Ropinirole XL, Ropivacaine, Rotigotine, Rufinamide, Salbutamol, Scopolamine, Selegiline, Selegiline ODT, Selegiline Transdermal, Sertraline, Sodium Oxybate, Strontium, Sufentanil-Ent, Sumatriptan Autoinjector, Sumatriptan Needle-free, Sumatriptan Succinate, Suvorexant, Tapentadol, Tapentadol ER, Tasimelteon, Temazepam, Testosterone, Tetracaine+Lidocaine, Theophylline, Tiagabine, Tiotropium, Tirofiban HcL, Tolcapone, Topiramate, Topiramate XR, Tramadol, Tramadol+Acetaminophen, Tramadol ER, Trazodone Cr, Triazolam, Trimipramine Maleate, Valproate Semisodium ER, Valproate Sodium, Venlafaxine, Venlafaxine ER, Vigabatrin, Vilazodone, Vortioxetine, Zaleplon, Zileuton, Ziprasidone, Zolmitriptan Oral, Zolmitriptan ZMT, Zolpidem, Zolpidem Spray, Zolpidem Tartrate CR, Zolpidem Tartrate Low dose SL, Zolpidem Tartrate SL, norethisterone acetate (NETA), enapril, ethinyl estradiol, insulin, memantine, methamphetamine, norelgestromine, pergolide, Ramipril, tecrine, timolol, tolterodine and Zonisamide.

Still another aspect of the invention provides a method of using a bioactive agent delivery device, including the following steps: receiving an input from a button on the bioactive agent delivery device from a wearer of the device indicating a craving; transmitting a signal indicating the craving wirelessly over a network or to another device; and providing a supportive message to the wearer in response to the transmitted signal. Some embodiments also include the step of providing the supportive message by an e-mail, text message, or smartphone notification. The method may also include the step of sending a notification of the craving to a remote device, such as that of a sponsor or other contact provided by the wearer.

Some embodiments include the step of engaging a disposable part and a reusable part of the bioactive agent delivery device. The method may also include the step of providing an indication that the disposable part and the reusable part have been engaged and, optionally, wirelessly transmitting a signal indicating engagement of the disposable part and the reusable part a computer or other remote device using, e.g., a Bluetooth protocol.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-9E show an embodiment of a two-part bioactive agent delivery system according to the invention.

FIG. 11A is a perspective view of the reusable portion.

FIG. 11B is a perspective view of the reusable portion with internal components shown in phantom. FIG. 11C is a side sectional view of the reusable portion along the line C-C in FIG. 11B.

FIGS. 14A and 14C are exploded top perspective views of the transdermal patch and a solvent recovery mechanism, and FIG. 14B is an exploded bottom perspective view of the transdermal patch and a solvent recovery mechanism. FIG. 14D illustrates assembly of the transdermal patch and a solvent recovery mechanism.

FIGS. 15A-15E show an embodiment of a disposable portion for use with a two-part bioactive agent delivery system. FIG. 15A is a plan view. FIG. 15B is an exploded perspective view. FIGS. 15C-E are perspective views of the manifold of the disposable portion.

FIG. 16A is a plan view. FIG. 16B is an exploded perspective view.

FIGS. 17A-17E show another embodiment of a disposable portion for use with a two-part transdermal bioactive agent delivery system. FIG. 17A is a plan view. FIG. 17B is an exploded perspective view. FIGS. 17C and 17D are top and bottom views, respectively, of components of the disposable portion. FIG. 17E is an exploded perspective view of components of the disposable portion.

FIGS. 18A-18C show yet another embodiment of a disposable portion for use with a two-part transdermal bioactive agent delivery system. FIG. 18A is a plan view. FIG. 18B is a sectional view. FIG. 18C is an exploded perspective view.

FIGS. 19A-19F show another embodiment of a disposable portion for use with a two-part transdermal bioactive agent delivery system. FIG. 19A is a plan view. FIG. 19B is a plan view of a desiccant housing of the disposable portion. FIG. 19C is an exploded perspective view. FIGS. 19D and 19E are plan views of a structural support. FIG. 19F is an exploded perspective view of parts of the disposable portion.

FIGS. 20A-20E show different views of a yet another embodiment of a two-part transdermal bioactive agent delivery system. FIG. 20A is a perspective view of the system. FIGS. 20B and 20C are exploded perspective views of the two main parts of the system. FIGS. 20D and 20E are sectional views of the reusable part of the system.

FIGS. 21A-21F show another embodiment of a two-part transdermal bioactive agent delivery system. FIG. 21A is a perspective view of the system. FIG. 21B is an exploded perspective view of the system. FIGS. 21C and 21D show cutaway perspective views of the system. FIGS. 21E and 21F show sectional views.

FIG. 22A shows an exploded perspective view of a valve core and valve driver for rotating the core.

FIG. 22B shows a close-up view of the valve driver shown in FIG. 22A.

FIG. 22C shows an exploded cross-sectional view of the valve core and valve driver shown in FIG. 22A.

FIG. 22D shows a perspective view of another valve driver that can be used with the valve core shown in FIGS. 22A and 22C.

FIG. 28A-F are exploded perspective views of portions of the system of FIG. 26A. FIGS. 28A-C show details of a reusable part of the system. FIGS. 28D-F show details of a disposable part of the system.

DETAILED DESCRIPTION

Figure 1:
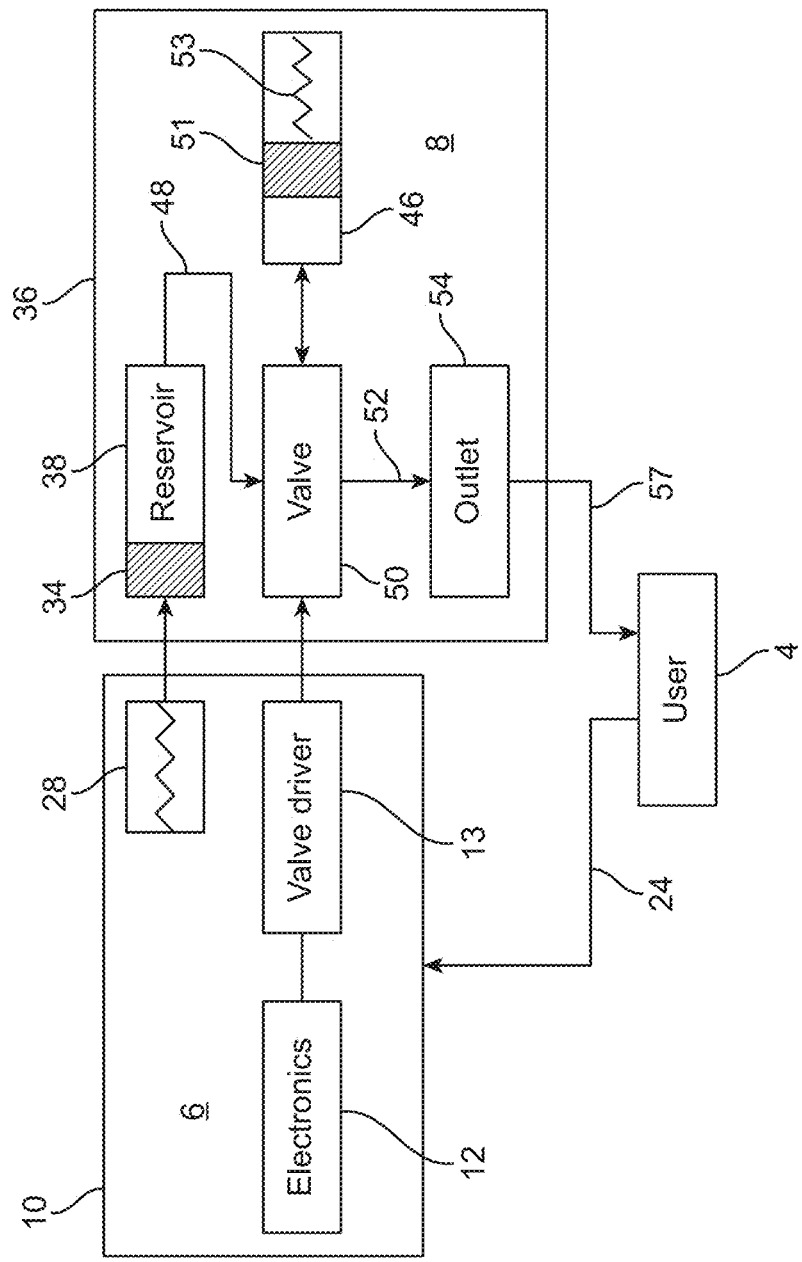
FIG. 1 is a block diagram of a two-part bioactive agent delivery system according to one embodiment of the invention.

Described herein are systems, devices, and methods for delivery of a drug or other bioactive agent to a user in need. A bioactive agent delivery system as described herein may be useful for delivering a bioactive agent to a user for addiction or dependency management or prevention such as for a drug addiction, for diabetes or other disease management or prevention, for pain management or prevention or for another therapeutic or prophylactic purpose. The systems, devices, and methods may be especially useful for delivering multiple doses of a drug or other bioactive agent to a user over time with a safe, inexpensive, convenient, and easy-to-use system that minimizes risk of a drug or other bioactive agent overdose. A bioactive agent delivery system as described herein may be configured to store multiple doses of a bioactive agent and to deliver multiple doses (also referred to as boluses) of the bioactive agent to a user over time.

A bioactive agent delivery system may reproducibly deliver a fixed amount of a bioactive agent to a user, such as to a user's skin, to have a therapeutic or prophylactic effect on the user. In some variations, a bioactive agent delivery system may be configured to be wearable and to deliver a fixed amount of a bioactive agent to a user's skin in a relatively thin, quiet, easy to use, convenient, electronically controlled system. Such a bioactive agent delivery system may be configured to be attached to a user's body (such as for a day or shorter or longer), connect with a user's skin, and deliver a bioactive agent across the user's skin.

The systems described herein can include a transdermal membrane that contacts the wearer's skin. A drug or other bioactive agent and solvent solution can be delivered in a controlled amount to the transdermal membrane. The transdermal membrane can be configured to minimize permeation of the solvent solution while permitting diffusion of the drug or other bioactive agent across the membrane and into contact with the skin. The solvent solution can be removed through a vapor permeable membrane. The systems described herein can efficiently deliver substantially all of the drug or other bioactive agent across the transdermal membrane into contact with the wearer's skin.

The systems described herein can more efficiently deliver a drug or other bioactive agent versus prior art drug delivery systems, such as patches. Patches deliver drugs or bioactive agents based on diffusion and typically have a large amount of residual drug left in the patch after use. The residual drug left in the patch can present a high safety risk for children and animals. For example, children can accidentally think that the patch is candy and chew or eat the patch. When a drug or bioactive agent that has a toxicity to small children is used then the patches can present a poisoning hazard. The systems described herein deliver substantially all of the drug or bioactive agent that is delivered to the transdermal membrane. Thus, there is minimal poisoning risk from residual drug left on the transdermal membrane. Any drug and solvent remaining within the device, such as present in the drug reservoir(s) of the device is protected and difficult to access for children and animals.

In some embodiments, the transdermal membrane can be designed such that the drug or bioactive agent only diffuses when the transdermal membrane is in contact with skin. In some cases the drug or bioactive agent does not pass through the transdermal membrane unless the transdermal membrane is in contact with a skin of the wearer.

The composition of the solvent can also be designed and selected to optimize the diffusion of the drug or bioactive agent across the transdermal membrane. The composition of the solvent can also be chosen in combination with the transdermal membrane to achieve the desired drug or bioactive agent delivery rate.

A bioactive agent delivery system according to this invention may be a two-part system: a reusable part (also referred to as a durable part) and a disposable part (also called a replaceable or disposable part) that can be removably attached to the reusable part so that the reusable part can control the disposable part. The disposable part may include bioactive agent and system parts that come into contact with bioactive agent, and the reusable part may not contain bioactive agent or system parts that come into contact with bioactive agent. In this way, a reusable part can be used with a plurality of disposable parts over time that can provide a fresh supply of bioactive agent to the user as needed to replace a bioactive agent supply that has been used up or expired, while reusing components that are still usable to save money and materials and minimize waste.

Bioactive agent delivery systems are disclosed herein. The systems can include an agent reservoir comprising a bioactive agent and a solvent solution, a membrane comprising polypropylene having a plurality of pores configured to contact a skin of the wearer of the bioactive agent delivery system, a vapor permeable membrane configured to allow vapor phase solvent solution to pass through the vapor permeable membrane, and a delivery conduit extending from the agent reservoir and in fluid communication with the membrane. The delivery conduit can be configured to provide a dose of the bioactive agent and solvent solution from the agent reservoir to the membrane. The membrane contacting the skin can be a transdermal membrane.

In some embodiments a disposable part may include a solvent recovery mechanism, such as an absorbent or a desiccant, to remove solvent in which the bioactive agent is dissolved, and thus spent absorbent can be readily replaced when a disposable part is replaced with new disposable part containing fresh absorbent. Although a reusable part and a disposable part of a bioactive agent delivery system as described herein are generally configured to work with each other, either may be additionally or instead be used separately or as part of a different system, such as with a different disposable part or with a different reusable part.

A used disposable part may be readily removable from the reusable part, and a new disposable part attached to the reusable part for further use by a user. A disposable part may contain system parts that come into contact with bioactive agent, such as a reservoir containing a plurality of bioactive agent doses, a bolus chamber (also called a dosing chamber) for measuring a dose of bioactive agent from the reservoir and an outlet for delivering the bioactive agent from the bolus chamber to a transdermal patch or other user delivery component.

Bioactive delivery system embodiments may have more than two parts, of course, without departing from the scope of the invention. Some embodiments may also integrate all device components into a single part.

A bioactive agent delivery system may be configured so that there is no direct pathway from the reservoir to the outlet to minimize, or even eliminate, risk of accidental bioactive agent delivery or overdose. As indicated above, a system may be configured to provide multiple doses of bioactive agent to a user (e.g., from a single disposable part), and the bioactive agent delivery system may include a valve configured to prevent a direct pathway between a reservoir containing a plurality of bioactive doses and the user to minimize the risk of bioactive agent overdose.

A bioactive agent delivery system as described herein may be useful for delivering a bioactive agent to any part on or in a user's body. In some particular variations, a bioactive agent delivery system as described herein may be especially useful for delivering a bioactive agent topically or transdermally to or through a user's skin to a skin layer or bloodstream. Effective topical or transdermally delivery may be aided by use of a skin delivery membrane such as described herein for transferring active agent across the skin that is fully or sufficiently wetted to effectively transfer a dose of bioactive agent to a user's skin. In some variations, a bioactive agent delivery system may be electronically controlled, programmable, portable, and wearable.

A disposable part may be sufficient or insufficient for an entire treatment regimen. A disposable part may contain a sufficient amount of bioactive agent for an entire treatment regimen (e.g., for all required treatments) or may contain only a limited number of doses that provides a partial treatment. Additional amounts of bioactive agent can be delivered to the user by replacing a spent disposable part in the reusable part with a fresh disposable part.

Having a bioactive agent delivery system with a disposable part may allow the system to be relatively small or relatively flat and easy to wear. For example, a system may be relatively small or flat since a disposable part needs only contain a limited amount of bioactive agent and/or (and as explained in more detail below) a reusable part needs only be imparted with sufficient force or power for a limited number of dose deliveries before being recharged. In some examples, a system may be less than about 20 mm, less than about 16 mm, less than about 15 mm, less than about 14 mm, less than about 13 mm, less than about 12 mm, less than about 11 mm or less than about 10 mm in thickness and may be less than 40 mm, less than 35 mm in length or width, or less than 30 mm in length or width.

In some examples, a system may have less than 1500 mm² or less than 1000 mm² top (or bottom) surface area. "Bottom" in this context generally refers the part(s) of the system closest to a user. If a system includes a transdermal patch, bottom may refer to the transdermal patch and to the skin delivery member of a transdermal patch. A surface area of one side of a skin delivery member may be at least 100 mm², at least 500 mm², at least 1500 mm², at least 2000 mm², at least 2500 mm² at least 3000 mm² or less than or between any of these numbers (such as at least 500 mm² and less than 2000 mm²).

A surface of a bioactive agent delivery device, such as skin delivery member may have any shape, such as circular, ovoid, rectangular, square and may be contoured (or able to be contoured) to better fit a user's skin. Additionally, a disposable part that carries a limited number of doses may allow a user to use the doses before oxidation or other breakdown processes renders the bioactive agent unsafe or unusable.

As mentioned above, tobacco contains toxic substances that damage a person's health. Tobacco also contains nicotine and nicotine is highly addictive. In some particular examples, a bioactive agent delivery system may be useful for delivering a bioactive agent to help a person overcome a nicotine addiction and to stop using tobacco (e.g., to stop smoking, stop chewing tobacco, etc.). A person who is trying to stop smoking or stop using another form of nicotine usually experiences highly unpleasant withdrawal symptoms (e.g., anxiety, cravings, depression, headache, irritability, nausea, etc.). These symptoms can be severe or long lasting. If not addressed, withdrawal symptoms can derail an attempt to quit smoking and a person may continue smoking.

To overcome a nicotine addiction and manage (e.g., minimize or eliminate) withdrawal effects, a user may be gradually weaned from nicotine by receiving small amounts of therapeutic nicotine (which amounts may get smaller over time) to reduce symptoms and then eliminating the therapeutic nicotine altogether. Cravings for smoking a cigarette (or having another tobacco or other nicotine containing product) often come and go over the course of a day and over time (from day to day, week to week, etc.). Cravings may be especially strong the first two-to-three days after giving up smoking.

Some cravings depend on a person's normal daily rhythms and other activities in their lives. For example, many people have cravings for a cigarette with events that happen daily such as when waking up, after eating a meal, etc. These cravings may happen at the same or at different times on different days. Many people also have cravings due to other events in their lives such as during a stressful event (e.g., on-the-job stress, an argument with a person, a traffic accident etc.) that are different from day to day and the timing of these events may be hard to predict.

Similarly, pain, whether chronic or acute, often varies during the day or from day to day. A migraine and other headache may be worse at one time of the day (such as in the morning) than at another time of day or may come on unexpectedly. A drug or other bioactive agent may be needed at certain times of day, but may or may not be needed at other times. A system as described herein may be configured to provide a bioactive agent when it is needed by a user. A system may be configured to provide a bioactive agent to a user at a pre-programmed time or at an on-demand time.

To reduce or eliminate withdrawal symptoms (e.g., cravings) and help a person stop smoking generally requires multiple active agent doses over the course of a day on multiple days (weeks or months). A bioactive agent delivery system as described herein may be configured to deliver multiple doses (also referred to as boluses) during the course of a day and/or for multiple days. A bioactive agent delivery system may be especially useful to help a user control cravings or other withdrawal symptoms by delivering a bioactive agent dose (e.g., a dose of nicotine) especially during (or before) a time of day when cravings or withdrawal symptoms are normally most troublesome (such as delivering a dose during the night to prevent cravings upon waking).

In some embodiments of the invention, a reservoir containing the bioactive agent within disposable part is pressurized when, or after, the disposable part connects to the reusable part, and delivery of the bioactive agent is controlled by the reusable part by controlling the outlet from the reservoir. FIG. 1 shows a block diagram of one such bioactive agent delivery system for delivering multiple doses of a drug or other bioactive agent to a user in an inexpensive and easy-to-use system that reduces risk of accidental bioactive agent delivery or overdose.

As shown in FIG. 1, a two-part bioactive agent delivery system 2 with reusable part 6 and disposable part 8 work together to deliver a plurality of drug or other bioactive agent doses to user 4. A two-part delivery system has two parts that can be connected for use together, and then disconnected from each other; the reusable part may thereafter be used with another disposable part. Such a system may improve safety or convenience by replacing components that come into contact with bioactive agent, replenishing a bioactive agent supply, supplying a new supply of absorbent for solvent removal, etc. Such a system may reduce cost by reusing some components, such as some of the components that do not come into contact with bioactive agent.

FIG. 1 shows reusable part 6 with housing 10, spring 28, electronics apparatus 12, and valve driver 13. Housing 10 may wholly but will generally at least partially contain, cover, insulate, or protect other components such as electronics apparatus 12, etc., in reusable part 6. It may also wholly or at least partially contain, cover, insulate, or protect components in disposable part 8 when disposable part 8 is connected with reusable part 6 for use.

Disposable part 8 generally contains components that come into contact with bioactive agent, although it may contain additional components as well. Disposable part 8 and reusable part 6 are configured to connect or otherwise attach to each other in an operative manner. In some embodiments, housing 10 of reusable part 6 and/or housing 36 of disposable part 8 may have connectors such as resilient snaps, magnets, detents, etc. to reversibly attach the two housings to each other. In some embodiments, spring 28 extends from reusable part 6. When reusable part 6 is connected to disposable part 8, spring 28 engages movable piston 34 in disposable part 8 (or an intervening element between piston 34 and spring 28) to apply a force to movable piston 34, which causes piston 34 to apply pressure to the bioactive agent within reservoir 38. In other embodiments, spring 28 may be located in the disposable part 8 and would be compressed and loaded when the reusable part 6 is connected to disposable part 8.

A reservoir 38 in disposable part 8 contains multiple doses of bioactive agent for delivery to the user, and reusable part 6 controls dose delivery from the reservoir to the user 4. In this embodiment, reservoir 38 is pressurized when, or after, the disposable part 8 connects to the reusable part. Delivery of the bioactive agent from the pressurized reservoir 38 is controlled by controlling valve 50 at the outlet from reservoir 38. Because it does not use a pump, the system of this embodiment may be more quiet, less expensive, less weight, etc. than a system with a pump and may be more acceptable to a user.

Spring 28 may include a battery spring or coil spring or another spring or component, as long as it can store energy and act to pressurize reservoir 38 in disposable part 8. In other embodiments, spring 28 may be an air spring, an elastomer, a foam, another fluid spring, a gas spring, another highly compressible material(s), a leaf spring, a sponge, or another member that stores energy (e.g., mechanical or potential energy).

Although referred to as a spring, a function of a spring and its related components may be performed by another component such as an induction system, a magnetic system or another system and a bioactive agent delivery system may or may not have a first (or spring or other spring) as long as it provides or stores potential energy that can be turned into kinetic energy. Spring 28 can be any component that can be primed (e.g., compressed against housing 10 via force 30) to store elastic potential energy.

As indicated above, pressurized bioactive agent can be passively delivered to a user from disposable part 8 in a plurality of separate doses. The first (or second or other) spring may be configured to store sufficient potential energy to deliver a limited number of doses such as 1, 2, 3, 4, 5, 6, doses (plus a small amount of reserve energy) and thus may be relatively small to reduce device size and/or weight. Any spring with a suitable spring constant or maximum spring insertion force that stores sufficient elastic potential energy to drive appropriate piston movement for bioactive agent pressurization (and multiple dose delivery) can be used.

For example, spring 28 may be a spring with a maximum spring insertion force of less than 30 lbf, less than 20 lbf, less than 15 lbf, less than 10 lbf, less than 5 lbf (or in between any of these amounts, such as between 10 lbf and 15 lbf, between 9 lbf and 13 lbf, etc.). In some examples spring 28 is a battery spring or a coil spring with a maximum spring insertion force between 8 lbf and 15 lbf, between 10 lbf and 15 lbf, between 11 lbf and 13 lbf, etc.). Spring 28 is generally configured to provide sufficient force to move the bioactive agent (e.g., the multiple doses of bioactive agent) through the disposable part to an outlet or user. In some examples, spring 28 may be configured to provide at least 10 N, at least 20 N, at least 30 N, at least 40 N, at least 50 N, at least 75 N, at least 100 N, at least 125 N, at least 150 N, at least 200 N, at least 250 N or less than any of these amounts (e.g., less than 250 N, less than 200 N, etc.) or anything in between these amounts. In some examples, spring 28 may provide from 30 N and 50 N, from 50 N to 75 N, from 75 N to 100 N, from 100 to 150 N. For example, spring 28 may be a conical spring providing around 50 N or around 100 N, etc. Spring 28 may be a conical spring or tapered spring such as a battery spring or another spring sufficiently small to fit into the bioactive agent delivery system and provide appropriate force for pressurizing the reservoir or bioactive agent. In some examples, a compressed spring may be shorter than 500 mm, 400 mm, 300 mm, 200 mm, 150 mm, 100 mm, 90 mm, 80 mm, 70 mm, 60 mm, 50 mm, 40 mm, 30 mm, or 20 mm or least 10 mm, 20 mm, 30 mm, 40 mm, 50 mm, 60 mm, 70 mm, 80 mm, 90 mm, 100 mm, 110 mm, 150 mm, 200 mm, 300 mm, or 400 mm or between any of these sizes (e.g., longer than 50 mm and shorter than 120 mm). Spring 28 may be short enough to fit into a relatively small, wearable bioactive agent delivery system configured to hold and deliver a limited number of bioactive agent doses (such as 5 or fewer doses of less than 200 µl each), a spring may be at least 10 mm, at least 20 mm, at least 30 mm, at least 40 mm, at least 50 mm, at least 60 mm, at least 70 mm, at least 80 mm, at least 90 mm, at least 100 mm, at least 110 mm, at least 150 mm and/or less than 150 mm (e.g., less than 100 mm, less than 90 mm, less than 80 mm, less than 70 mm, less than 60 mm, less than 50 mm, less than 40 mm, less than 30 mm, or less than 20 mm) in length. A spring may have any cross-sectional diameter (e.g., on a first end, on a second end, or between the first end and the second end or in the middle of the spring), that provides appropriate force to another component(s) in the bioactive agent delivery system, such as less than 15 mm, less than 10 mm, less than 9 mm, less than 8 mm, less than 7 mm, less than 6 mm, less than 5 mm, and/or may be larger than any of these amounts (e.g., greater than 5 mm, greater than 6 mm, greater than 7 mm, greater than 8 mm, greater than 9 mm, greater than 10 mm, greater than 12 mm, or in between any of these sizes (e.g., greater than 7 mm and less than 9 mm in diameter, or greater than 8 mm and less than 11 mm, etc.). For example, a spring for a relatively small, wearable bioactive agent delivery system may have a sufficiently small diameter so that the delivery system fits comfortably (relatively flatly) against a user's body, but be long enough to provide sufficient force to deliver a plurality (2, 3, 4, 5, 6, or more than 6) doses of bioactive agent through the system. A spring of a bioactive agent delivery system may be or include a single spring or may include plurality of springs (e.g., 2, 3, 4, 5, or more than 5 springs). A system with a plurality of springs may be configured such that an individual spring or two (or more than two springs together) provide or meet the above indicated parameters. A single spring may be helpful, for example to minimize device size (length, height or width), such as for acting on a single reservoir or for another reason. A plurality of springs may be helpful for minimizing the device length (e.g., by having more but relatively shorter springs acting on a reservoir) or for acting on a plurality of reservoirs or for another reason. For example, a bioactive agent delivery device may contain 1, 2, 3, 4, 5, or more than 5 reservoirs, and each reservoir may have an associated spring. As indicated above, a spring may be part of reusable part. Having a spring in a reusable part may be useful for reducing system cost, since the spring can be reused for easily pressurizing a reservoir(s) in an additional disposable part, etc. Although a spring (or other component) is described herein as being part of a reusable part, it does not need to be part of a reusable part. In some variations a spring may be part of a disposable part. For example, a spring (e.g., a spring) in a disposable part may allow the bioactive agent delivery system to be stored pressurized, which may improve bioactive agent shelf life, piston seal shelf life, etc.

Piston 34 may be a disk or other structure that fits (e.g., fits snugly) in reservoir 38 and interacts with spring 28, either directly or indirectly. The spring 28 may act on piston 34 to place a pressure on the contents of reservoir 38 of at least 1.0 bar, at least 1.5 bar, at least 2.0 bar, at least 2.5 bar, at least 3.0 bar, at least 3.5. bar, at least 4.0 bar, at least 4.5 bar, at least, 5.0 bar or less than 12 bar, less than 10.0 bar, less than 8.0 bar, less than 7.0 bar, less than 6.0 bar, less than 5.0 bar, less than 4.5 bar, less than 4.0 bar, less than 3.5 bar, less than 3.0 bar, less than 2.5 bar, less than 2.0 bar or anything in between these amounts (e.g., between 2.0 bar and 4.5 bar, between 2.3 bar and 4.2 bar, etc.). In some particular examples, a disposable part is configured such that a piston is configured to provide from 2.3 to 4.6 bar. Pressure from the piston may be greater than 1.0×, greater than 1.5×, greater than 2.0×, greater than 2.5×, etc. of atmospheric pressure. Atmospheric pressure is generally around 1.0 bar (e.g., 1.067 bar) and pressure within the system is generally higher than atmospheric pressure in order to allow passive pressure flow from the disposable part to the environment. In some variations, a disposable device configuration may be chosen to operate at different temperatures, operate upside down (e.g., against the flow of gravity, etc.).

Reservoir 38 is configured to have a variable volume due to movable piston 34. Initially, the reservoir contains multiple doses of bioactive agent and the reservoir volume is relatively large. Reservoir 38 may contain or be configured to contain between 1 µl and 2000 µl of bioactive agent. Reservoir 38 may contain or be configured to contain at least 1 µl, at least 10 µl, at least 50 µl, at least 100 µl, at least 150 µl, at least 200 µl, at least 300 µl, at least 400 µl, at least 500 µl, at least 600 µl, at least 700 µl, at least 800 µl, at least 900 µl, or at least 1000 µl. Reservoir 38 may contain or be configured to contain a maximum of 2000 µl, 1500 µl, 1000 µl, 900 µl, 800 µl, 700 µl, 600 µl, 500 µl, 400 µl, 300 µl, 200 µl, 150 µl, 100 µl, 50 µl or in between any of these amounts (e.g., in between 100 µl and 500 µl, in between 300 µl and 800 µl, etc.).

Reservoir 38 may contain or be configured to contain a selected number of doses of defined size, and may include an extra "fill" volume to ensure that a sufficient volume is available to deliver all desired doses (given some normal but minimal/acceptable variability in chamber size, etc. for example based on manufacturing variability). For example, reservoir 38 may contain 3, 4, 5, 6, etc. doses of 100 µl, 125 µl, 150 µl, 175 µl, 200 µl plus+/−10% or another pharmaceutically acceptable variation. Thus in some examples, reservoir 38 contains 5×100 doses (500 µl+/−10%), 5×125 doses (625+/−10%), etc. The size of reservoir 38 may be chosen based on the amount of bioactive agent desired, bioactive agent concentration, bioactive agent solubility, viscosity (e.g., of a bioactive agent or a solution containing a bioactive agent), etc.

In this embodiment, valve 50 delivers bioactive agent from reservoir 38 into a bolus chamber 46. Bolus chamber 46 has a smaller volume than reservoir 38 and can therefore be used to control the size of a bolus or dose of the bioactive agent. In this embodiment, bolus chamber 46 has a variable volume due to a piston 51 that moves against the action of a force provider 53, such as a spring or a hydraulic pressure source. The volume of the dose entering bolus chamber 46 from reservoir 38 through valve 50 depends on the outlet pressure of reservoir 38, the surface area of piston 51, and the force from force provider 53. In some embodiments, these parameters are chosen so that the effective volume of bolus chamber 46 is constant for every dose received from reservoir 38, such as by moving piston 51 to the limit of its possible travel with every bolus entering the bolus chamber.

In this embodiment, valve 50 has a second position that communicates bolus chamber 50 with the system outlet 54 for delivery of the bioactive agent to the user 4. Thus, valve 50 prevents direct bioactive agent flow from the reservoir to the outlet/user, reducing risk of delivering too much bioactive agent at any time (e.g., reducing risk of an overdose).

Electronics apparatus 12 is configured to control timing of delivery of bioactive agent doses to user 4 by disposable part 8. Electronics apparatus 12 includes a controller such as a computer, microprocessor, printed circuit board (PCB), processor, or another electronic device configured to control bioactive agent delivery. Delivery time of a bioactive agent dose controlled by electronics apparatus 12 may pre-programmed (e.g., programmed ahead of time) or may be controlled at the time of delivery (e.g., may be delivered on-demand). Electronics apparatus 12 is also configured to receive user input 24 such as from a finger, hand, a mobile device (e.g., Bluetooth, smartphone, Zigbee, etc.) voice command or from another input; input may be set-up ahead of time or may be an "on-demand" input. Electronics apparatus 12 controls timing of bioactive agent delivery by controlling valve driver 13 (and therefore valve 50) and allowing or preventing bioactive agent delivery to a user by controlling the timing bioactive agent flow from reservoir 38 to bolus chamber 46 and from bolus chamber to outlet 54. As shown in FIG. 1, electronics apparatus 12 is in reusable part 6, but in other embodiments in may be in the disposable part.

A bioactive agent delivery system as described herein may be configured (e.g., via electronics apparatus 12) to deliver a bioactive agent at regular times and/or at irregular times, and during one or more than one days. A regular time may be a regular time during a day (e.g., every 2 hours, every 4 hours, etc.) or a regular time on different days (e.g., just before waking up, at meal time, etc.). A bioactive agent delivery system may be configured (e.g., via electronics apparatus 12) to deliver a bioactive agent to a user at one or more predetermined times (e.g., it may be pre-programmed). A bioactive agent delivery system may allow a user to request delivery of a bioactive agent, and bioactive agent may also or instead be delivered "as-needed" during a day(s), such as based on a user request (e.g., from user input 24). For example, a person using a bioactive agent delivery system for smoking cessation may recognize they are experiencing a craving for a cigarette and may request delivery of a dose of a smoking cessation agent to help control the craving and prevent them from smoking a cigarette. For example, a patient may request a dose of bioactive agent such as codeine, fentanyl, ibuprofen, methadone, or another agent for pain management or other therapeutic or prophylactic use as needed. In some examples, a system may count or otherwise determine how much bioactive agent a user has received in a given time period. Based on determination such as this, a system may determine that a user is eligible to receive a dose of bioactive agent and may deliver a bioactive agent dose to the user in response to the request (e.g., by signaling valve driver 13 to move and deliver a dose to user 4). In some examples, a system may determine that a user is not eligible to receive a dose and may not deliver a dose in response to a user's request (e.g., may not signal valve driver 13 to move). For example, a system may count or otherwise determine that a user has received as much bioactive agent as allowed in a given time period; an additional dose may be an overdose or otherwise dangerous. A bioactive agent delivery system may be pre-programmed with bioactive agent delivery times, such as with pre-set times (e.g., by or as determined by a manufacturer, pharmacist, medical professional, etc.) or as customized by the user. For example, a system may be programmed to provide a smoking cessation agent before a person's craving is likely to start or become strong. Thus a system may be programmed to deliver a dose based on an expectation that it may be needed (before or without such a need actually appearing). Such programming may be based on the user's history or habits, data or statistical analysis of other users, etc. For example, a user may previously have experienced cravings to smoke upon waking up from sleep and a system may be programmed to provide a dose of nicotine or other smoking cessation agent before or around the time the user expects to awaken.

Electronics apparatus 12 generally includes a power source (battery) for providing power to the printed circuit board, computer or other electronic component in electronic apparatus 12. A power source may also provide power to valve driver 13 to change the configuration of valve 50 and move bioactive agent through disposable part 8 or to user 4.

Reusable part 6 includes a valve driver 13 for controlling bioactive agent flow in the disposable part when the reusable part 6 is connected to the disposable part 8 by controlling operation of valve 50 in disposable part 8. Valve driver 13 may be an electromechanical actuator controlled by (and receiving power from) electronics apparatus 12. A valve driver may be any type of valve driver that can move the valve or move part of the valve (e.g., the valve core) at least from a first position to a second position to control bioactive agent flow through disposable part 8. A valve driver may be or may include a geared DC motor such as DC motor with a 4-stage planetary gearbox or another valve driver that is efficient at getting mechanical work from electrical energy at the scale of the bioactive agent delivery system. A small or lightweight valve driver that consumes minimal energy may be especially useful to minimize the size or weight of the valve driver and/or the power source such as a battery in a wearable system. An efficient valve driver may minimize the frequency with which a power source is recharged or replaced. A valve driver may include a pair of shape-memory alloy wires acting against a return spring or another driver generally with a low energy requirement that can control valve 50 to control bioactive agent flow in disposable part 8. A valve driver may include a voice coil or another driver that is lightweight or takes up relatively minimal space. A valve driver may include a shape-memory alloy driver or another driver that is quiet (or silent) or creates minimal (or undetectable) vibration or other disturbance to a user. A valve driver may include a stepper motor or another driver that limits valve (or part of a valve) movement, such as in a limited range or motion, a limited number of positions, or in only specific positions such as including and in between a first position and a second position. Any of the above mentioned valve drivers may be used in any bioactive agent delivery system but may be especially useful in a portable or wearable bioactive agent delivery system.

Bioactive agent delivery to a user using the bioactive agent delivery system shown in FIG. 1 generally takes place in four steps. First, bioactive agent in reservoir 38 is pressurized (e.g., above atmospheric pressure) due to the action of spring 28 on piston 34 (directly or indirectly). Second, movement of valve 50 to a first position permits a single dose of bioactive agent to fill bolus chamber 46 by moving piston 51 against the action of force provider 53. The surface area of piston facing the bolus chamber and the spring force of force provider 53 are chosen so that the pressure of the bioactive agent flowing out of reservoir 38 is high enough to move piston 51 against the action of force provider 53 to permit the bioactive agent to enter the bolus chamber. Third, valve 50 moves to a second position to permit the single dose of bioactive agent in bolus chamber 46 to flow to outlet 54. Pressure provided by the action of force provider 53 against piston 51 causes the bioactive agent to flow from the bolus chamber 46 through valve 50 to the outlet 54. Fourth, the dose of bioactive agent flows from outlet 54 through a delivery path 57 to user 4 where the bioactive agent can have a bioactive (e.g., prophylactic or therapeutic) effect. Delivery path 57 may include, e.g., a transdermal patch or membrane, a cannula, or other patient interface.

In some variations, one or more wall(s) of the reservoir 38 in the disposable part may be a flexible or compressible (e.g., resiliently flexible and capable of returning to an original size after being compressed or collapsible and unable to return to an original size) and the walls may be compressed in response to force from spring 28.

In some variations, a flexible reservoir in the disposable part may be relatively flexible over substantially its entire body and the entire body may be compressed in response to an applied force. In some variations, a flexible reservoir may include a first region that is inflexible and a second region that is relatively flexible such that a piston or other compressive structure may act on the flexible reservoir and collapse or compress a portion the flexible reservoir (e.g., a flexible portion) to pressurize bioactive agent. For example, a flexible reservoir may be a bag or bladder, or another compressible structure able to contain bioactive agent, and a piston or other force (e.g., on the outside of the bag or bladder) may act to compress the bag or bladder to pressurize bioactive agent. During reservoir and bioactive agent compression by piston 34, the bioactive agent flow pathway between the reservoir and the bolus chamber may be open or closed.

Although a disposable part is referred to above as having a reservoir, a disposable part may have one reservoir, or may have a plurality of reservoirs (e.g., 2, 3, 4, or more than 4 reservoirs). A plurality of reservoirs in a disposable part may be joined together or may be standalone components. Each reservoir may contain 1, 2, 3, 4, 5 or more than 5 doses of bioactive agent. As indicated elsewhere, a bioactive agent delivery system may contain 1 or more than one spring that can act on a reservoir, and one spring may act on one reservoir to pressurize bioactive agent and each reservoir may have a single spring pressurizing it or a single spring may act on a plurality of reservoirs. Active agent in a disposable part (e.g., in a reservoir) may be pre-loaded with a bioactive agent or may not be pre-loaded. A reservoir may be loaded by a nurse, pharmacist, user, etc.). A disposable part that is not pre-loaded may for example be easier to manufacture or to store. For example, different components of a disposable part (including bioactive agent) could be manufactured at different times or as needed; a single type of disposable part may be usable with different bioactive agents and a particular bioactive agent can be loaded into the disposable part only as needed, etc.).

In some variations, a disposable part may be configured to minimize tampering. A disposable part may be configured to substantially prevent a user from placing a bioactive agent (e.g., an illegal drug or other agent) into a disposable part. For example, a reservoir may not have a bioactive agent loading port readily available for a user to use to load bioactive agent. For example, a reservoir may be made from or covered by a hard material (such as a plastic or stainless steel) that is difficult to penetrate with a syringe or other bioactive agent loading device. These or other disposable part configurations may be relatively tamper-proof. They may prevent a user from using a disposable part for a different purpose (e.g., illegal drug use, overdose, etc.) than its intended (therapeutic or prophylactic) purpose.

A valve for use in a disposable part may be a plug valve or gate valve or another valve that can control (e.g., at different times allow or prevent) fluid flow between reservoir 38 and bolus chamber 46 or between bolus chamber 46 and outlet 54. A valve is generally configured so that bolus chamber 46 is only connected (e.g., a flow path is open) to reservoir 38 or to outlet 54 but not both simultaneously. A valve may be a 3-way valve such as a gate valve or a plug valve or another valve that minimizes risk of overdose or unintended medication delivery to the patient for example by preventing a direct flow path from reservoir 38 to outlet

54 (user). A valve may be configured such that there is no direct flow path between a bioactive agent reservoir and an outlet to a user and bioactive agent cannot flow directly from the reservoir to an outlet (e.g., regardless of what configuration a valve is in).

The valve 50 may have a valve body and a valve core that moves relative to the valve body and controls the flow of bioactive agent through the valve. A valve body may be configured to stay in a position(s) relative to the valve core and relative to other components in the disposable part and/or reusable part without requiring a force to hold it in the position(s). In some variations, a valve may have a rotatable core inside a valve body and one, two (or more) hollow passageways through the valve core configured for bioactive agent to flow through. In some variations, a valve (and/or valve driver) may be configured so that the valve (e.g., valve core) has limited movement. Such a configuration may be useful to minimize the amount of energy required to operate the valve, improve valve accuracy (by positioning the valve only in a limited number of desired locations), etc. This may be useful to reduce system complexity, system size (e.g., power source size), system weight (e.g., power source weight), eliminate or reduce energy recharging, etc. This may be especially useful in a wearable bioactive agent delivery system to minimize size and improve user acceptance.

In some examples, a rotatable valve (or rotatable valve core) may rotate 180° or fewer degrees, 135° or fewer degrees, 90° or fewer degrees, 80° or fewer degrees, 70° or fewer degrees, 60° or fewer degrees, 50° or fewer degrees, or 40° or fewer degrees. In some particular examples, a valve core may be configured to rotate between two different positions, such as rotating from about 60° to about 90° to move the valve between a first configuration and a second configuration. Thus a valve may move clockwise and counterclockwise.

For example, a 3-way valve (e.g., an "L" shaped 3-way valve) may have a valve body with three connections to the disposable part (e.g., one leading to the reservoir, one leading to the bolus chamber, and one leading to the outlet) and a valve core with two ports connected by a passageway through a hollow member (e.g., passageway may be "L" shaped) in the valve. A 3-way valve has two flow patterns: a first flow pattern allowing bioactive agent flow from the reservoir to the bolus chamber in which a first port is open to the reservoir and a second port is open to the bolus chamber (with no bioactive agent flow to the outlet/user) and bioactive agent flows through the channel from the reservoir to the bolus chamber through a first flow path, and a second flow pattern from the bolus chamber to the outlet in which the first port is open to the outlet and the second port is open to the bolus chamber (with no bioactive agent flow to the reservoir) and bioactive agent flows through from the bolus chamber to the outlet through the channel.

A disposable part may include a single 2-position, 3 port plug valve. In an L-shaped 3-way valve, there is no direct bioactive agent fluid flow pathway from the reservoir to the outlet, and risk of overdose or unintended bioactive agent delivery to the user is greatly reduced. In some variations a 3-way or other valve may also be in third position relative to the rest of the disposable chamber and prevent bioactive agent flow (e.g., prevent any flow) between the reservoir, bolus chamber, and outlet; the valve may be completely closed to bioactive agent flow. In some other examples, a valve may be a "T" shaped 3-way valve, with three connections to a disposable part in a valve body and three ports connected by a passageway through a hollow member in the valve core. A "T" shaped valve may be configured and placed in a bioactive agent delivery system such that there is no direct flow pathway between the reservoir and outlet in any position that the valve (e.g., the valve core) can take.

In some examples, a disposable part may be configured so that bioactive agent could flow in either direction between the reservoir/bolus chamber or bolus chamber/outlet (e.g., it may lack a non-return valve or other structure to prevent bioactive agent flow from the bolus chamber back to the reservoir), but is prevented from flowing from the bolus chamber back to the reservoir due to the higher reservoir pressure (or in the second example, higher bolus chamber pressure) compared with the bolus chamber pressure (or in the second example, outlet pressure).

A valve may be configured to minimize friction between the valve and the fluid (bioactive agent) flowing through it. In some examples an internal diameter of a hollow of a valve may be the same or close to the same as an internal diameter of a first flow passageway (e.g., between a reservoir and a bolus chamber) or a second flow passageway (between a bolus chamber and an outlet).

In some examples, a valve (e.g., a valve core) may be bi-stable and may be stable (resting) in either of two positions. A 3-way valve may be bi-stable, for example, in either of two configurations: in a first configuration with the valve core in a first position so that a passageway is open in the valve between the reservoir and the bolus chamber (and closed to the outlet), or in a second configuration with the valve core in a second position so that a flow path open between the bolus chamber and the outlet (and closed to the reservoir). A bi-stable valve stays in one of its configurations until it is acted on by a force to change its configuration (e.g., in the example of a 3-way valve to move the valve core from a first position to a second position). Power is not required to maintain a bi-stable valve in a particular configuration. Power is applied to move a valve between different configurations (e.g., from a first position to a second position or a second position to a first position, such as described above). A valve may remain in a position until it is acted on, such as acted on by valve driver 13. A valve may be between 5 mm and 20 mm in length or any length that is able to control bioactive agent fluid flow and fit into the disposable part. In some examples a valve is between 8 mm and 15 mm, 10 mm and 12 mm, etc. A valve cross-section (e.g., a diameter if a valve has a substantially circular cross-section) may be between 0.5 mm and 5 mm, such as between 0.7 mm and 2.0 mm, between 0.8 mm and 1.5 mm, etc.).

In general, the dosing volume (e.g., effective volume of the bolus chamber when it is filled with bioactive agent) is highly repeatable and/or reproducible such that each dose is within a pharmaceutically acceptable range. Due to small manufacturing differences or other acceptable variances, doses may vary in volume or activity by a pharmaceutically acceptable amount (such as by +/−5%, +/−10%, +/−15%, etc.). A bolus chamber may, for example, be configured to receive (e.g., a swept volume of a bolus chamber may be) between 1 µl and 1000 µl of bioactive agent for each dose. A bolus chamber may receive at least 1 µl, at least 10 µl, at least 50 µl, at least 100 µl, at least 150 µl, at least 200 µl, at least 300 µl, at least 400 µl, at least 500 µl, at least 600 µl, at least 700 µl, at least 800 µl, at least 900 µl, or at least 1000 µl. A bolus chamber may be configured to receive a maximum of 1000 µl, 900 µl, 800 µl, 700 µl, 600 µl, 500 µl, 400 µl, 300 µl, 200 µl, 150 µl, 100 µl, 50 µl or in between any of these amounts (e.g., in between 50 µl and 200 µl, in between 100 µl and 300 µl, etc.). In some examples, a bolus chamber is configured to hold between 100 µl and 300 µl and contains nicotine. A dose of nicotine may be, for example 100 µl, 125 µl, 150 µl, 175 µl, 200 µl etc. or in between any of these amounts. A bolus chamber size may be chosen based on the amount of bioactive agent desired, bioactive agent concentration, bioactive agent solubility, viscosity (e.g., of a bioactive agent or a solution containing a bioactive agent), etc. Although for simplicity the bolus chamber is referred to herein as receiving and delivering a dose of bioactive agent, the bolus chamber could instead receive a partial dose (e.g., 1/Nth of a dose), and deliver multiple cycles of partial doses (e.g., N cycles having 1/Nth of a dose). Thus a dose could be delivered in 1, 2, 3, 4, 5, or more than 5 cycles.

Outlet 54 is an opening fluidly connected with bolus chamber 46 via valve 50. Outlet 54 generally delivers bioactive agent to a delivery component (such as a transdermal patch, microneedle, etc.) for bioactive agent delivery to user 4. A delivery component may be integral with or separated from a disposable part. As indicated above, bioactive agent pressure in bolus chamber 46 is greater than the pressure at outlet 54 and/or a delivery component or user, which is generally at or around atmospheric pressure.

When a flow path is opened between bolus chamber 46 and outlet 54 by valve 50, a dose of bioactive agent flows from the area of higher pressure in the bolus chamber) to the area of lower pressure (outside of the outlet). After flowing through outlet 54, a bioactive agent may be delivered to a user by any appropriate delivery method. For example, bioactive agent may be delivered using iontophoresis (e.g., with an iontophoretic patch), microneedles, a needle, a topical patch (e.g., configured for delivery of a bioactive agent local at the site of application (skin) without resulting in a significant bioactive concentration in the blood), a transdermal patch, etc.

Bioactive agent flow from bolus chamber 46 through outlet 54 to a delivery component may take place very quickly. Bioactive agent flow through outlet 54 may be faster than is flow generated by a pump (e.g., a mechanical device for moving bioactive agent). Rapid delivery to a delivery component may be especially useful for wetting a membrane for transdermal or topical bioactive agent delivery. Rapid flow may cause effective wetting of a topical or transdermal membrane (e.g., essentially the entire membrane) without significantly forcing bioactive agent through the membrane (during the wetting process). Rapid wetting and absorption of a bioactive agent through a user's skin may minimize evaporative (solvent) loss and provide for better or more consistent bioactive agent delivery to a user.

In some variations, and as described in more detail below, a dose of bioactive agent may be delivered through an outlet (to a delivery component such as to a skin delivery member of a transdermal patch as described below) in less than 5 seconds, less than 4 seconds, less than 3 seconds, less than 2 seconds, less than 1 second, less than 0.5 seconds, less than 0.1 seconds, etc. Thus a bioactive agent delivery system may be configured to provide 1 or a plurality of doses (e.g., 2, 3, 4, 5, 6 or more doses) to an outlet or user within such time frames. For example, a dose of nicotine may be delivered in less than 2 seconds, 1 second, or 0.5 seconds and may rapidly wet a skin delivery member to provide rapid bioactive agent transfer to a user. Such transfer may be useful to quickly provide a nicotine dose to control a craving for a cigarette. In some variations, a dose of bioactive agent may be delivered through an outlet (to a delivery component such as to a skin delivery member of a transdermal patch as described below) over a longer time period such as at least 1 minute, 5 minutes, an hour, two hours, etc. Thus a system may behave as timed release or extended release.

In some particular examples, a fluid space connects outlet 54 and a membrane of a transdermal patch configured to contact a user's skin, and bioactive agent flows from outlet 54 to the membrane and the membrane (essentially the entire membrane) is wetted in less than 5 seconds, less than 1 second, less than 0.5 seconds, less than 0.1 seconds, etc. Any parameter of the system may be chosen to control the amount of time for bioactive agent delivery from the bolus chamber (or outlet) to a skin delivery membrane or another user delivery member. Skin delivery membrane features (e.g., membrane material, membrane hydrophilicity, membrane size, channels, pore size, etc.), other fluid distribution features (such as the presence of channels or another fluid distribution feature on another membrane configured to move bioactive agent between the bolus chamber and the skin delivery membrane, diameter or size of any channels or other fluid distribution features), bioactive agent pressure, spring parameters (size, strength, etc.) or another system feature may be chosen to control wetting efficiency, such as wetting time, wetting speed, depth of wetting or another parameter.

A reusable part may be used with a single disposable part, but in general will be used with a plurality of disposable parts. In some variations, a disposable part can be refilled or recharged and reused. Bioactive agent, a power source (if present), etc. may be replaced used disposable part as appropriate.

In some embodiments, a disposable part (e.g., bioactive agent and a reservoir) may be pressurized by the action (of a user) of loading a disposable part into or onto a reusable part, e.g., loading a disposable part into a reusable part provides a pressurization force. As described above, compressing the spring provides a force on the piston for the piston to pressurize the reservoir and bioactive agent in the disposable part. Taking advantage of providing a force upon loading the disposable part may minimize the size or weight of a bioactive agent delivery system and make the system more comfortable or easier to use. For example, by using the action of the user loading the disposable part to provide a force, a large or heavy pump and associated components such as power for the pump, etc. is not required for pressurizing bioactive agent.

A bioactive agent delivery system as described herein is generally configured without a direct pathway between the reservoir and outlet to minimize a risk of bioactive agent overdose: the large amount of bioactive agent in the reservoir cannot be directly delivered to a user. In some variations, a disposable part may be configured so that a valve (e.g., a valve core) in the system can be in any (e.g., two or more) of its possible configurations when a disposable part is loaded into a reusable part. Such a system may be more convenient or easier for a user to use. For example, a user may be able to replace a disposable part at whatever time it is convenient for them to do so without being concerned with checking or changing a valve position before doing so. Such a system may minimize device size or weight which may be an advantage such as for a wearable system. For example, a system may readily use a bi-stable or other valve that requires minimal power to operate (since the valve can stay in whatever position it is in and the disposable part can be replaced regardless of the valve configuration. Power consumption (and power source size or weight, overall system size or weigh, etc.) may be minimized.

Figure 2:
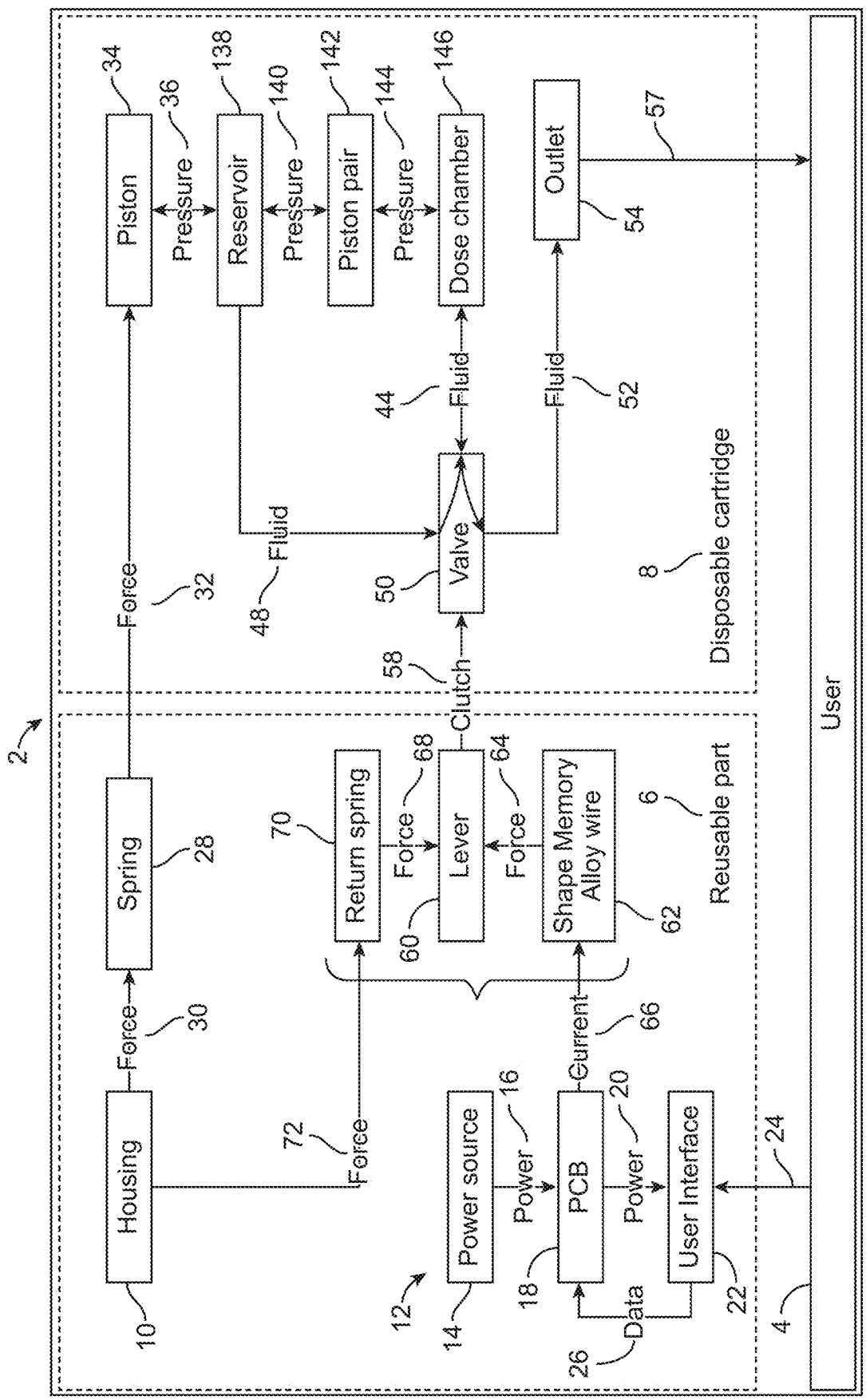
FIG. 2 is a block diagram of a two-part bioactive agent delivery system according to another embodiment of the invention.
Figure 3A:
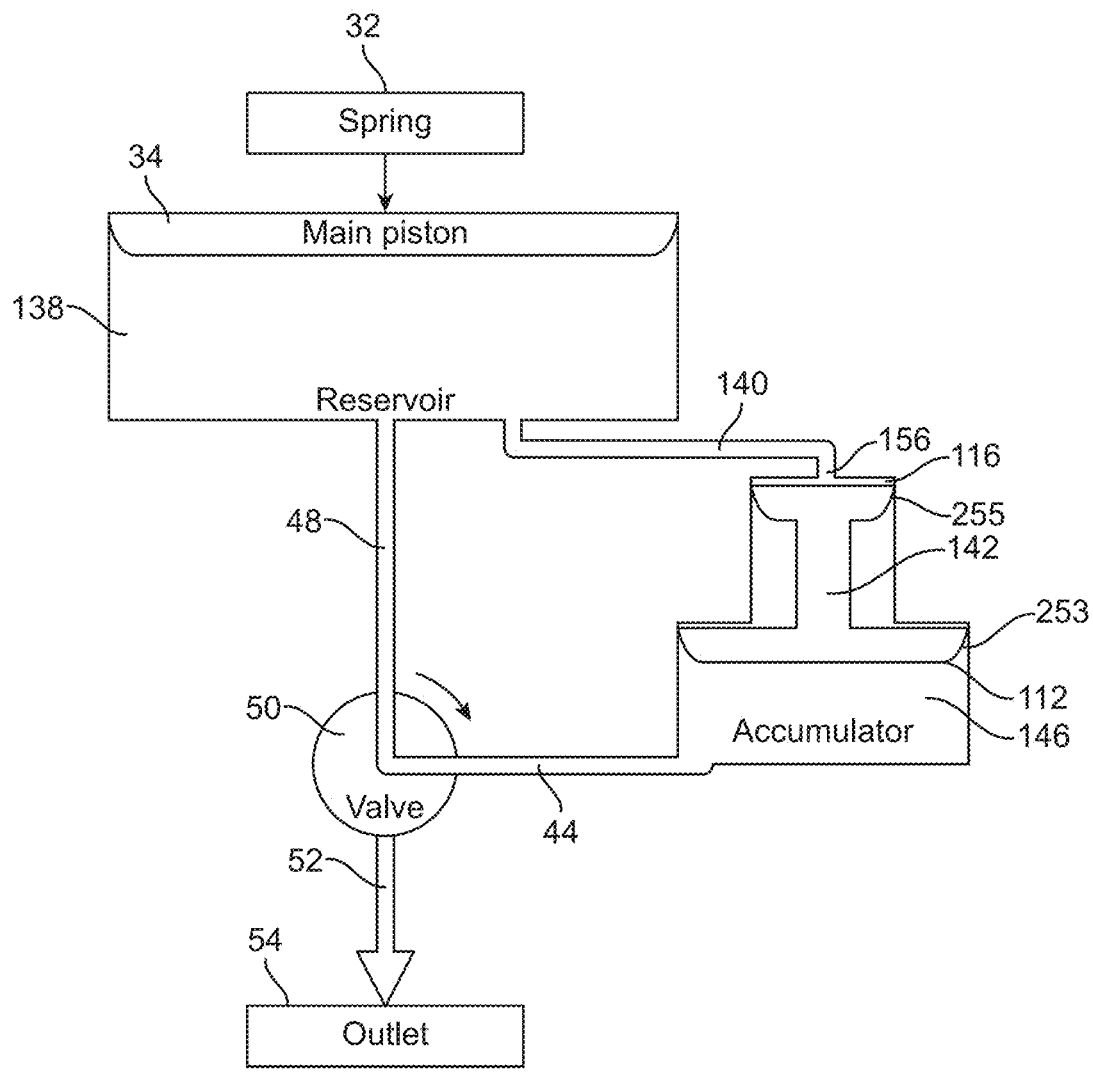
FIGS. 3A-3B show a schematic of part of the disposable portion of a two-part bioactive agent delivery system.
Figure 3B:
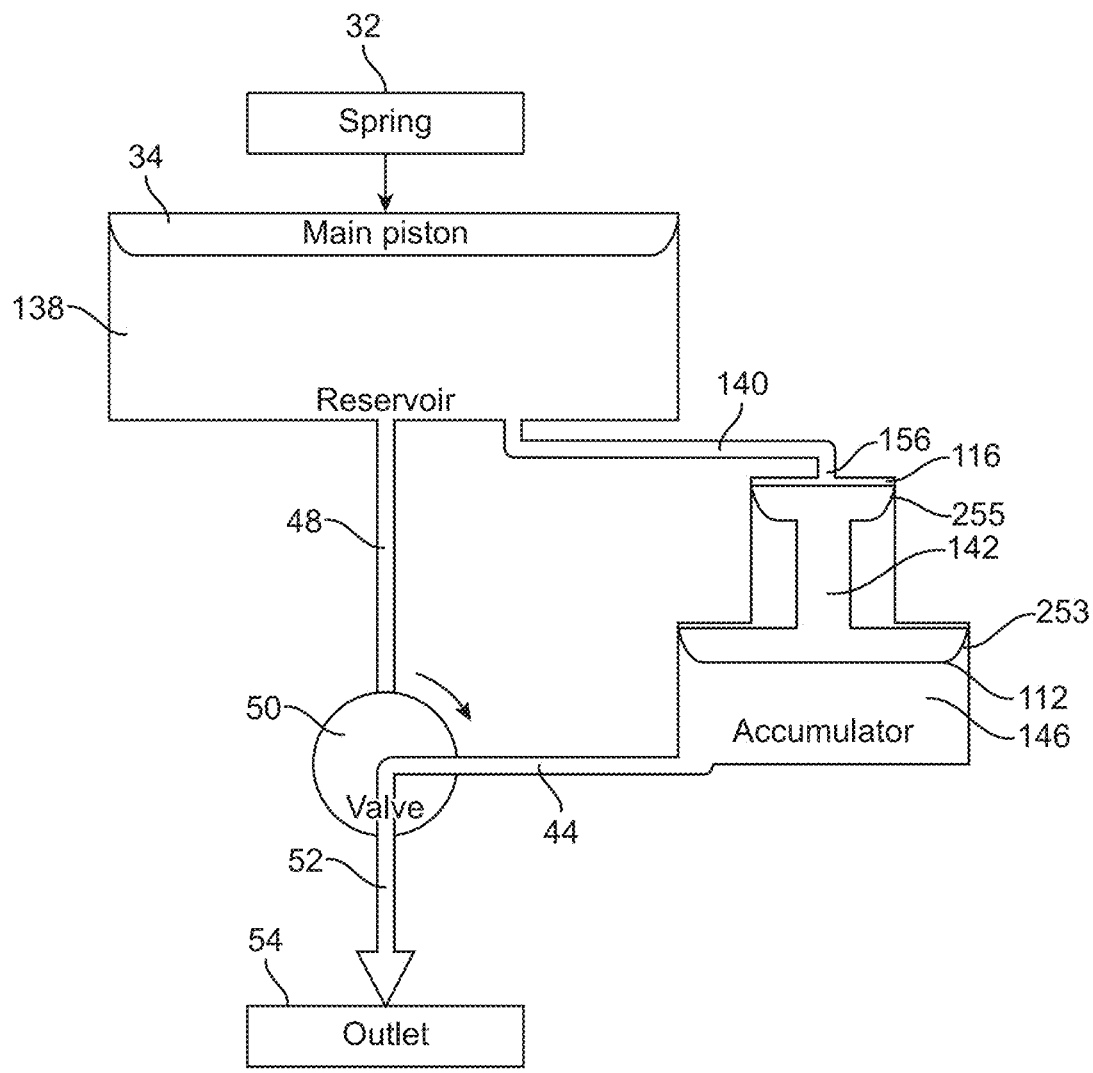

FIGS. 2 and 3 show a two-part bioactive agent delivery system 2 with reusable part 6 and disposable part 8 that work together to deliver drug or another bioactive agent to user 4. Reusable part 6 includes housing 10, electronics apparatus 12, valve driver 13, and spring 28 such as described above. Disposable part 6 includes piston 34, valve 50, reservoir 138, bolus chamber 146, piston 142, and outlet 54. Some of these are described above with reference to FIG. 1 and others are described below.

To drive fluid flow through the system, piston 142 is fluidly connected to reservoir 138 by hydraulic flow path 140 to provide a pressurizing force for bolus chamber 146. Bolus chamber 146 is fluidly connected via valve 50 either with reservoir 138 by reservoir flow path 48 or with outlet 54 by outlet flow path 52. In both cases, bioactive agent flows from bolus chamber 146 to valve 50 by bolus chamber flow path 44.

As shown in FIG. 3, piston 142 is actually a pair of pistons connected by a shaft. Smaller piston 116 has a face in fluid communication with reservoir 138, and larger piston 112 has a face in fluid communication with accumulator or bolus chamber 146. Seals 253 and 255 surround pistons 112 and 116, respectively. Because the surface area of piston 116 is smaller than the surface area of piston 112, the dual pistons will move to the position shown in FIG. 3 when valve 50 connects reservoir 138 with accumulator or bolus chamber 146. When valve 50 is turned (e.g., under action of the valve drive 13 shown in FIG. 2) to connect bolus chamber accumulator 146 with outlet 54, the lower pressure at the outlet will permit dual piston 142 to move under the influence of the force exerted on piston 116 by reservoir 138 to dispense the contents of accumulator 146 to outlet 54.

As in the earlier embodiments, accumulator or bolus chamber 146 is sized to contain a single dose of the bioactive agent, and reservoir 138 is sized to contain multiple doses. Seals 253 and 255 provide frictional stability to the system in addition to preventing leaking of bioactive agent around pistons 116 and 112. The surface area of piston 112 facing accumulator or bolus chamber 146 may be 1.1×, 1.5×, 2.0×, etc. larger than the surface area of piston 116 facing reservoir 138. A patient interface may be provided at outlet 54, as discussed above with respect to FIG. 1. In addition, user input may be provided to reusable part 6 as discussed above with respect to FIG. 1.

FIG. 2 also shows electronics apparatus 12 and valve driver 13 in reusable part 6. Electronics apparatus 12 is configured to control valve driver 13 which in turn controls the configuration of valve 50. Valve 50, as described above, controls the flow of bioactive agent through disposable part 8. Valve driver 13 includes wire 62, lever 60, and return spring 70. Wire 62 is a shape-memory alloy wire configured to shape-change from a first shape to a second shape (such as first and second lengths) in response to current 66 from electronics apparatus 12. When wire 62 moves from its first shape to its second shape, it moves valve 50 from a first position to a second position. As described above, the position of valve 50 controls how bioactive agent fluid flows through the system.

Figure 4A:
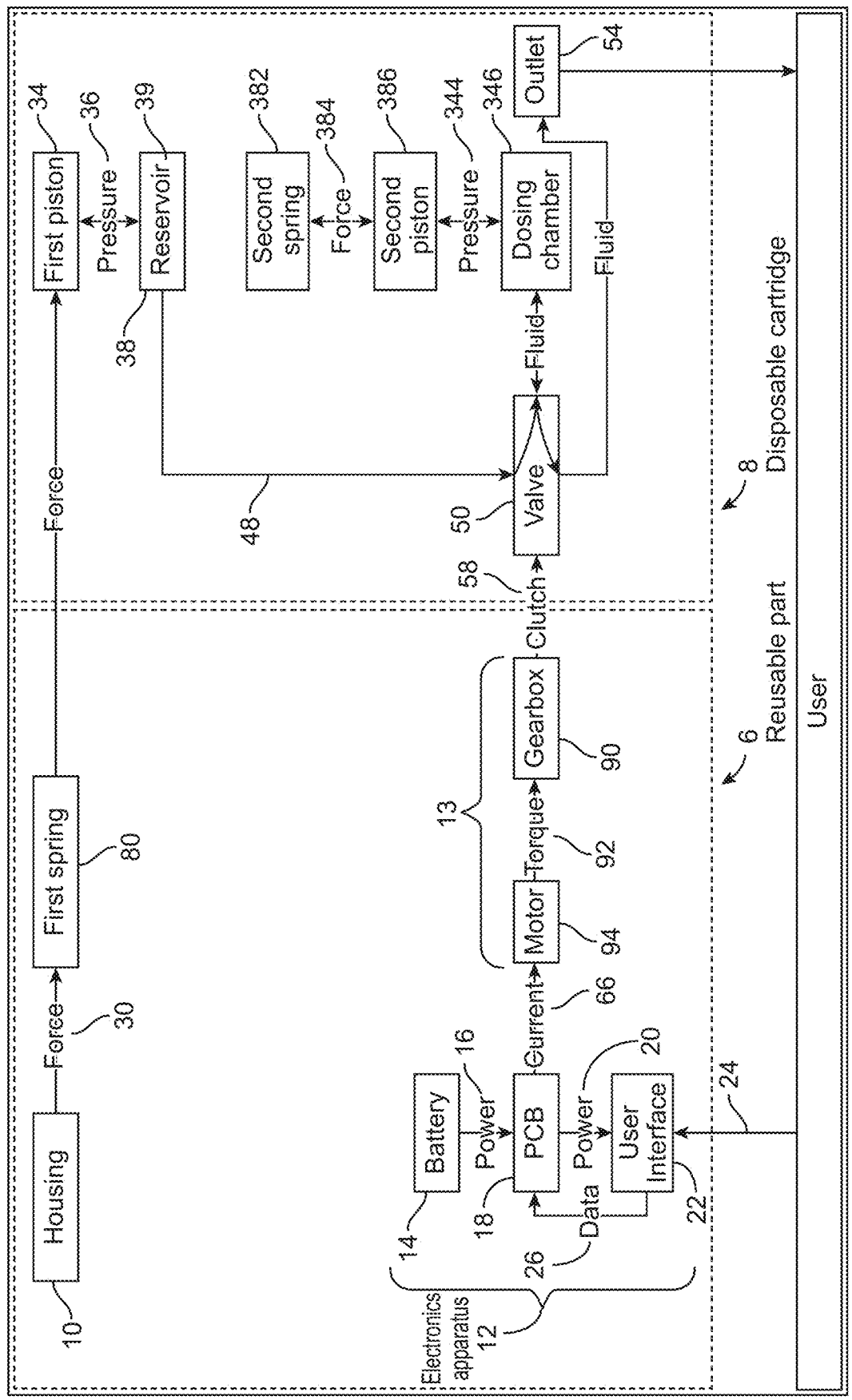
FIG. 4A shows a block diagram of another two-part bioactive agent delivery system using a motorized valve driver and a spring controllable bolus chamber.
Figure 5A:
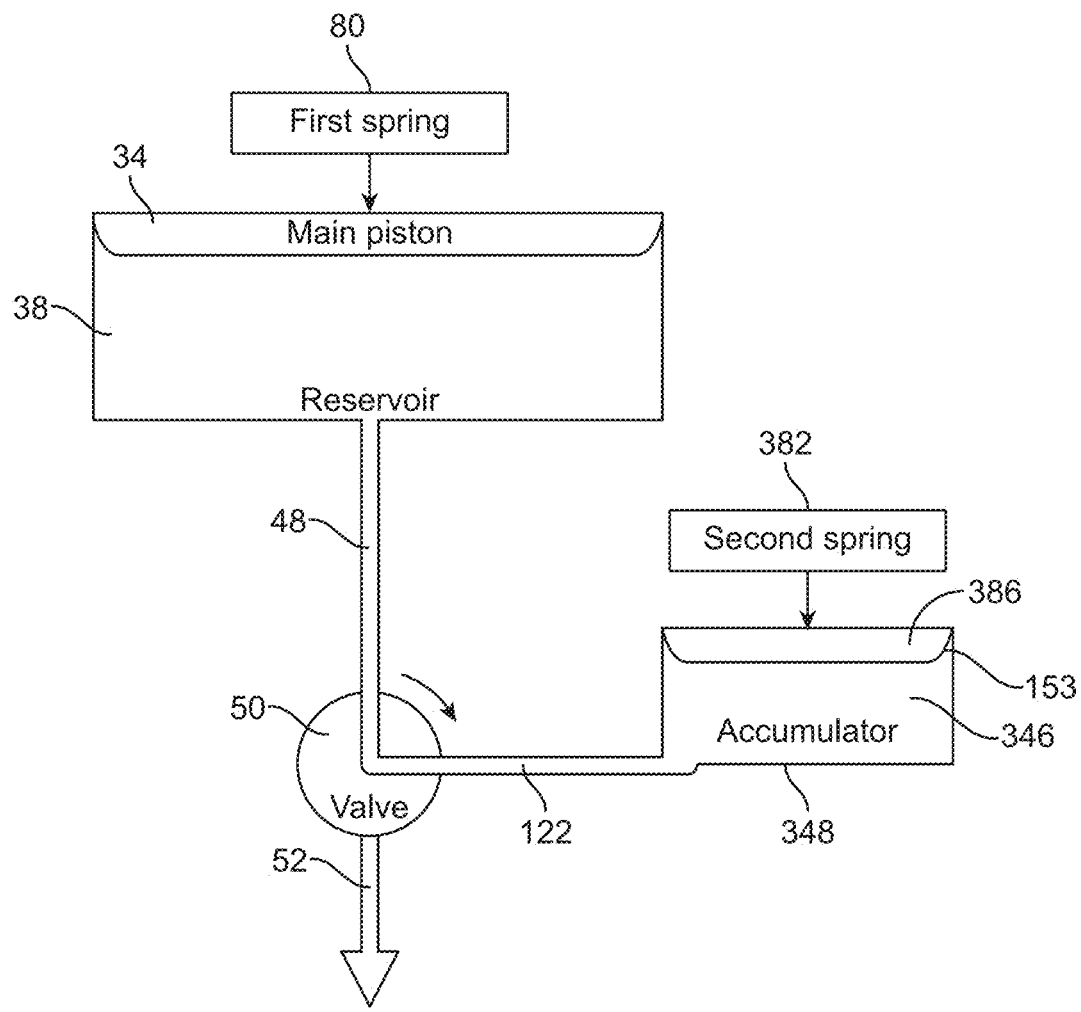
FIGS. 5A and 5B are schematic views of portions of a two-part bioactive agent with a spring controllable bolus chamber.
Figure 5B:
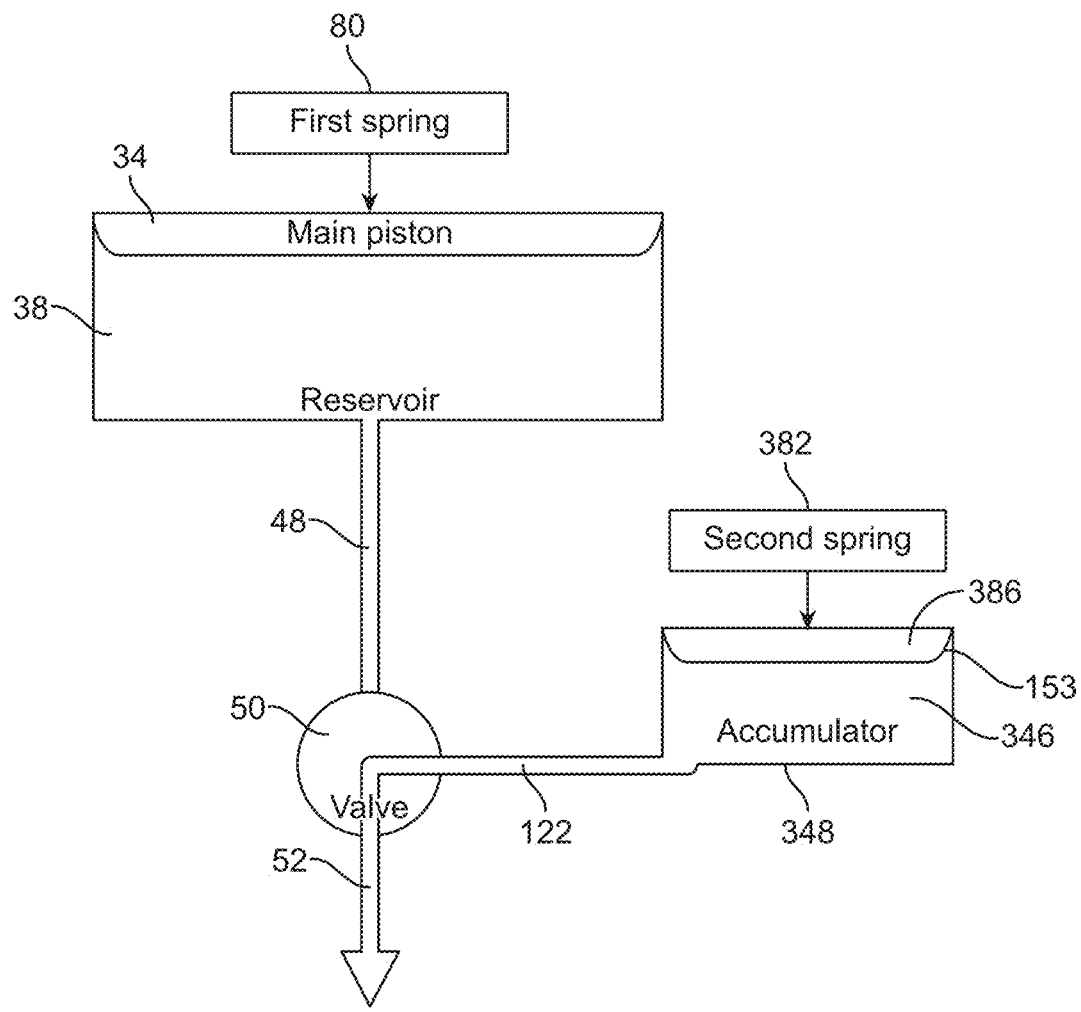

FIG. 4A shows a block diagram of a two-part bioactive agent delivery system for delivering multiple doses of a drug or other bioactive agent to a user with an inexpensive and easy-to-use system that reduces risk of accidental bioactive agent delivery or overdose, and FIG. 5 shows aspects of the disposable part of that embodiment. FIG. 4A shows in the reusable part 6 another embodiment of a valve driver for controlling a valve in a bioactive agent delivery system. FIG. 4A shows valve driver 13 with motor 94, gearbox 90, and clutch 58. FIG. 4A shows motor 94 (such as a DC or other motor) driving 4-stage planetary gearbox 90 to rotate valve core 406 in valve body 74. Such a driver may generate relatively more torque and a higher turn angle, while having a relatively low current draw and low total energy usage.

In particular, FIGS. 4A and 5 show an embodiment of the disposable part with a two spring system. As described above for FIG. 1, the system generally operates based on passive pressurization that drives bioactive agent flow through the system. In this embodiment, a spring 382 acts on a movable piston 386 to apply pressure to the contents of bolus chamber 346. A valve driver 13 in reusable part 6 moves valve 50 from a position in which the outlet of pressurized reservoir 38 communicates with bolus chamber 346 to a position in which bolus chamber 346 communicates with outlet 54. When bolus chamber 346 is in communication with reservoir 38, piston 386 moves against the action of spring 382 to allow bolus chamber 346 to fill. When bolus chamber 346 is in communication with outlet 54, spring 382 moves piston 386 to dispense the contents of bolus chamber 346 to the outlet. A seal 153 surrounds the edge of piston 386. Other elements of this embodiment are the same as in the embodiment of FIG. 1.

In some variations, and in comparison with the hydraulic embodiment described above, this two-spring embodiment has lower friction due to having one fewer sliding seals (e.g., a first seal but not a second seal) on piston 386, and the system can function at a lower (initial) pressure. Such a variation may allow use of a relatively weaker main reservoir spring. This may be useful, for example, for reducing structural load on the reusable part (e.g., reducing spring force on the housing). Such a variation may also make it easier (e.g., for the user) to insert the disposable part into the reusable part.

Figure 4B:
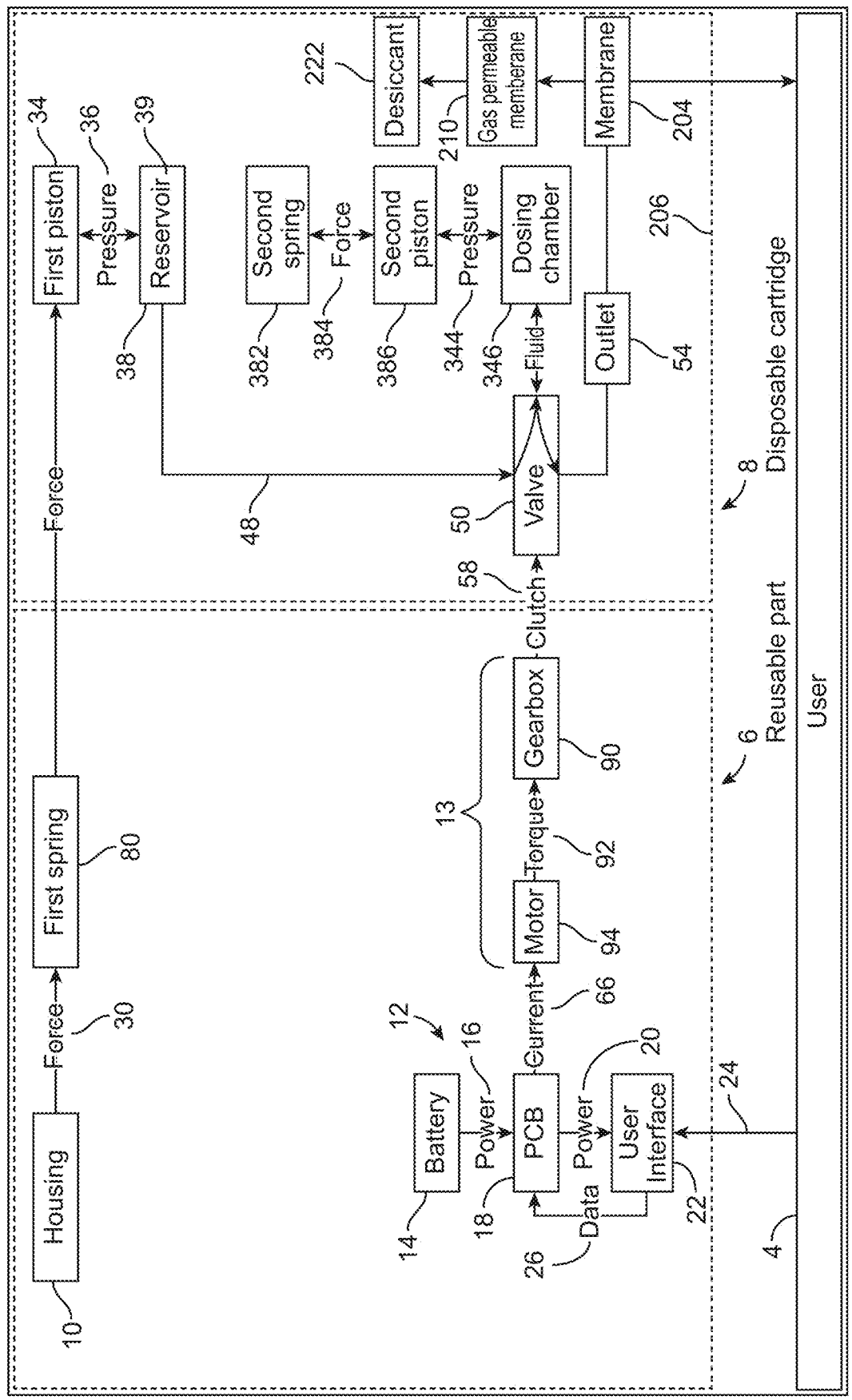
FIG. 4B shows a block diagram of a two-part bioactive agent delivery system where the disposable portion has a transdermal patch and a solvent recovery mechanism.

FIG. 4B shows a system similar to that of FIG. 4A but adding transdermal delivery and solvent recovery features that can be used for transdermal delivery of bioactive agent to the user 4. A transdermal delivery system may be as described in U.S. Pat. No. 8,440,221 to Zumbrunn et al., U.S. 2014/0207047 to DiPierro et al. or as known in the art. A bioactive agent for transdermal delivery may be any those described elsewhere herein or as known in the art.

FIG. 4B shows bolus chamber 346 configured to deliver bioactive agent to outlet 54 and to transdermal delivery membrane 204. A bioactive agent may be dissolved in a solvent for delivery to a user, and the rate of transdermal delivery of the bioactive agent may be controlled by moving solvent to control the concentration of the bioactive agent solution. This embodiment therefore includes a solvent removal feature including, e.g., an absorbent or a desiccant for removing solvent from the solution in or above the transdermal membrane 204. A gas permeable membrane 210 permits gaseous solvent to pass through to the desiccant 222 but does not allow the liquid bioactive agent solution to pass. Skin delivery membrane 204 is generally a porous membrane such as a polypropylene or other substrate such as described herein or as known in the art that transfers bioactive agent to the skin, generally contacting the skin of user 4 to facilitate transfer. In some examples, removing solvent may dry skin delivery member 204, preventing (further) bioactive agent transfer to user 4 and thus removing solvent may be a mechanism to stop bioactive agent delivery to user 4. In some examples, bioactive agent from a first dose may move across skin of user 4 and leave solvent behind. Thus, when bioactive agent from a second dose is delivered to the transdermal delivery membrane, the concentration of bioactive agent in the second dose may be diluted by solvent remaining in and around the transdermal delivery membrane from the first dose.

An absorbent for use with a transdermal patch as described herein may be an absorbent gel, blotting paper, paper, other polymer, silica gel or other material that readily soaks up or holds a fluid media such as a solvent liquid or vapor. An absorbent generally behaves as a physical sponge. An absorbent may be any structure or shape such as a single piece or a plurality of pieces. An absorbent may be an amorphous material or a formed material, and may be a block, a layer, a sheet, a plurality of sheets, a plurality of particles and so on. A desiccant may be used instead or in addition to the absorbent.

A solvent for a bioactive agent may include a single component or multiple components such as alcohol, water, or another solvent that readily vaporizes. One or more than one component may vaporize and be absorbed by absorbent. A vapor/gas permeable membrane may contain discrete pores that extend from one side of the membrane to the other side and allow gas to flow through. The size of these pores generally varies within a given membrane. In some examples, average or effective pore size in gas permeable membrane 210 may be at least 1 µm, at least 2 µm, at least 3 µm, at least 4 µm, at least 5 µm, at least 6 µm, at least 7 µm, at least 8 µm, at least 9 µm, at least 10 µm, at least 15 µm, at least 20 µm, or at least 30 µm. In some examples, maximum or average pore size in membrane 205 may be less than 30 µm, less than 20 µm, less than 16 µm, less than 15 µm, less than 10 µm, less than 9 µm, less than 8 µm, less than 7 µm, less than 6 µm, less than 5 µm, less than 4 µm, less than 3 µm or less than 2 µm or in between any of these amounts (such as at least 1 µm but less than 16 µm, at least 2 µm and less than 15 µm, etc.).

As mentioned above, it is generally desirable to prevent or minimize liquid flow through gas permeable membrane 210 (e.g., from the transdermal delivery membrane to the absorbent and/or desiccant). Pressure (such as pressure from bioactive agent delivery from outlet 54) may be sufficient to force liquid through a gas permeable membrane. Thus, a bioactive agent delivery system pressure and a membrane with an appropriate pore size may be chosen to allow vapor to flow through the membrane but effectively prevent liquid (e.g., a solvent) from flowing through. For example, bubble point test that tests the integrity of a membrane can be used to determine maximum pore size in a membrane. A bubble point test generally determines the minimum pressure, for a given wetted membrane, at which bubbles of air flow through the wetted membrane. A bubble point test may be performed using, for example, American Society for Testing and Materials Standard (ASTM) Method F316-03(2011) or another test. In some examples, the pressure of bioactive agent released by the bioactive agent delivery system is below the bubble point of gas permeable membrane 210.

Figure 6:
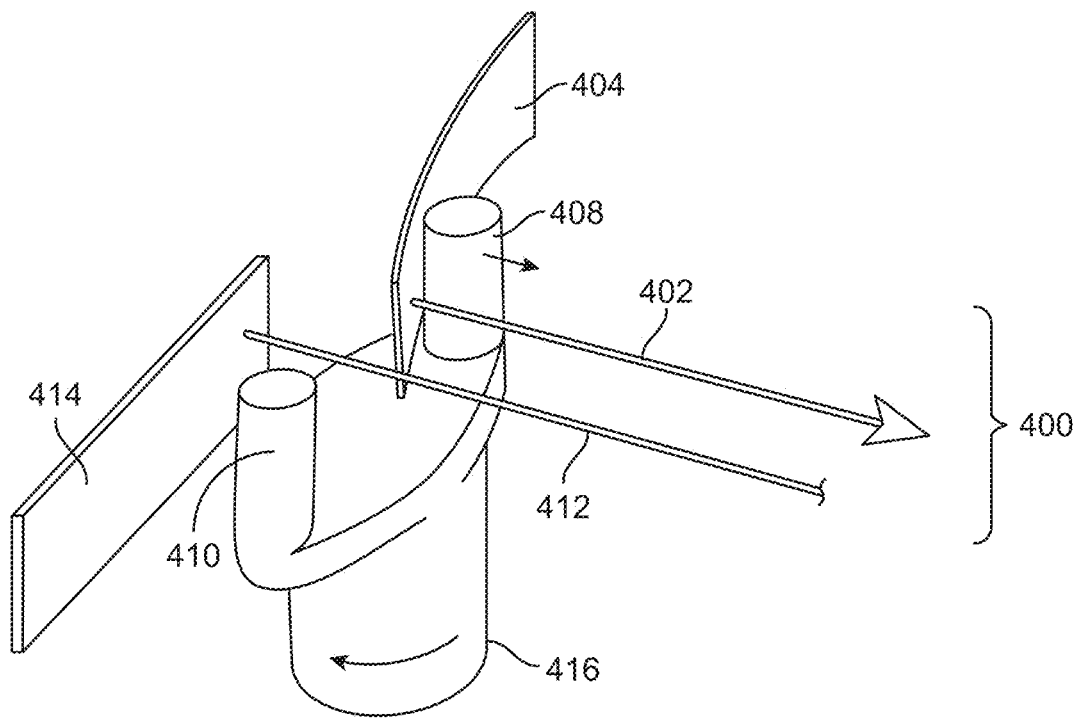
FIG. 6 shows a shape-memory valve driver that can be used in a two-part bioactive agent delivery system.

FIG. 6 shows an embodiment of a shape-memory valve driver for use in the reusable part, and a valve plug for use in the disposable part, of a two-part bioactive agent delivery system according to this invention. Valve plug 416 corresponds to valve 50 in the disposable part described in the embodiments above. Extending from valve plug 416 are first pin 408 and second pin 410 that are adapted to extend from the disposable part into the reusable part of the two-part delivery system when the two parts are connected.

FIG. 6 also shows valve driver 400 (corresponding to valve driver 13 described in earlier embodiments) with first wire 402 made of a shape memory allow, a second wire 412 also made of a shape memory alloy, leaf spring 404, and leaf spring 414, all of which are disposed in the reusable part of the two-part delivery system. First wire 402 is configured to act on spring 404 and second wire 412 is configured to act on spring 414. In response to a signal from the system's electronics apparatus to fill a bolus chamber with a dose of bioactive agent, electrical current from the electronics apparatus passes through first wire 402 which heats and shortens first wire 402, which in turn bends spring 404 to move and rotate first pin 408 on valve plug 416 into a first position (e.g., opening a flow path through the valve between a pressurized reservoir and the bolus chamber). When the electrical current ceases, first wire 402 cools and lengthens, and spring 404 returns to its first position. Due to internal friction, however, valve plug 416 remains in the position it is in until second wire 412 is heated. When a dose of bioactive agent should be sent to user, electrical current is sent to second wire 412, which heats second wire 412, pulling second pin 410 of valve plug 466 into a second position and opening a flow path between the bolus chamber and the delivery system outlet, simultaneously closing the flow path between the bolus chamber and the reservoir. Spring 404 and spring 414 may be leaf springs, a resilient polymer or another material as long as it is movable by the wires and can rotate the valve plug. First wire 402 and second wire 412 can be made from a shape-memory material or another material as long as they can respond to a current and move (respectively) spring and spring.

Figure 7:
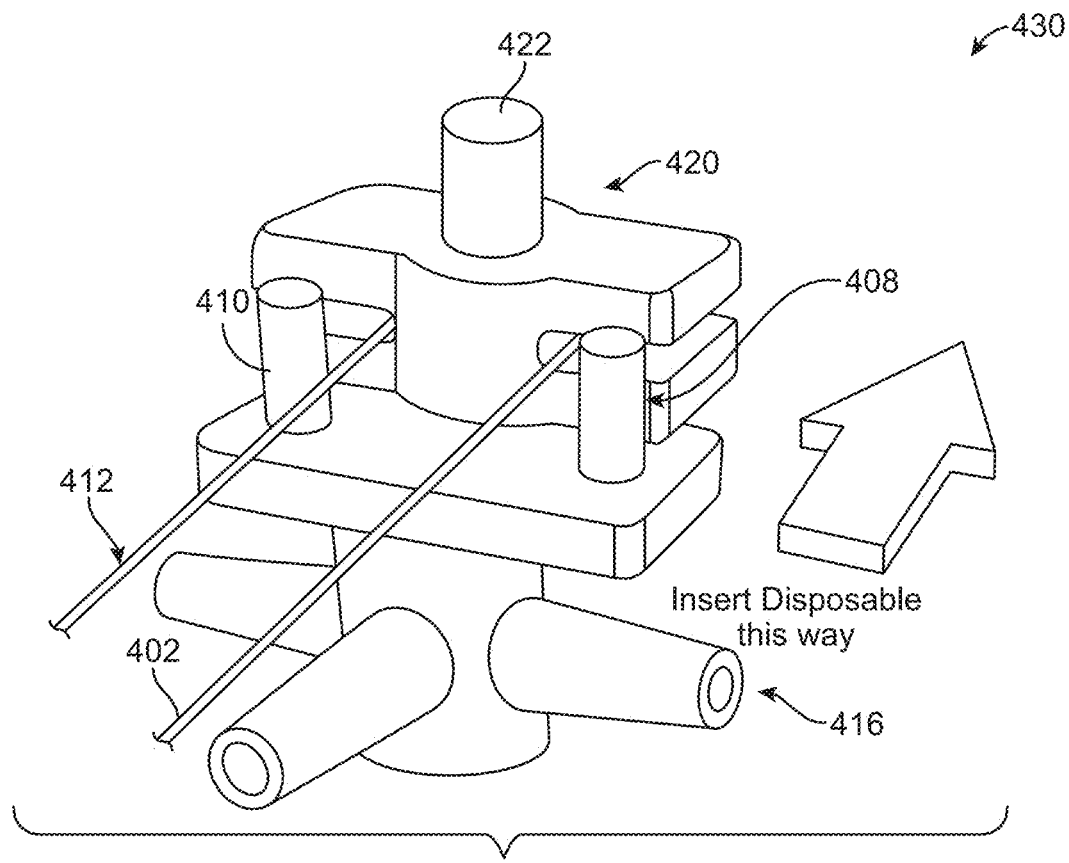
FIG. 7 shows a shape-memory valve driver part that can be used in a two-part bioactive agent delivery system such as the system shown in FIG. 1.

FIG. 7 shows another embodiment of a shape-memory valve driver 430 for use in a two-part bioactive agent delivery system. As in the embodiment of FIG. 6, extending from a valve body 416 in a disposable part are pins 408 and 410. Pins 408 and 410 may be inserted into the reusable part of the two-part system to engage a rotor 420 configured to rotate about a shaft 422 mounted within the housing of the reusable part of the system. Shape memory alloy wires 402 and 412 may be selectively energized to shorten wire 402 or wire 412 to move the valve plug 416 from one position to another, as described above.

Figure 8:
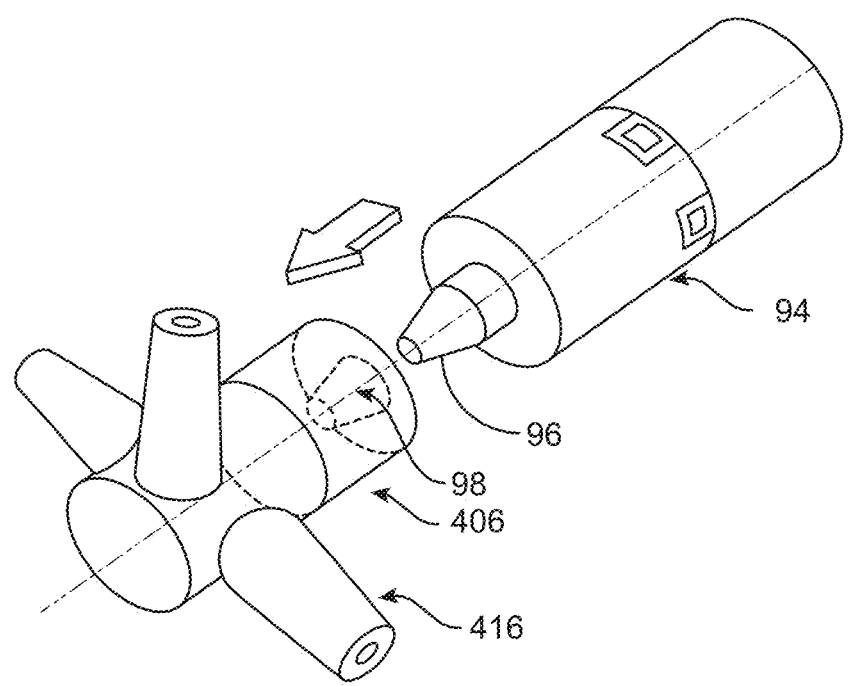
FIG. 8 shows a motorized valve driver that can be used in a two-part bioactive agent delivery system.

FIG. 8 shows another embodiment of a valve driver for a two-part bioactive agent delivery system. A motor 94 within the reusable part of the two-part system may be activated to turn a drive shaft 96 extending from the reusable part into a corresponding fitting 98 in the valve body 416 in the disposable part. As shown, the fit between shaft 96 and fitting 98 is tapered. A motor and corresponding valve may be configured to have rotational alignment or to not have rotational alignment. In some examples, rotational alignment is not required and the motor and valve core can be fitted together in any orientation relative to one another. In some examples, a valve driver may have a feature (such as a spline) to aid in rotational alignment between the valve driver and valve. A valve may also or instead have a feature (such as a groove) to aid in rotational alignment with the valve driver. A conical fit may be more tamper-resistant. A valve driver with a motor may be especially useful in a wearable or portable bioactive agent delivery system.

FIGS. 9A-9E show one embodiment of a bioactive agent delivery system with reusable part 6 and a disposable part 8 such as described in FIG. 1 above. The reusable part 6 includes a housing 10 containing valve driver 13, spring 28, spring 53 and the control electronics. Disposable part 8 has the dosing or bolus chamber 46, the piston 51 for the bolus chamber, reservoir 38, reservoir piston 34 and valve 50. In this example, the parts of the two-part delivery system that come into contact with bioactive agent are in disposable part 8.

Figure 10:
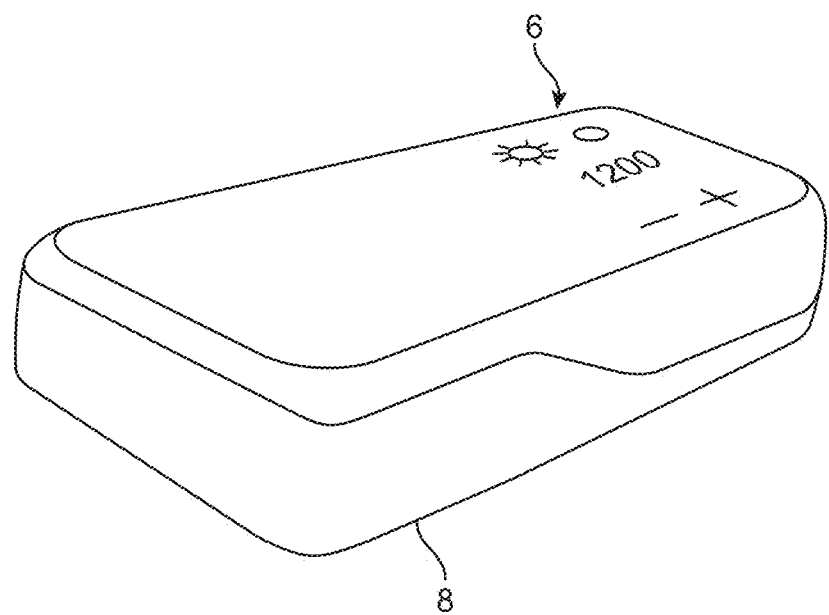
FIG. 10 is a perspective view of a two-part bioactive agent delivery system according to an embodiment of the invention.

FIG. 10 shows another embodiment of a two-part bioactive agent delivery system such as described in FIG. 1 with reusable part 6 and disposable part 8 that mate and work together. In general the reusable part 6 and disposable part 8 are configured to be readily separable from each other so that a first disposable part can be removed from the reusable part, and the reusable part can be used with a second disposable part.

Figure 11A:
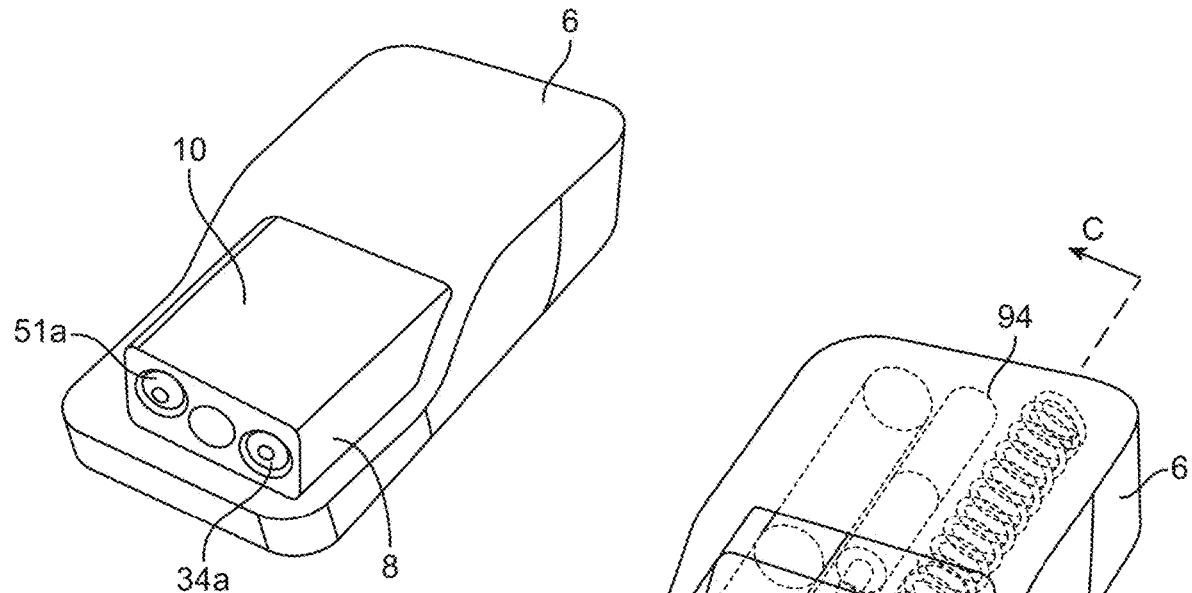
FIGS. 11A-11C show different views of the reusable portion of the two-part bioactive agent delivery system of FIG. 10.
Figure 11B:
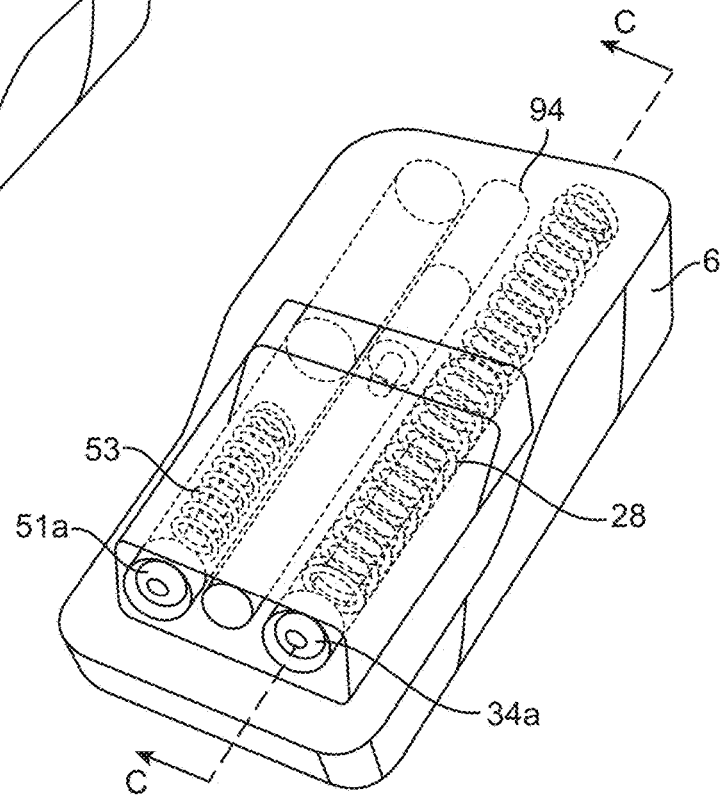
Figure 11C:
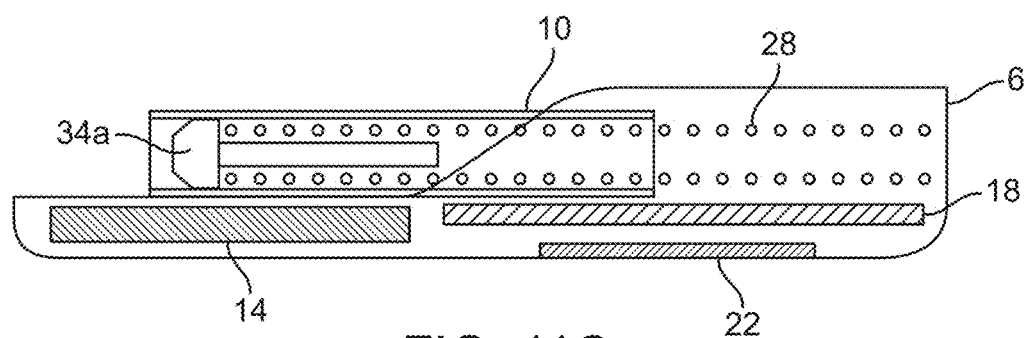

FIGS. 11A-C show yet another embodiment of a two-part bioactive agent delivery system. FIG. 11A shows a perspective view of the assembled delivery system showing disposable part 8 inserted beneath a shroud or housing 10 of reusable part 6. FIG. 11B shows a partially cut away perspective view of the reusable part 6 in this embodiment with a reservoir spring 28, a reservoir plunger 34a (for interacting with the piston in the reservoir in the disposable part), a bolus chamber spring 53, a bolus chamber plunger 51a (for interacting with the piston of the bolus chamber in the disposable part) valve motor 94 for turning a valve in the disposable part to control bioactive agent delivery between the reservoir and bolus chamber, and between the bolus chamber and the system outlet. FIG. 11C shows a side longitudinal view of the bioactive agent delivery system showing many of the same elements of the reusable part 6 along with some of the system electronics, such as battery 14, PCB 18, and user interface 22.

Figure 12:
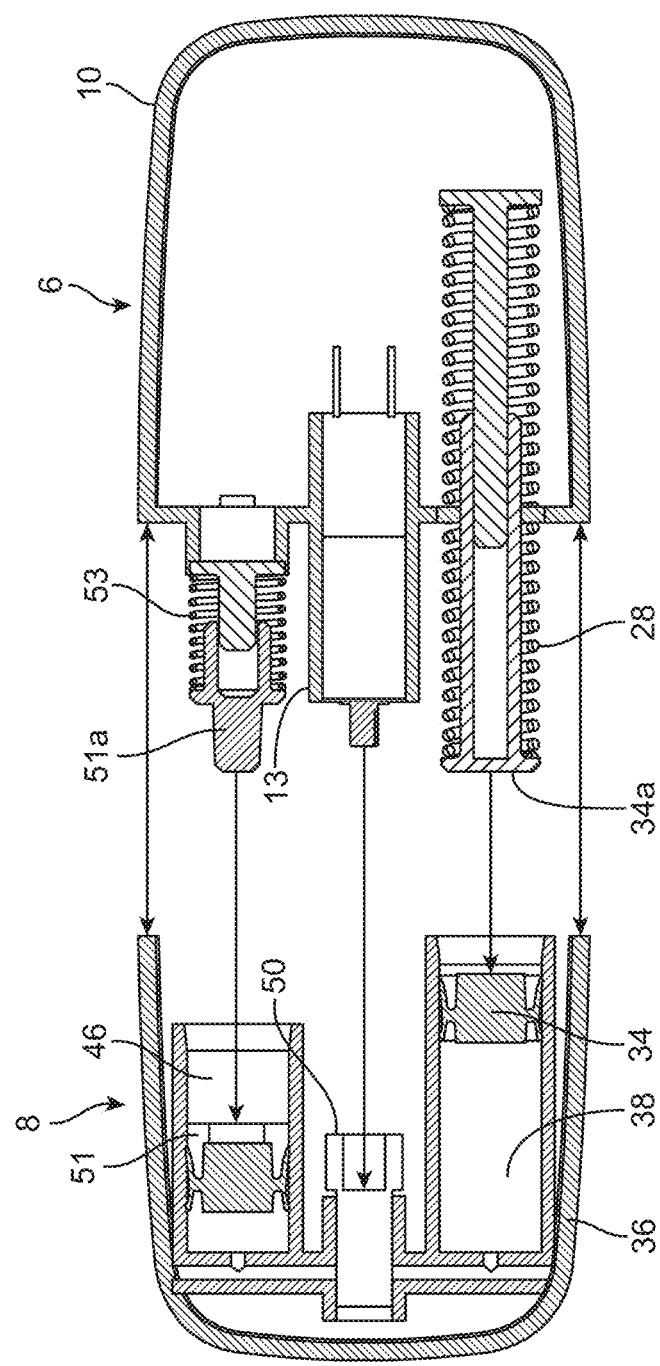
FIG. 12 is a sectional view of an embodiment of a disposable part and reusable part of a bioactive agent delivery system.

FIG. 12 shows another embodiment of a two-part bioactive agent delivery system according to this invention. As shown, disposable part 8 has not yet been connected to reusable part 6. Arrows in FIG. 12 show how housing 36 of disposable part 8 will align with housing 10 of reusable part 6 to engage bolus chamber plunger 51a (biased by spring 53) with bolus chamber piston 51 in bolus chamber 46, reservoir plunger 34a (biased by spring 28) with reservoir piston 34 in reservoir 38, and valve driver 13 with valve 50. Springs 28 and 53 compress when disposable part 8 connects to reusable part 6, as discussed above.

Figure 13:
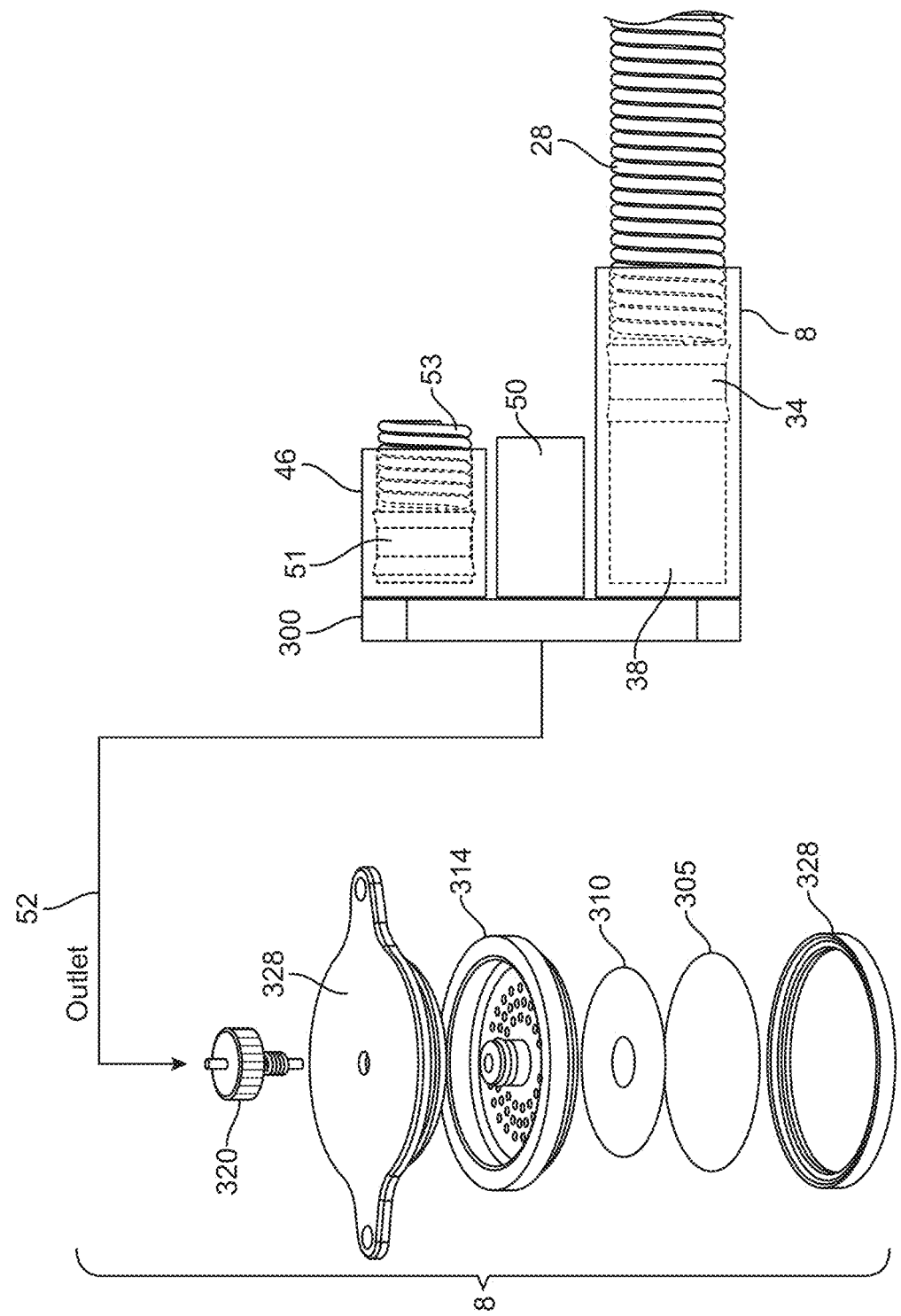
FIG. 13 is an exploded view showing aspects of a disposable part with a transdermal patch and solvent recovery mechanism for delivering bioactive agent to a user.
Figure 14B:
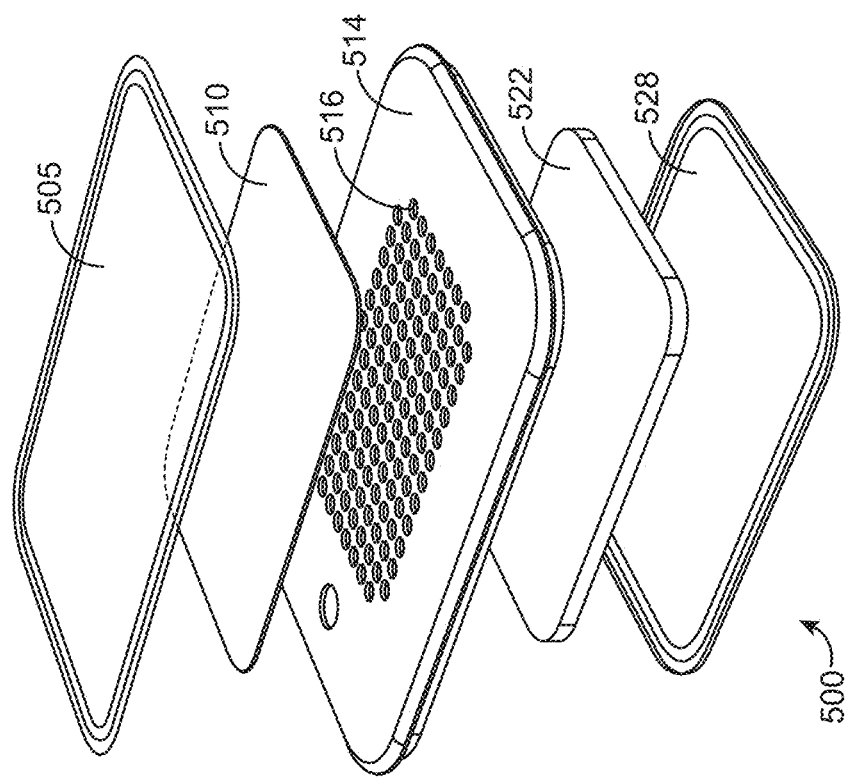
FIGS. 14A-14D show aspects of a transdermal patch and a solvent recovery mechanism for use in a two-part bioactive agent delivery system, such as that shown in FIG. 15.
Figure 14A:
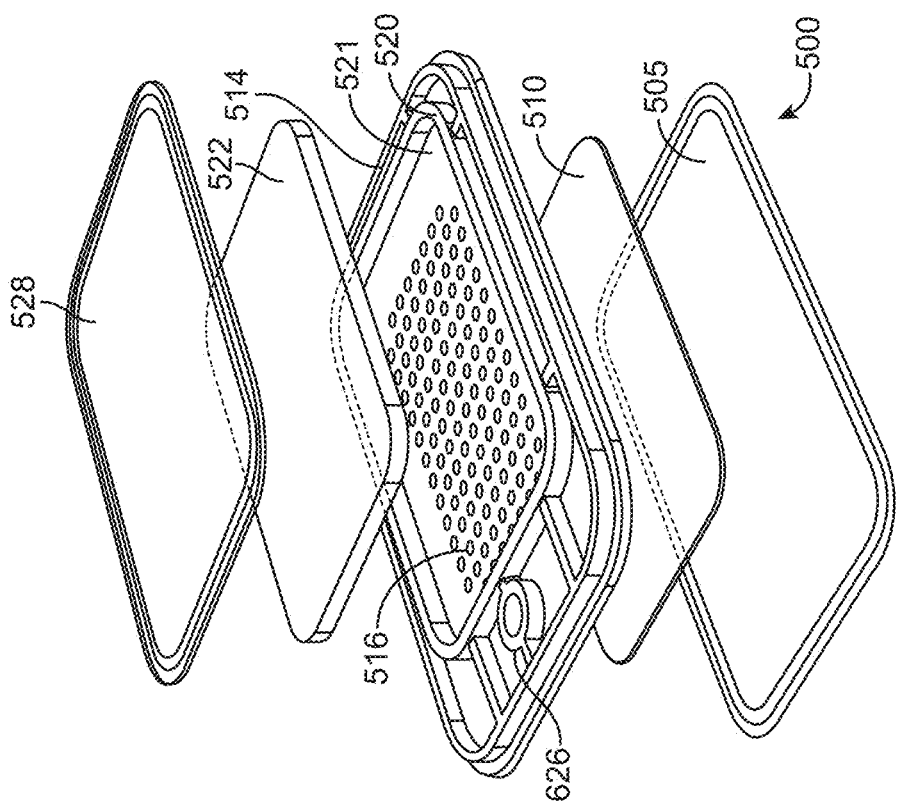
Figure 14C:
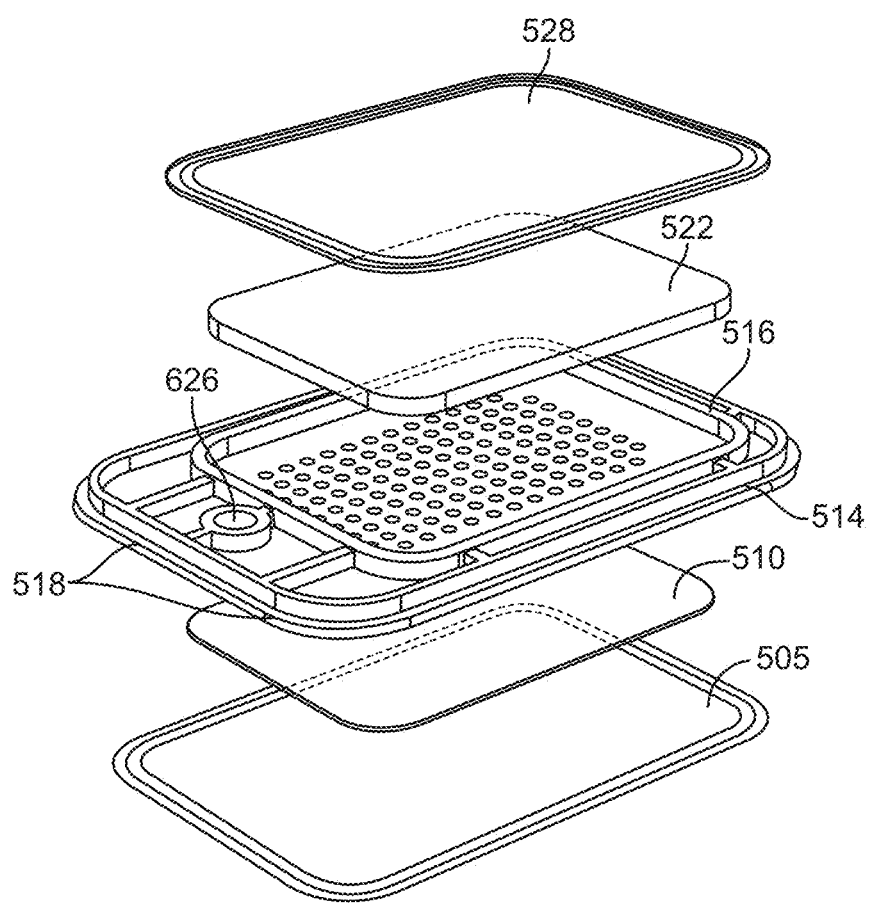
Figure 14D:
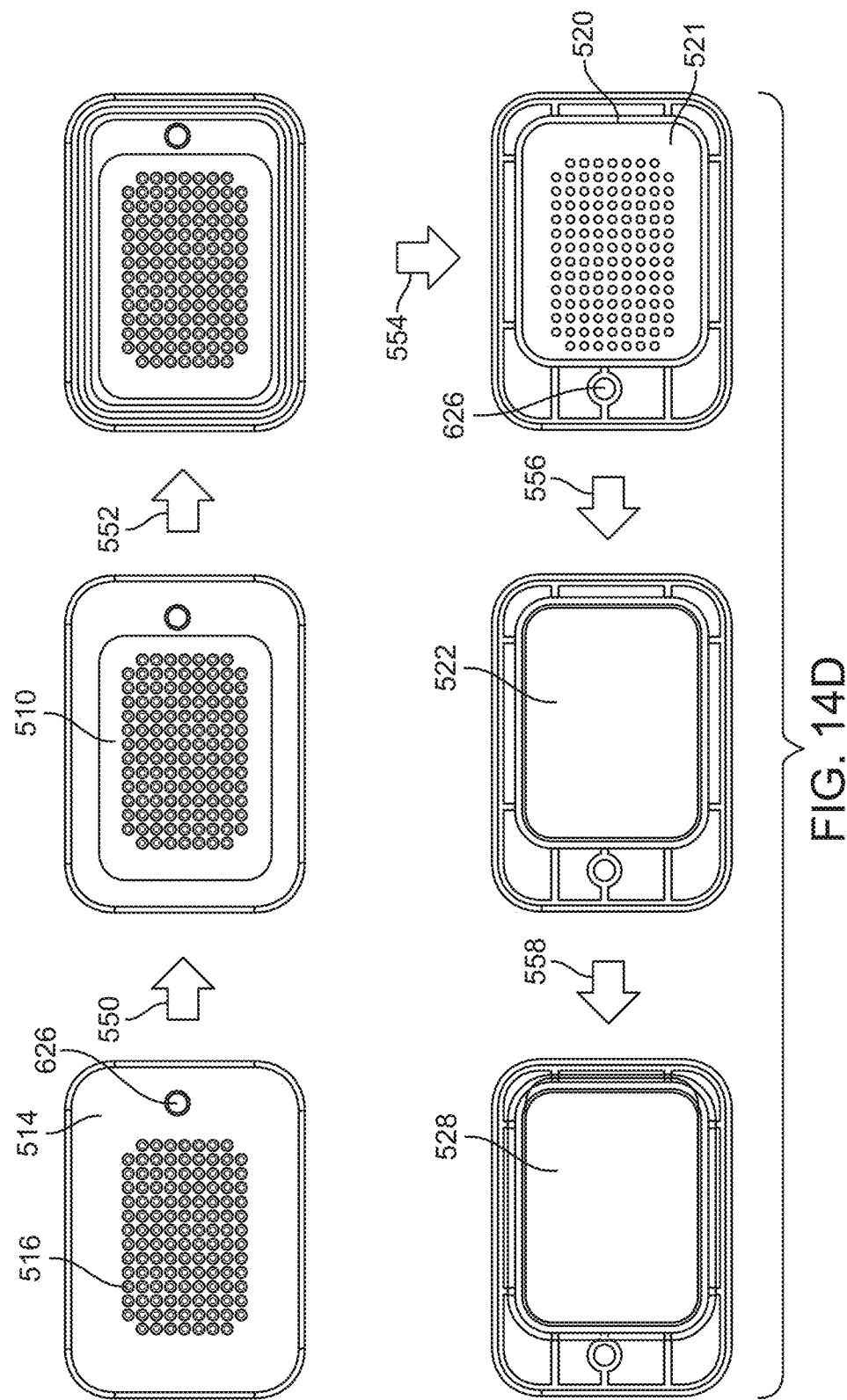

FIG. 13 shows an embodiment adding components of a transdermal bioactive agent delivery system with solvent recovery to e.g., the embodiment of FIG. 12. Springs 28 and 53 of the reusable part are shown engaging pistons 34 and 52, respectively, of the disposable part 8. The disposable part 8 also includes a manifold 300, which provides the fluid paths between the valve 50 and the reservoir 38, between the valve 50 and the bolus chamber 46, and between the valve 50 and the outlet. An outlet path 52 leads to a fitting 320 with a fluid flow channel that passes through openings in the centers of a solvent recovery chamber 328 (containing, e.g., a desiccant), a spacer 314 with a plurality of openings, and a gas-permeable membrane 310 to reach a transdermal membrane 305. A support ring 328 provides support to the structure. As described earlier, vaporized solvent from the bioactive agent solution can pass from the wetted transdermal membrane 305 through gas-permeable membrane 320 and the openings in spacer 314 to enter the solvent recovery chamber. The rate and timing of transdermal bioactive agent delivery can be controlled, e.g., by balancing the timing and the delivery rate of the bioactive agent solution from the bolus chamber with the amount of desiccant in the solvent recovery chamber and/or the permeability of the gas permeable membrane.

Transdermal patch 305 may be any appropriate material(s) or have any appropriate characteristics that can transfer active agent across the membrane. A membrane may be hydrophilic or hydrophobic. A membrane may have pores (as described in more detail below), such as from 0.010-0.01 um (e.g., from 0.02 um-0.05 um, etc.). A membrane may have porosity over 20%-60% (e.g., from 30%-50%, from 45% to 50%, etc.). In a particular example a polypropylene such as Celgard 2400 polypropylene (e.g., with a thickness around 25 um such as between 1 urn and 100 um, with a pore size around 0.043 such as from 0.005 to 0.2 um, etc. may be used). A material may be chosen based on the bioactive agent, length of treatment, etc. A patch and bioactive agent delivery system may be configured to deliver effective membrane wetting of a skin delivery membrane. Membrane wetting refers to the extent to which pores in a membrane are penetrated by a fluid (e.g., displacing a media such as air in pores in the membrane with a fluid, in this example with bioactive agent). Effective wetting may include how quickly a membrane is wetted, a % of wetting, etc. Effective wetting may be, for example, faster wetting which may allow faster transfer of active agent across a skin delivery membrane. Effective wetting may be, for example, more complete wetting (e.g., a greater number or percent pores in a membrane are wetted). Effective membrane wetting is generally useful as it allows faster and/or more complete active agent fluid transfer across the membrane for delivery to the user. Membrane wetting may occur in less than 5 seconds, less than 4 seconds, less than 3 seconds, less than 2 seconds, less than 1 second, less than 0.5 seconds. Bioactive agent transfer across skin delivery membrane 305 to/through a user's skin is facilitated by bioactive agent being dissolved in or otherwise transportable by a solvent. When multiple doses of bioactive agent are delivered to a user over time from a single disposable part an excess amount of solvent (e.g., solvent from each dose) may collect (build up) in the system, e.g., in fluid space 202. Excess solvent in the fluid space (or membrane) will dilute bioactive agent concentration in a subsequent dose of bioactive agent received into the fluid space (or membrane).

FIGS. 14A-14D and FIGS. 15A-E show an embodiment of a disposable part that can be used along with a reusable part to transdermally deliver a bioactive agent. As in the embodiments described above, the disposable part houses the bioactive agent reservoir, bolus chamber and valve. The disposable part receives a force from a reusable part to pressurize the bioactive agent, and the reusable part controls movement of the valve to deliver the bioactive agent to a transdermal membrane.

FIGS. 15A-B show manifold 680 of disposable part 608 for holding and fluidly connecting reservoir 638, valve 650, and dosing or bolus chamber 646. Valve 650 is a three-way valve having a movable valve core 674 as described above. As described above, valve core 650 can be in a first position or a second position. When valve 650 is in a first position, a flow path open between bolus chamber 646 and the system outlet (and to the transdermal patch and user); the flow path is closed between reservoir 638 and bolus chamber 646. When valve 650 is in a second position, a flow path between reservoir 638 and dosing or bolus chamber 646 is open, and the flow path is closed between bolus chamber 646 and the outlet is closed. As described above, there is no direct pathway for bioactive agent flow from reservoir 638 to the outlet, minimizing the risk of unintentional bioactive agent flow or overdose. The housing 636 of the disposable part 608 is also shown. FIG. 15B is an exploded view of disposable part 608 showing the reservoir 638, reservoir piston 634, bolus chamber 646, bolus chamber piston 651, valve core 674 and manifold 680. FIG. 15B also shows the transdermal membrane and solvent recovery elements at the system outlet (described in more detail with respect to FIGS. 14A-D).

Figure 15C:
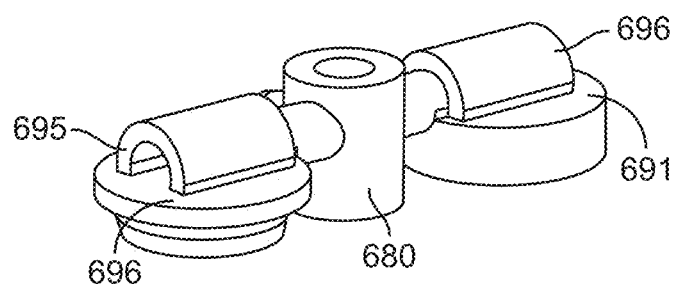
Figure 15D:
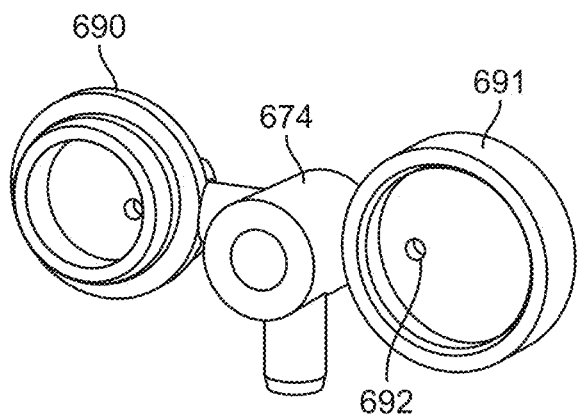
Figure 15E:
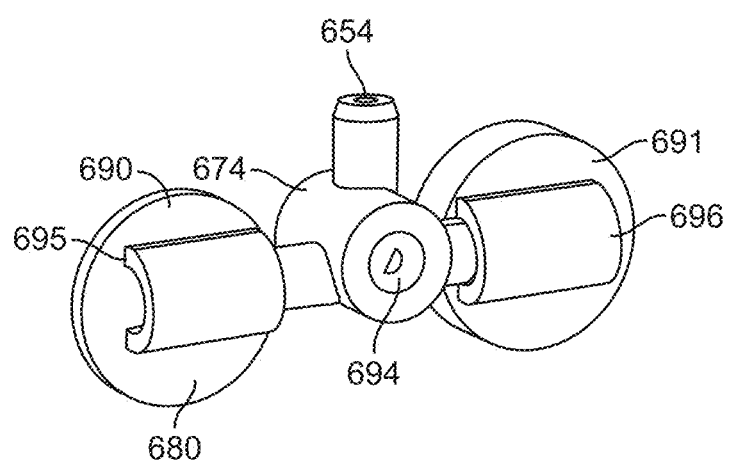
Figure 16B:
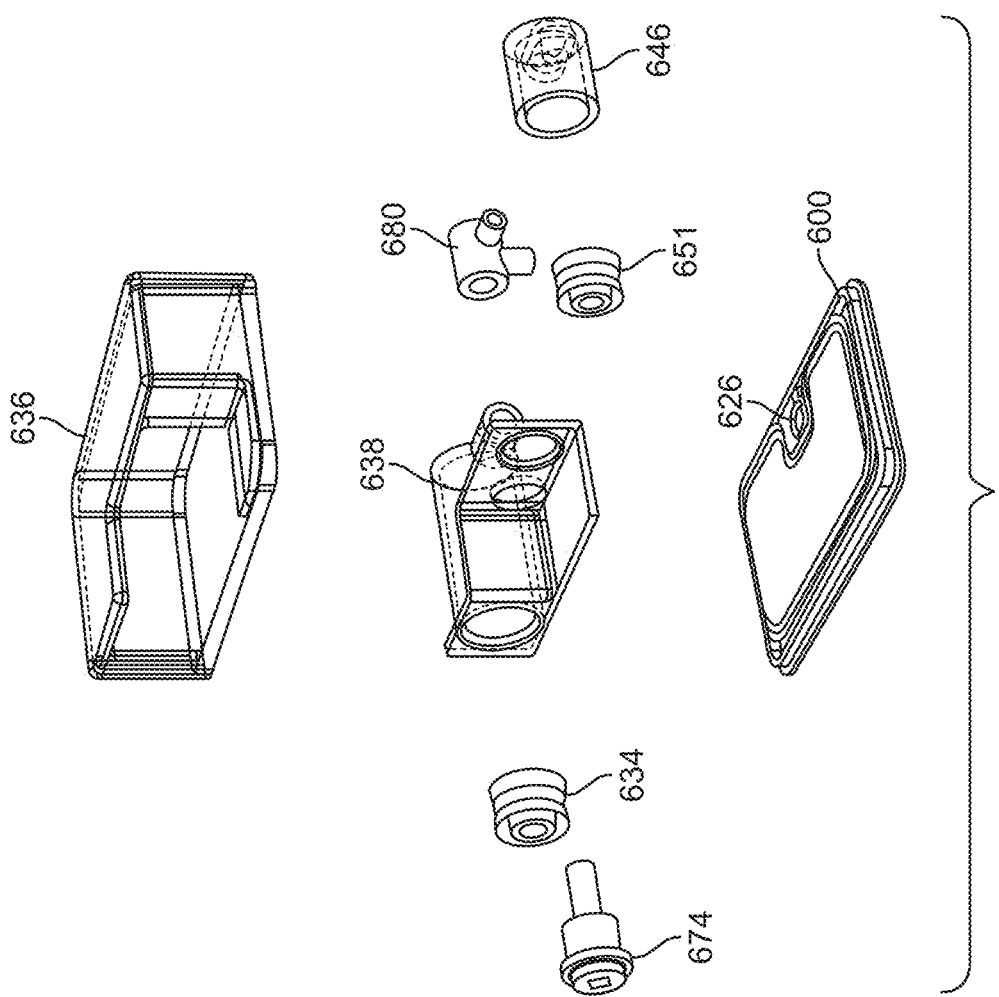
FIGS. 16A-16B show yet another embodiment of a disposable portion for use with a two-part transdermal bioactive agent delivery system.
Figure 16A:
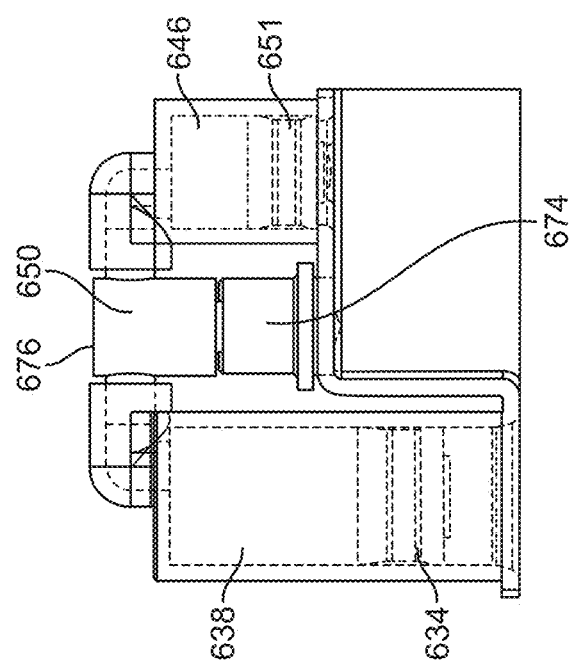

FIGS. 15C-E show different views of manifold 680. Manifold includes valve body 676 configured to receive valve core 674, end cap 690 for capping reservoir 638 and end cap 691 for capping bolus chamber 646. Manifold 680 also includes first side port 695 and second side port 696 which may be useful for delivering (loading) bioactive agent to reservoir 638 and bolus chamber 646, respectively, through fluid vents in the end caps, such as fluid vent 692. (In some variations, a manifold may have zero, one, two or more than two loading ports). FIG. 15E shows an air vent 694 of valve 50 that can be used to bleed air from the system during manufacturing.

FIGS. 14A-14D show exploded views of an embodiment of a transdermal membrane and solvent recovery system for use at the outlet of the bioactive agent delivery system, such as a two-part bioactive agent delivery system along the lines discussed above with respect of FIG. 15. FIGS. 14A and 14C show exploded top views, and FIG. 14B shows an exploded bottom view. FIGS. 14C and 14D show one example of how the transdermal patch shown in FIGS. 14A-14B can be assembled.

In this embodiment, transdermal membrane and solvent recovery system 500 includes a backing 528 covering an absorbent or desiccant 522 within a chamber 521 formed by a ridge 520 in support structure 514. Openings 516 in support structure 514 communicate with a gas permeable membrane 510 covering a transdermal membrane 505. The outlet of the valve 650 described above with respect to FIG. 15 communicates with opening 626 in support structure 514 to deliver a solution of bioactive agent to transdermal membrane 505. Solvent from the bioactive agent solution may evaporate and pass through gas-permeable membrane 510 to be absorbed by absorbent or desiccant 522.

FIGS. 14C and 14D show how transdermal membrane 500 can be assembled. Gas permeable member 510 is layered between transdermal membrane 505 and attached to support structure 514. Part or essentially all of gas permeable member 510 may be attached to support structure 514. Edge 518 of support structure 514 is attached to (sealed with) edge 506 of transdermal membrane 505 to enclose or contain gas permeable membrane 510. First step 550 shows gas permeable membrane 510 placed over the central portion of the top side of support structure 514. Gas permeable membrane 510 is attached to support structure 514 such as by ultrasonic welding or another appropriate method. Second step 552 shows transdermal membrane 505 placed over gas permeable membrane 510 on support structure 514, and connected to support structure 514 at its edges such as by heat and ultrasonic welding or another appropriate method. Third step 554 shows the bottom side of support structure 514 with chamber 521 surrounded by rim 520. Fourth step 556 shows absorbent 522 placed in chamber 521. Fifth step 558 shows backing 528 placed over absorbent on support structure 514. Backing 528 is attached to support structure 514 at rim 520 such as by ultrasonic welding or another appropriate method. Although shown as generally rectangular with rounded edges, transdermal membrane and solvent recovery element 500 and any other transdermal patches described herein or used with a bioactive delivery system as described herein for delivering bioactive agent to a user may have any shape able to deliver bioactive agent to a user, such as circular, ellipsoid, rectangular, round, rounded square, square, triangular, etc.

FIGS. 16A-B show another embodiment of the disposable part component of a two-part bioactive agent delivery system similar to that of FIG. 15 but with the bolus chamber 646 formed as a separate element, as shown best in the exploded view of FIG. 16B.

FIGS. 17A-17E show another embodiment of a disposable part for use with a two-part transdermal bioactive agent delivery system. Similar to the embodiments of FIGS. 14, 15 and 16, the disposable part houses the bioactive agent reservoir, bolus chamber and valve. The disposable part receives a force from a reusable part to pressurize the bioactive agent, and the reusable part controls movement of the valve to deliver the bioactive agent to a transdermal membrane.

FIGS. 17A-B show reservoir 838, valve 850, valve core 876 (shown inside of valve body 850), and bolus chamber 846. Reservoir 838 includes piston 834 for pressurizing bioactive agent in the reservoir when a force is exerted on piston 834 by a reusable part of the two-part system. In this embodiment, the spring 882 biasing the bolus chamber piston 851 is in the disposable part, and it compresses when pressurized bioactive agent from the reservoir enters the bolus chamber. When valve core 876 is turned by the reusable part, valve 850 alternately connects reservoir 838 with bolus chamber 846 and bolus chamber 846 with a transdermal membrane, but it prevents a direct flow path between reservoir 838 and the transdermal membrane to reduce the risk of unintentional bioactive agent flow or overdose to a user. FIG. 17B also shows a housing 836 for housing these elements.

As shown in FIGS. 17C-E, the flow paths among the reservoir 838, valve 850 and bolus chamber 846 are formed in a structural support member 814. The outlet 848 of reservoir 838 leads to an opening 886 in the structural support member 814, and opening 886 leads to a flow path 888 formed in the support member 814. A seal 820 covers the opening 886 and flow path 888. Pressurized bioactive agent in flow path 888 moves through opening 884 and valve port 896 to enter the valve when the reusable part turns the valve core to the appropriate position. When the reusable part turns the valve core to its other position, pressurized bioactive agent exits the bolus chamber through valve port 895 and opening 885 in structural support member 814 to reach transdermal membrane 805.

In this embodiment, the system includes a solvent recovery system with a backing 830 covering an absorbent or desiccant 822 within a chamber 821 formed by a ridge 819 in support structure 814. Openings 816 in support structure 814 communicate with a gas permeable membrane 810 covering transdermal membrane 805. Solvent from the bioactive agent solution may evaporate and pass through gas-permeable membrane 810 to be absorbed by absorbent or desiccant 822.

The configuration shown in FIGS. 17A-E may have relatively simple parts for manufacture (such as by molding parts for assembly). Such a configuration may minimize the lengths of one or more flow paths and may minimize the amount of space contained in the flow path. A flow path length between a valve, outlet and/or delivery component such as between a bolus chamber, valve, or outlet and an outlet, delivery component, transdermal patch, fluid space of a transdermal patch, or skin delivery member of a transdermal patch may be configured to hold less than 5 μl, less than 4 μl, less than 3 μl, less than 2 μl, or less than 1 μl of fluid media. A relatively shorter flow path length from the bolus chamber to the outlet and skin delivery member may minimize the time for active agent to move from the bolus chamber to the outlet (or skin delivery member). For example, such amounts of air or other gas present in a flow path may decrease delivery speed or increase delivery time and reduce skin delivery member wetting efficiency. As described above, rapid bioactive agent movement may be important to obtain effective wetting.

FIGS. 18A-18C show yet another embodiment of a disposable part for use in a two-part transdermal bioactive agent delivery system. Similar to the embodiments of FIGS.

14-17, the disposable part houses the bioactive agent reservoir, bolus chamber and valve. The disposable part receives a force from a reusable part to pressurize the bioactive agent, and the reusable part controls movement of the valve to deliver the bioactive agent to a transdermal membrane. In this embodiment, the bolus chamber 946 and the reservoir 938 are molded as a single part.

FIGS. 18A-C reservoir 938, valve 950, valve core 976 (shown inside of valve body 950), and bolus chamber 946. Reservoir 938 includes piston 934 for pressurizing bioactive agent in the reservoir when a force is exerted on piston 934 by a reusable part of the two-part system. In this embodiment, the spring 982 biasing the bolus chamber piston 951 is in the disposable part, and it compresses when pressurized bioactive agent from the reservoir enters the bolus chamber. When valve core 976 is turned by the reusable part, valve 950 alternately connects reservoir 938 with bolus chamber 946 (via valve ports 948 and 995) and bolus chamber 946 with a transdermal membrane beneath support member 914 (via valve ports 995 and 996 and opening 986 in structural support 914), but it prevents a direct flow path between reservoir 938 and the transdermal membrane to reduce the risk of unintentional bioactive agent flow or overdose to a user. Housing 936 is provided for housing these elements.

In this embodiment, the system includes a solvent recovery system 928 similar to that described above with a backing covering an absorbent or desiccant within a chamber formed by a ridge in support structure 914.

FIGS. 19A-19F show different views of still another embodiment of a disposable part for use with a two-part transdermal bioactive agent delivery system. Similar to the embodiments of FIGS. 14-18, the disposable part houses the bioactive agent reservoir, bolus chamber and valve. The disposable part receives a force from a reusable part to pressurize the bioactive agent, and the reusable part controls movement of the valve to deliver the bioactive agent to a transdermal membrane. In this embodiment, the valve, bolus chamber and reservoir are molded as one part 1010, the manifold and desiccant housing 1012 are molded as another part, and the housing 1081 is the third part of the disposable part.

FIG. 19 show reservoir 1038, valve 1050, valve core 1076 (shown inside of valve body 1050), and bolus chamber 1046. Reservoir 1038 includes piston 1034 for pressurizing bioactive agent in the reservoir when a force is exerted on piston 1034 by a reusable part of the two-part system. In this embodiment, the spring (not shown) biasing the bolus chamber piston 1051 is in the disposable part, and it compresses when pressurized bioactive agent from the reservoir enters the bolus chamber. When valve core 1076 is turned by the reusable part, valve 1050 alternately connects reservoir 1038 with bolus chamber 1046 and bolus chamber 1046 with a transdermal membrane 1005, but it prevents a direct flow path between reservoir 1038 and the transdermal membrane to reduce the risk of unintentional bioactive agent flow or overdose to a user. FIG. 19B also shows a housing 1081 for housing these elements.

As shown in FIGS. 19, flow paths among the reservoir 1038, valve 1050 and bolus chamber 1046 are formed in a structural support member 1080. The outlet of reservoir 838 leads to openings 1084 and 1084a in the manifold housing 1012 and structural support member 1014, respectively, and opening 1084a leads to a flow path 1048 formed in the support member 1014. A seal 1020 covers the opening 1084a and flow path 1048. Pressurized bioactive agent in flow path 1048 moves through openings 1089a and 1089 to enter the valve, exits the valve and passes through openings 1085a and 1085, covered flow path 1049 and opening 1088 to enter the bolus chamber 1046 when the reusable part turns the valve core to the appropriate position. When the reusable part turns the valve core to its other position, pressurized bioactive agent exits the bolus chamber 1046 through the valve and openings 1088 and 1086 in structural support member 1014 and opening 1086a in manifold housing 1012 to reach transdermal membrane 1005.

This embodiment also includes a solvent recovery system. Desiccant 1022 is disposed in manifold housing 1012. An opening 1024 in desiccant 1022 communicates openings 1085 with 1085a and 1086 with 1086a. Openings 1016 in support structure 1014 communicate with a gas permeable membrane 1010 covering transdermal membrane 1005. Solvent from the bioactive agent solution may evaporate and pass through gas-permeable membrane 1010 to be absorbed by desiccant 1022.

FIGS. 20A-20E show different views of a two-part bioactive agent delivery system 1102 with disposable part 1108 connectable with reusable part 1106. System 1102 has a user interface 1122, such as for receiving a user's command or displaying a system parameter.

FIG. 20B shows a perspective view of disposable part 1108 being placed into reusable part 1106 to form the active agent delivery system shown in FIG. 20A. Disposable part 1108 has a housing 1110 and a transdermal membrane or patch (not shown) beneath the patch area 1100 of base 1101. Reusable part 1106 includes spring 1128 for pressurizing the reservoir 1138 in the disposable part and a spring 1112 for providing a force to the bolus chamber 1146 in disposable part 1108. Springs 1112 and 1128 are compressed and loaded when reusable part 1106 is connected to disposable part 1108.

Figure 20C:
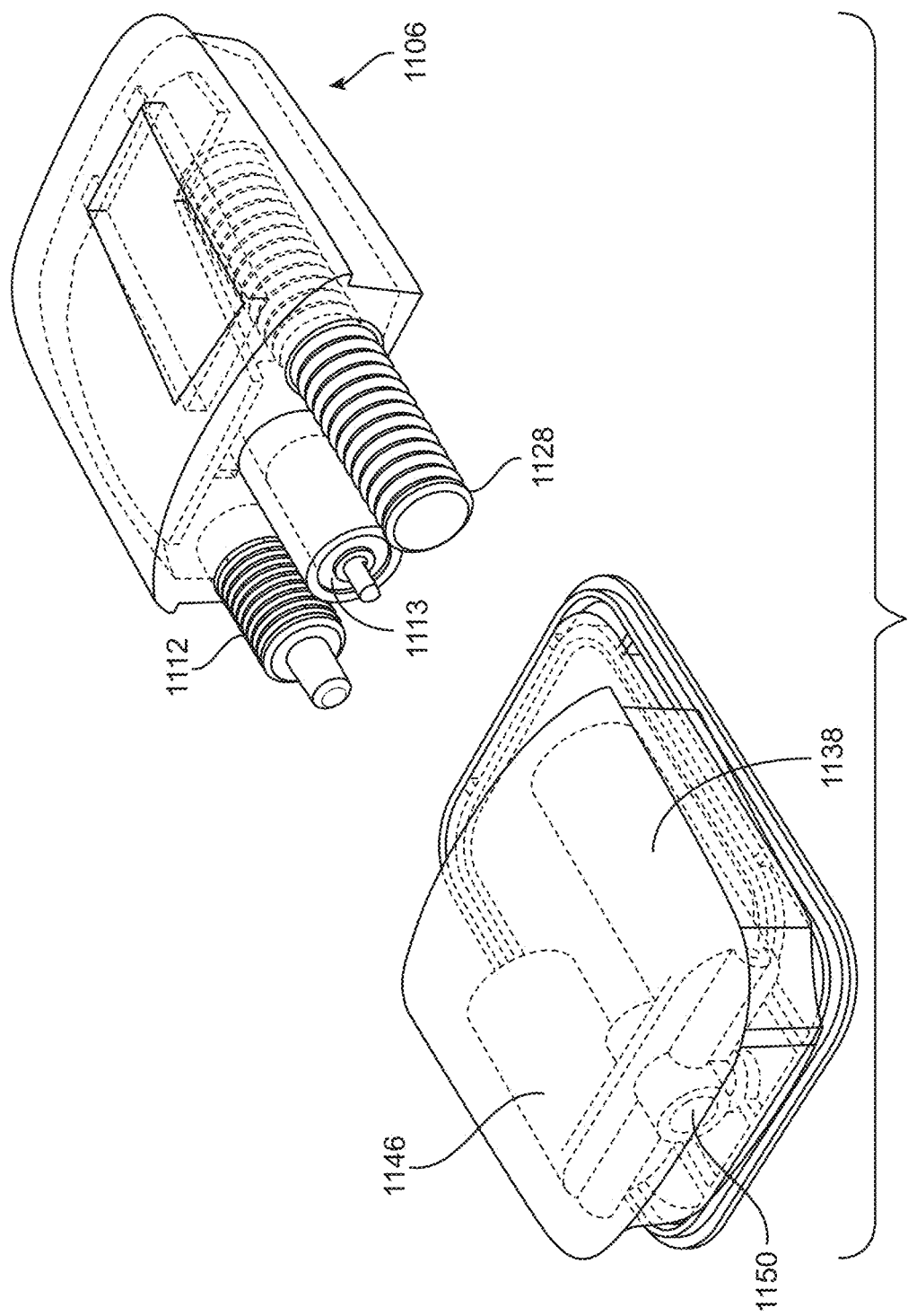

FIG. 20C also shows that valve driver 1113 in reusable part 1106 is inserted into valve 1150 when reusable part 1106 is connected to disposable part 1108. Valve driver 1113 controls the configuration of valve 1150 to control bioactive agent flow from reservoir 1138 to bolus chamber 1146, and from bolus chamber 1146 to transdermal patch 1100.

Figure 20D:
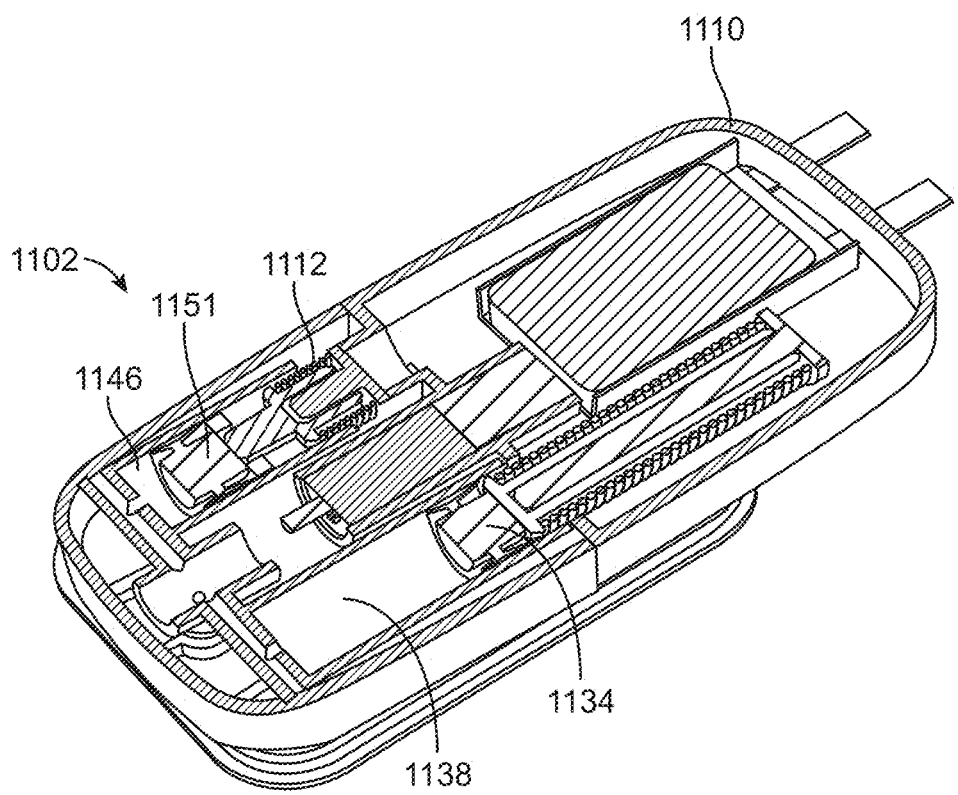

FIG. 20D shows reservoir 1138 filled with bioactive agent. Spring 1128 is compressed and provides a force to piston 1134 of reservoir 1138 to pressurize bioactive agent within the reservoir. FIG. 20D also shows a dose of bioactive agent in bolus chamber 1146. Spring 1112 is compressed against housing 1110 in reusable part and provides a force against piston 1151 to maintain pressure on the bioactive agent in the bolus chamber.

Figure 20E:
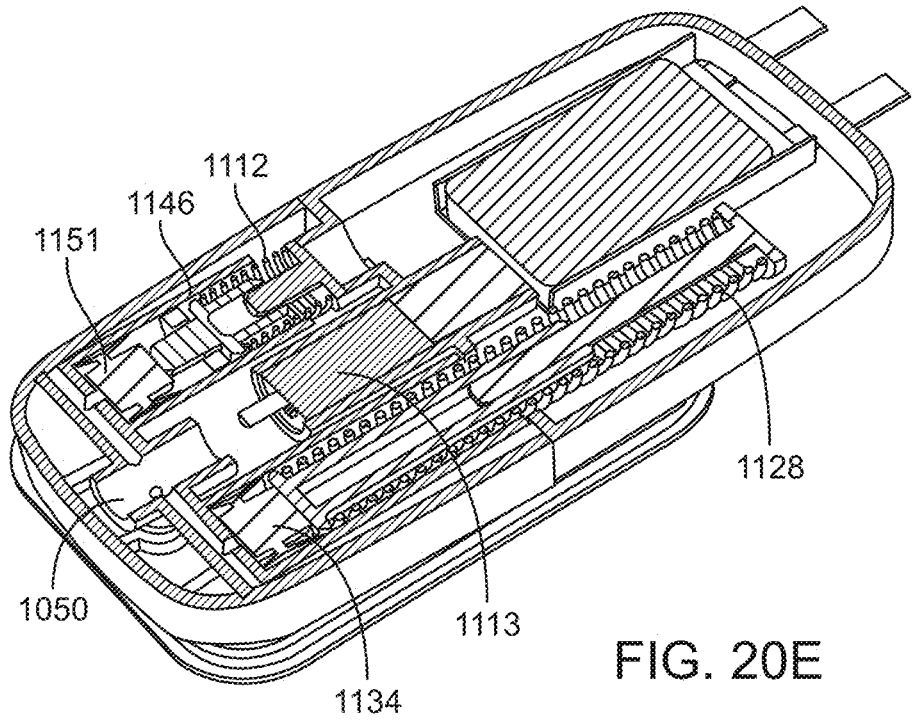

FIG. 20E shows a spent bioactive agent delivery system 1102 without bioactive agent, such as after system use by a user. Reservoir 1138 is essentially devoid of bioactive agent, and piston 1135 is at the bottom of the reservoir under the force of spring 1128. Bolus chamber 1146 is also essentially devoid of bioactive agent, and piston 1151 is at the bottom of the chamber by the force of spring 1112. (A minimal volume, such as a dead volume, of bioactive agent, may be left behind, in the reservoir and/or bolus chamber).

FIGS. 20D-20E also show valve driver 1113 powered by battery 1114 for changing the configuration of valve 1150. The components shown in FIGS. 20A-E may also or instead by used in another system, such as the system shown in FIGS. 11A-C.

Figure 21A:
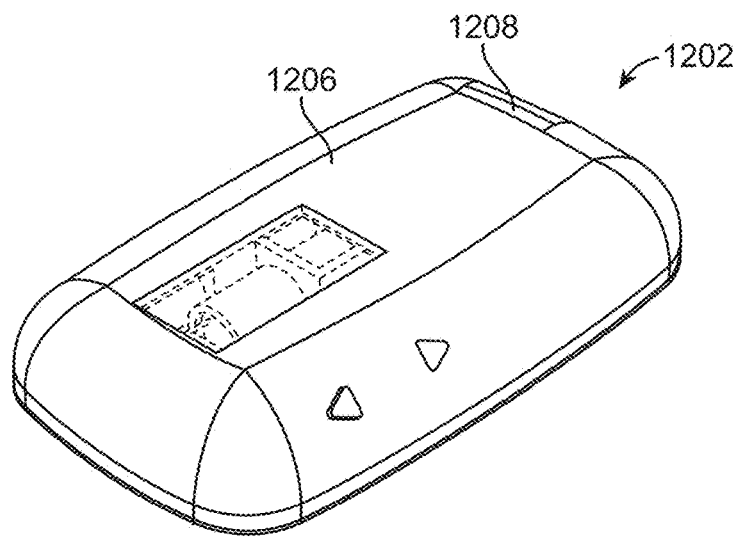
Figure 21B:
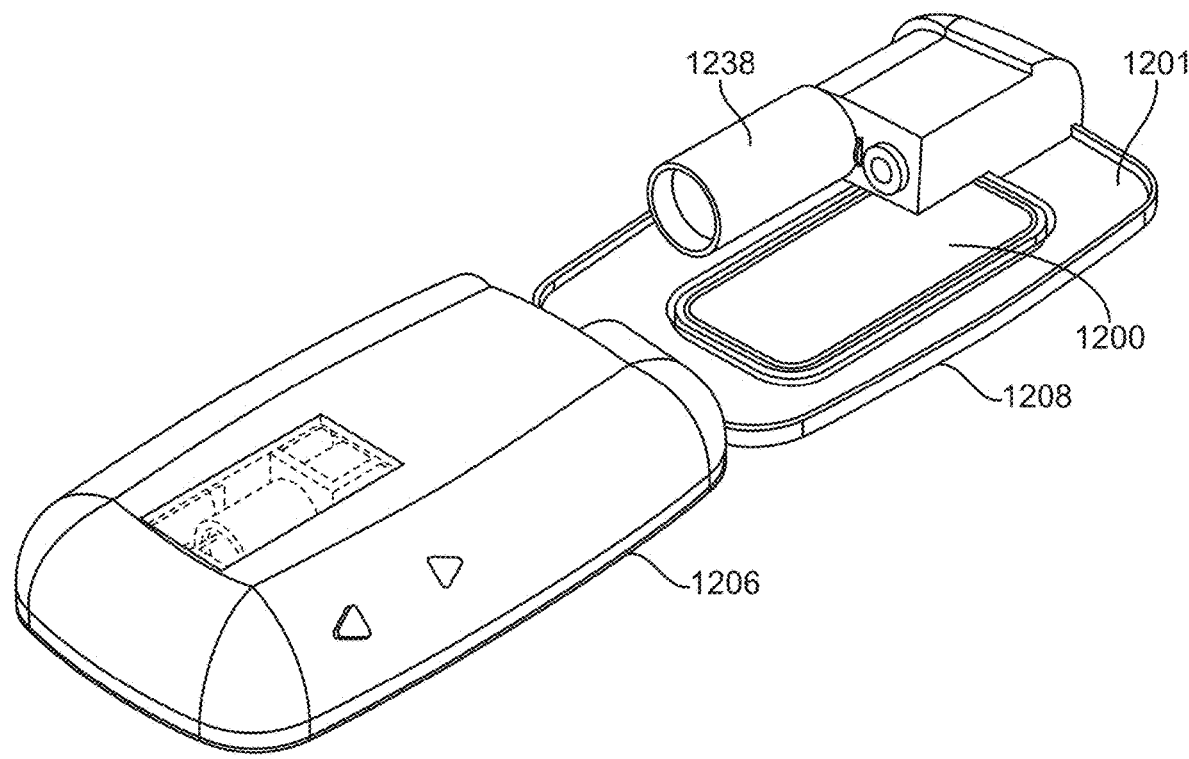

FIGS. 21A-21F show another embodiment of a two-part bioactive agent delivery system 1202, such as a wearable system, for transdermal delivery of a bioactive agent. In this embodiment, the location of the transdermal patch is offset from the center to minimize the overall system thickness of the system. FIG. 21A shows a perspective view of an assembled active agent delivery system with a reusable part 1206 and a disposable part 1208. FIG. 21B shows a perspective view of active agent delivery system separated into reusable part 1206 and a disposable part 1208 ready for assembly. Disposable part 1208 is shown partially cutaway. Transdermal patch 1208 is offset from the center to allow additional room for the reservoir and bolus chamber. FIG. 21C shows a cutaway perspective view of the system shown in FIG. 21A (system in rotated 180°). FIG. 21D shows another cutaway perspective view of the system shown in FIG. 21A in the same orientation as in FIG. 21C.

System 1202 includes reusable part 1206 and disposable part 1208 with transdermal membrane or patch (not shown) beneath patch area 1200 of base 1201. Valve 1250 and valve driver 1213 have a relatively shorter profile than do the reservoir and bolus chamber and overlie patch area 1200. Reservoir 1238 and 1246 are coaxial and have a relatively higher profile than do valve 1250 and valve driver 1213. Reservoir 1238 may be configured to hold a convenient amount of bioactive agent, such as from 500 µl to 1500 µl of bioactive agent (e.g., from 500 µl to 800 µl, 400 µl to 700 µl, etc. or any of the amounts listed elsewhere herein).

Battery 1214 may be a coin cell or other power source that requires relatively minimal space in order to maintain an overall desired system profile. A desired system profile may be a relatively low profile, for example such a system (or any system as described herein) may be configured to be between 10 mm to 30 mm in thickness (e.g., in height) such as at least 10.0 mm, 11.0 mm, 12.0 mm, 13.0 mm, 14.0 mm, 15.0 mm, 16.0 mm, or less than 20.0 mm, 19.0 mm, 18.0 mm, 17.0 mm, 16.0 mm, 15.0 mm, 14.0 mm, 13.0 mm or any values in between these values, such from 12.0 mm to 15.0 mm, 14.0 mm to 16.0 mm, 14.5 mm to 16.0 mm, etc.

For example, such a system (or any system as described herein) may be configured to be between 10 mm and 80 mm in width and/or length. For example, a system may be at 10 mm, 20 mm, 30 mm, 40 mm, 50 mm, 60 mm, 70 mm, 80 mm, 90 mm or less than 100 mm, 90 mm, 80, mm, 70 mm, 60 mm, 50 mm, 40 mm, 30 mm, 20 mm, etc. on in between any of these amounts. In some variations, a system may be configured to be a wearable system with a height between 13.0 mm and 16.0 mm, and a width between 30 mm and 50 mm (such as 34 mm×48 mm, 37 mm×37 mm, etc.).

Figure 21E:
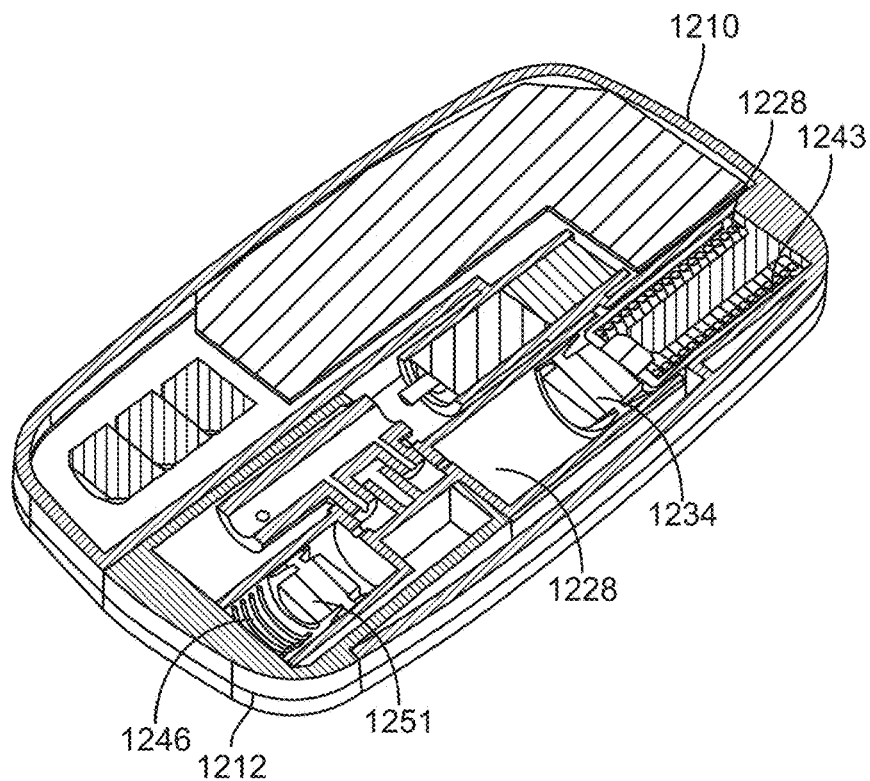
Figure 21F:
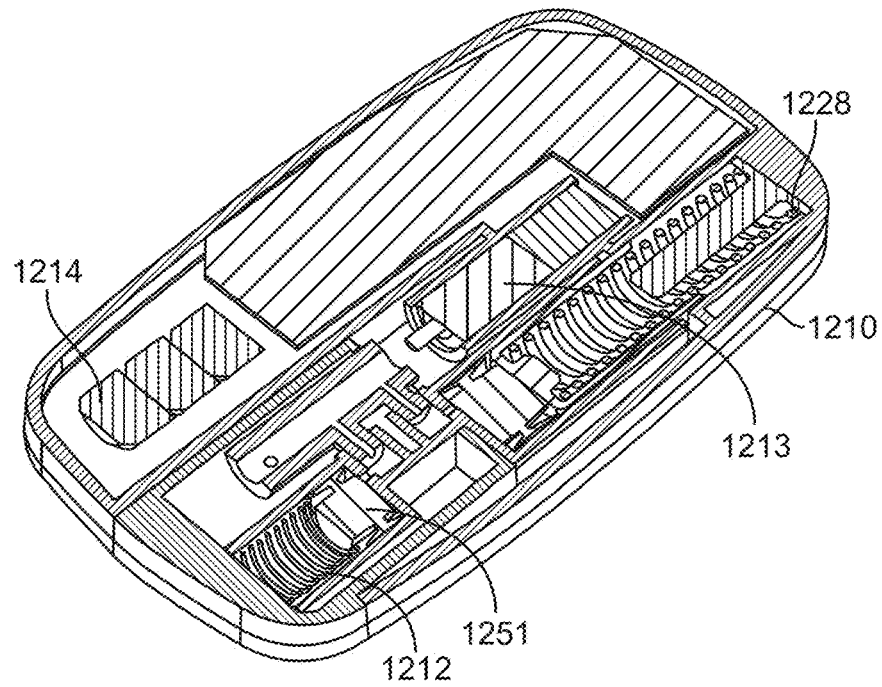

FIG. 21E shows reservoir 1238 filled with bioactive agent. Spring 1228 is compressed and provides a force against piston 1234 to pressurize reservoir 1238. FIG. 21E also shows a dose of bioactive agent in bolus chamber 1246. Spring 1212 is compressed as bolus chamber 1246 fills with pressurized bioactive agent, moving piston 1251 against the action of spring 1212. FIG. 21F shows a spent bioactive agent delivery system 1202 without bioactive agent, such as after system use by a user. Reservoir 1238 is essentially devoid of bioactive agent, and piston 1246 is at the bottom of reservoir 1238 under action of spring 1228. Bolus chamber 1246 is also essentially devoid of bioactive agent, and piston 1251 is at the bottom of bolus chamber 1246 under the action of spring 1212 (A minimal volume, such as a dead volume, of bioactive agent, may be left behind in either or both the reservoir and the bolus chamber).

FIGS. 22A-22D show embodiments of a valve and valve driver for connecting a valve driver (such as in a reusable part as described herein) with a valve core (such as in a disposable part as described herein) to rotate the valve core to control bioactive agent flow between the reservoir and bolus chamber and bolus chamber and outlet (e.g., to a transdermal patch or user). Valve driver 1313 includes shaft 1315 with a taper configured to fit with a corresponding tapered hole 1378 in valve core 1376. In some variations, a shaft may have a rib 1321 or a plurality of ribs (e.g., at least 2, at least 3, at least 4, at least 5, at least 6, etc.) that may help hold the shaft in the hole, as shown in FIG. 22D. A valve core may be made from a softer material than is the rib(s) and the rib(s) may crush when the shaft is inserted into the hole.

Figure 23:
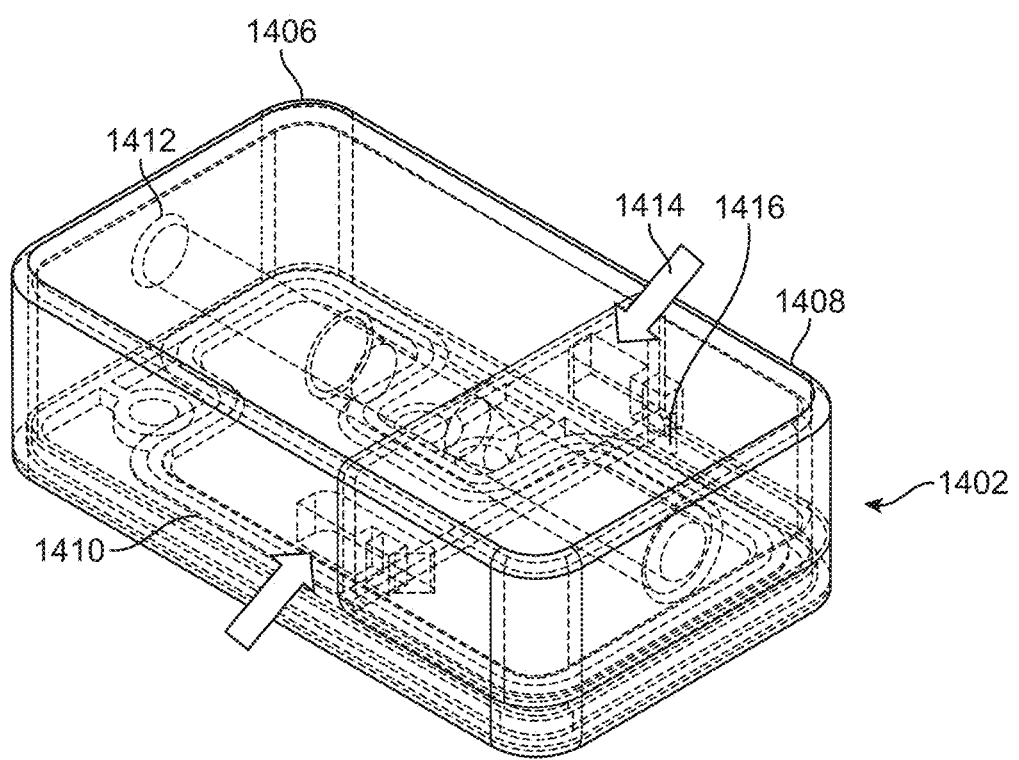
FIG. 23 shows a partially transparent perspective view of a two-part bioactive agent delivery system with a mechanism for ejecting the disposable part from the reusable part.

FIG. 23 shows another embodiment of a bioactive agent delivery system 1402. Bioactive agent delivery system 1402 includes damping mechanism 1412 configured to prevent all of the force from the spring(s) in the system from unloading (suddenly) onto the user. FIG. 23 also shows bioactive agent delivery system 1402 with housing 10 sufficiently strong to withstand force from the springs. FIG. 23 also shows clips 1416 configured to hold the reusable part and disposable part together. FIG. 23 also shows flex region 1414 configured to flex upon pressure and release clips 1416 to release disposable part 1408 from reusable part 1106. Such clips or other attachment mechanisms can be used with any of the two-part delivery system embodiments discussed herein.

Figure 24B:
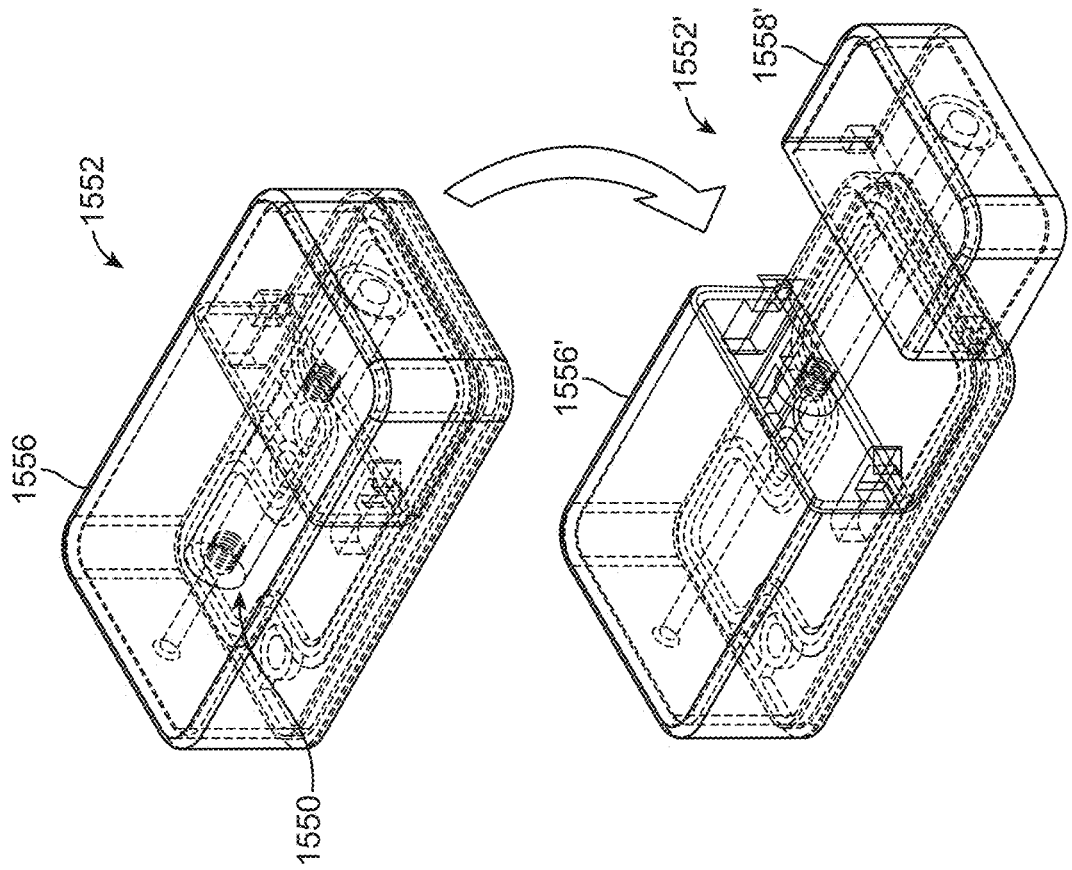
FIG. 24B shows a partially transparent perspective view of another embodiment of a bioactive agent delivery system with a reusable part and a disposable part with a second mechanism to prevent sudden release of spring force.
Figure 24A:
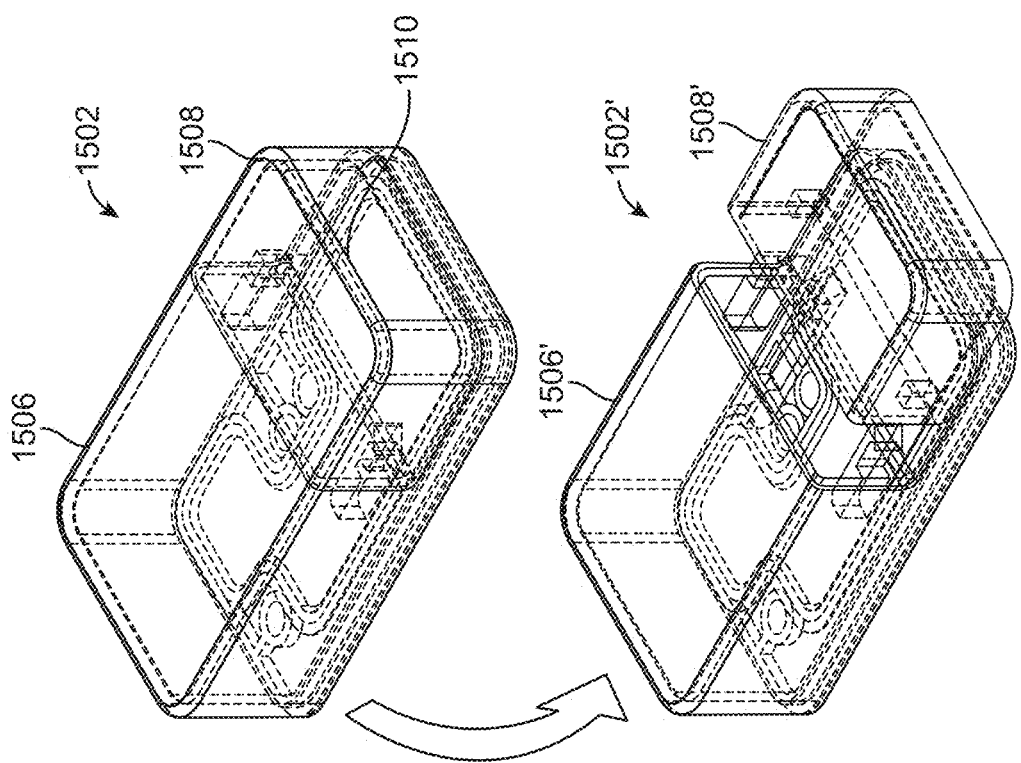
FIG. 24A shows a partially transparent perspective view of an embodiment of a bioactive agent delivery system with a reusable part and a disposable part with a second mechanism to prevent sudden release of spring force.

FIGS. 24A-24B show embodiments of a bioactive agent delivery system with mechanisms to prevent sudden release of spring force onto a user. FIG. 24A shows bioactive agent delivery system 1502 with reusable part 1506 and disposable part 1508 with mechanism 1510 for preventing the sudden release of spring force. In FIG. 24A the system is held together by clips, and a passive mechanism 1510 is present in the system (e.g., during system use). As shown by the arrow indicating a change in device state from connected to disconnected, mechanism 1510 prevents full release of disposable part 1508. A user secondary clip is released by the user to fully remove disposable part 1508 from reusable part 1506.

In FIG. 24B a system 1552 is held together by clips, and a passive mechanism 1550 is present in the system (e.g., during system use). As shown by the arrow indicating a change in device state from connected to disconnected, passive mechanism 1550 prevents full release of disposable part 1558. A twist to the system (e.g., by a user) fully removes disposable part 1558 from reusable part 1556.

Figure 25:
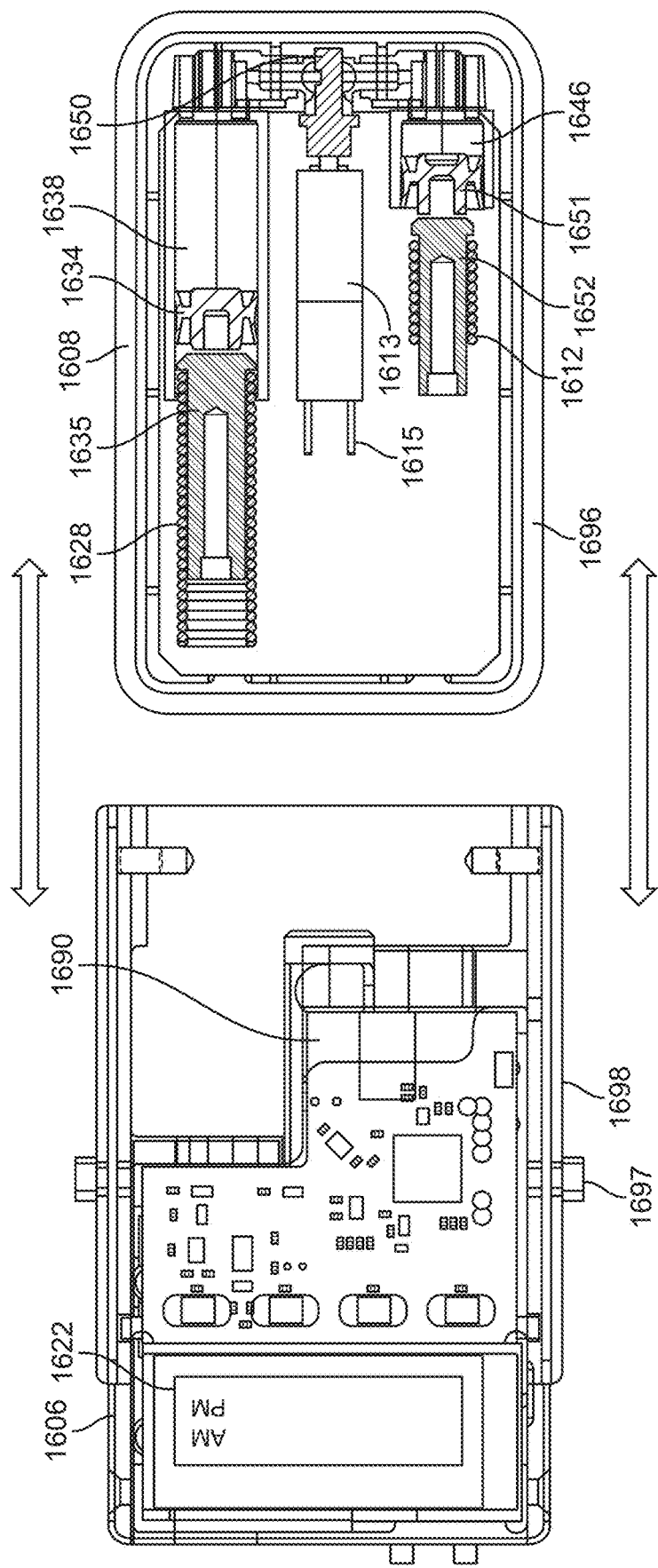
FIG. 25 is an exploded view showing yet another embodiment of a bioactive agent delivery system with a reusable part and disposable part.

FIG. 25 shows yet another embodiment of a bioactive agent delivery system with a reusable part 1606 and a disposable part 1608. As in earlier embodiments, the disposable part 1608 has a reservoir 1638 containing a bioactive agent and a bolus chamber 1646 communicable with reservoir 1638 through a valve 1650. In this embodiment, bolus chamber spring 1612 extends between a surface in the disposable part and a surface of a movable actuator 1635 to apply a force to bolus chamber piston 1651. Likewise, reservoir spring 1628 extends between a surface in the disposable part and a surface of a movable actuator 1652 to apply a force to reservoir piston 1634. The valve actuator 1613 is also disposed within disposable part 1608. When the disposable part 1608 is attached to the reusable part 1606 (by, e.g., sliding rails 1696 into corresponding grooves 1698 and tightening screws 1697), an electrical plug 1615 in the disposable part goes into a corresponding socket (not shown) in a controller and power supply 1690 in the reusable part. Valve 1650 can then be actuated by providing power to valve actuator 1613 to turn valve 1650 to allow bioactive agent to move from reservoir 1638 to bolus chamber 1646 or from bolus chamber 1646 to the patient (e.g., through a transdermal membrane) in the manner described above. Also as described above, the reusable part 1606 contains a display and other electronics 1622.

Figure 26A:
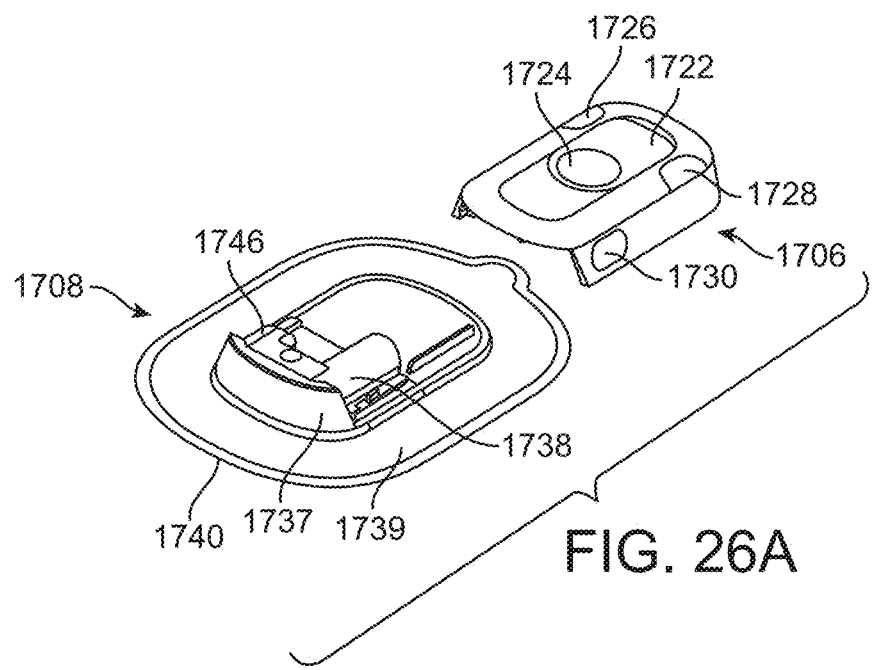
FIG. 26A is an exploded perspective view of yet another embodiment of a bioactive agent delivery system with a reusable part and a disposable part.
Figure 26B:
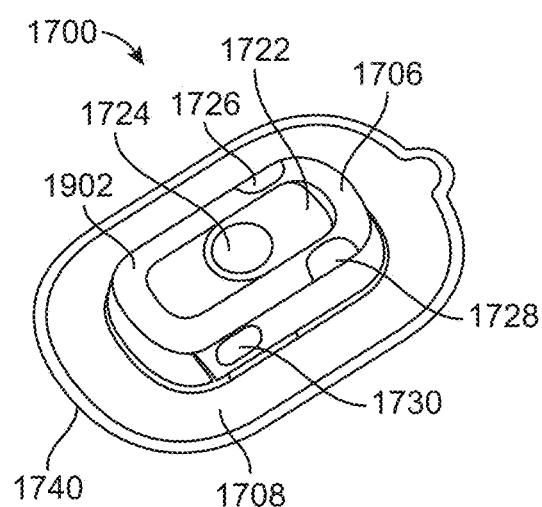
FIG. 26B is a perspective view of the system of FIG. 26A.
Figure 26C:
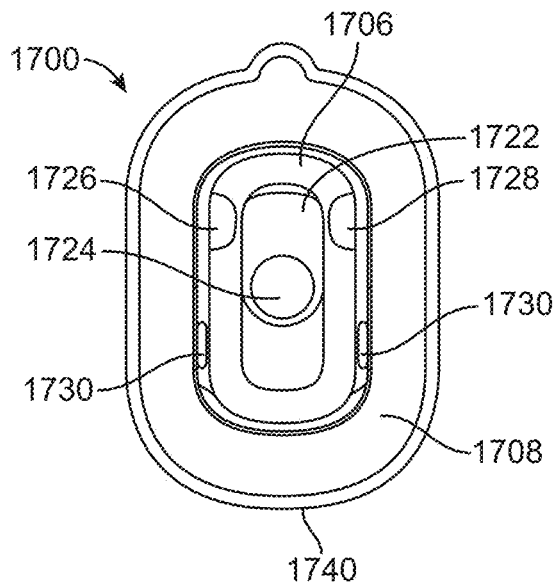
FIG. 26C is an elevational view of the system of FIG. 26A.
Figure 27A:
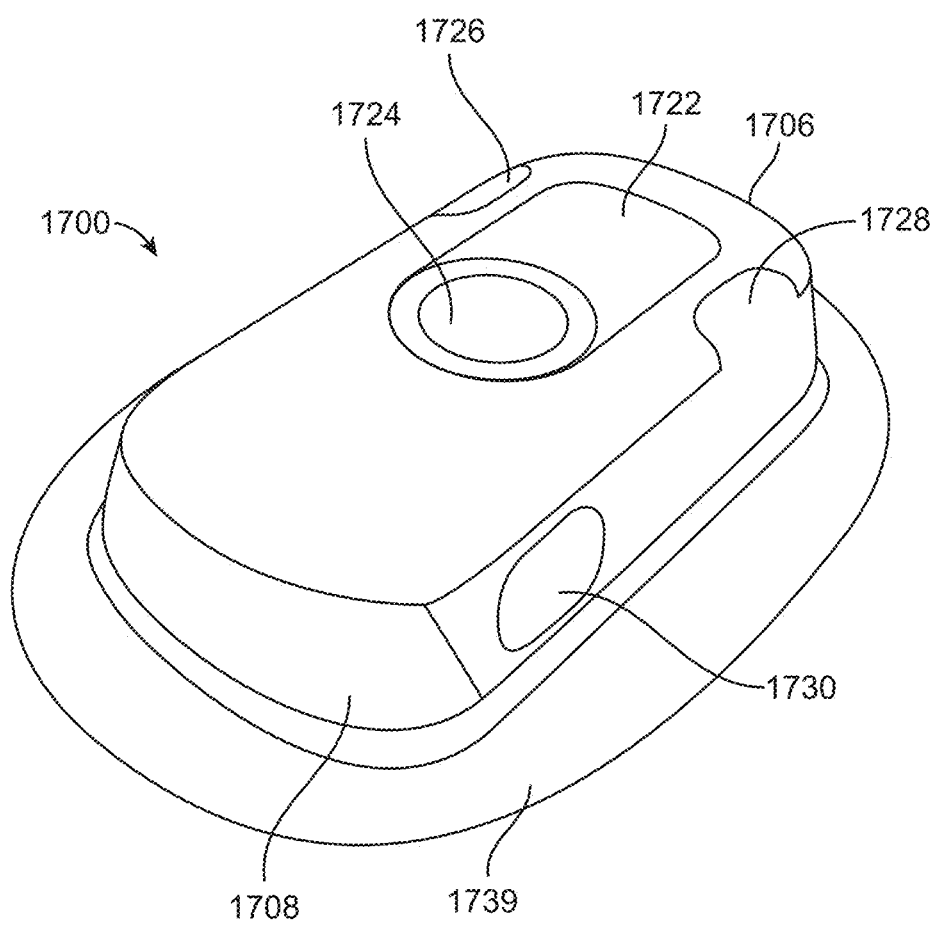
FIGS. 27A and 27B are perspective views of the system of FIG. 26A.
Figure 27B:
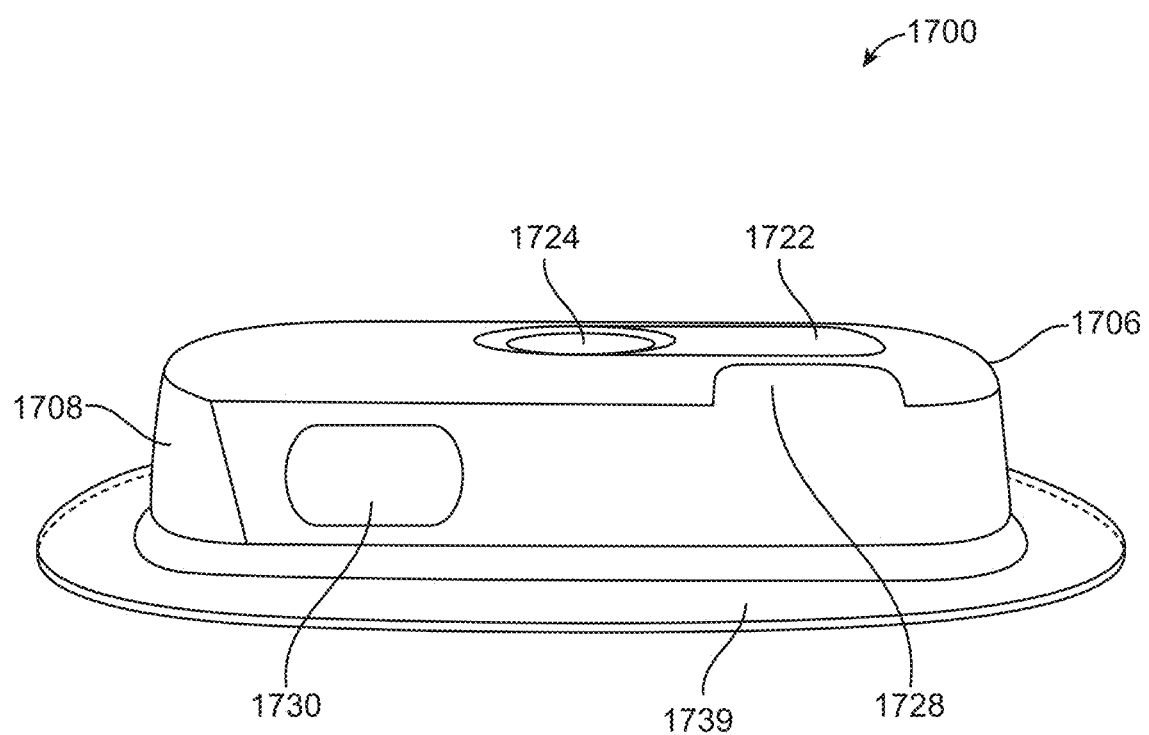
Figure 27C:
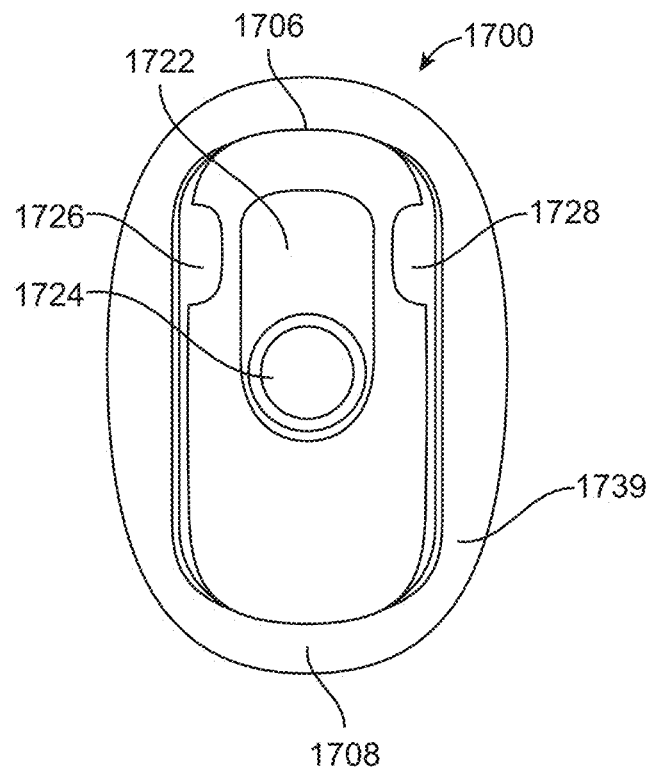
FIGS. 27C and 27D are top elevational views of the system of FIG. 26A.
Figure 27D:
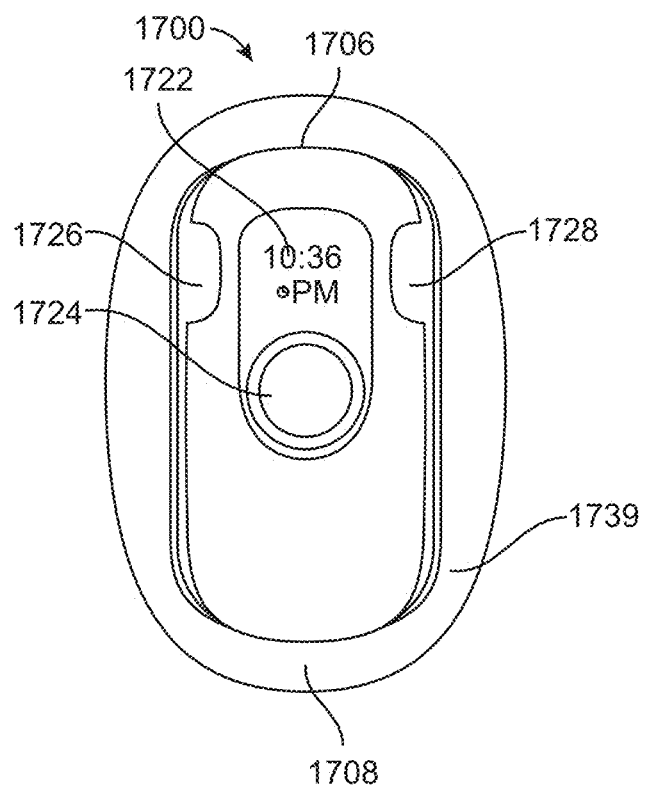

FIGS. 26-28 show yet another embodiment of a bioactive agent delivery system with a reusable part 1706 and a disposable part 1708. The reusable part 1706 snaps onto the disposable part 1708 via snap connections (not shown). Release buttons 1730 on the exterior of housing 1902 may be depressed to disconnect the reusable part 1706 from the disposable part 1708. User actuatable buttons 1724, 1726 and 1728 may be used to provide input to the device. A transparent display portion 1722 of the housing 1902 permits the device's display to be seen.

Figure 28A:
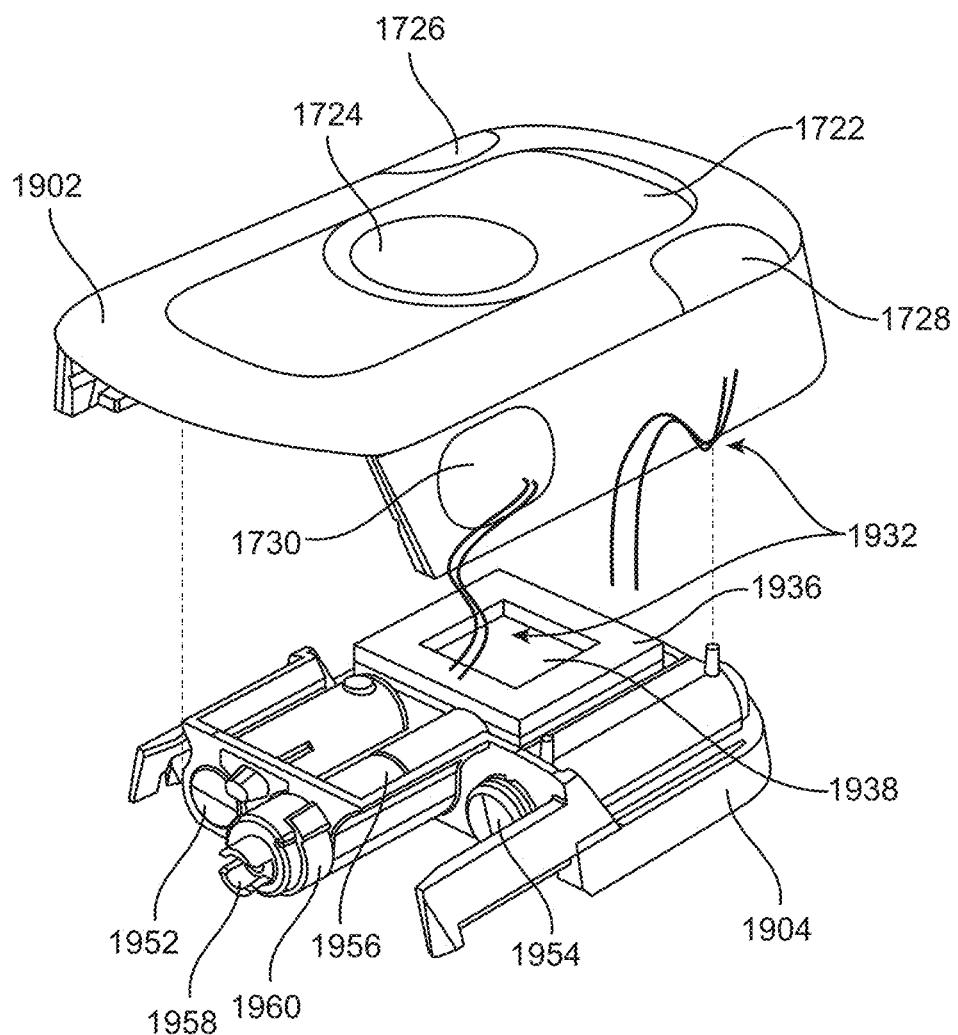
Figure 28B:
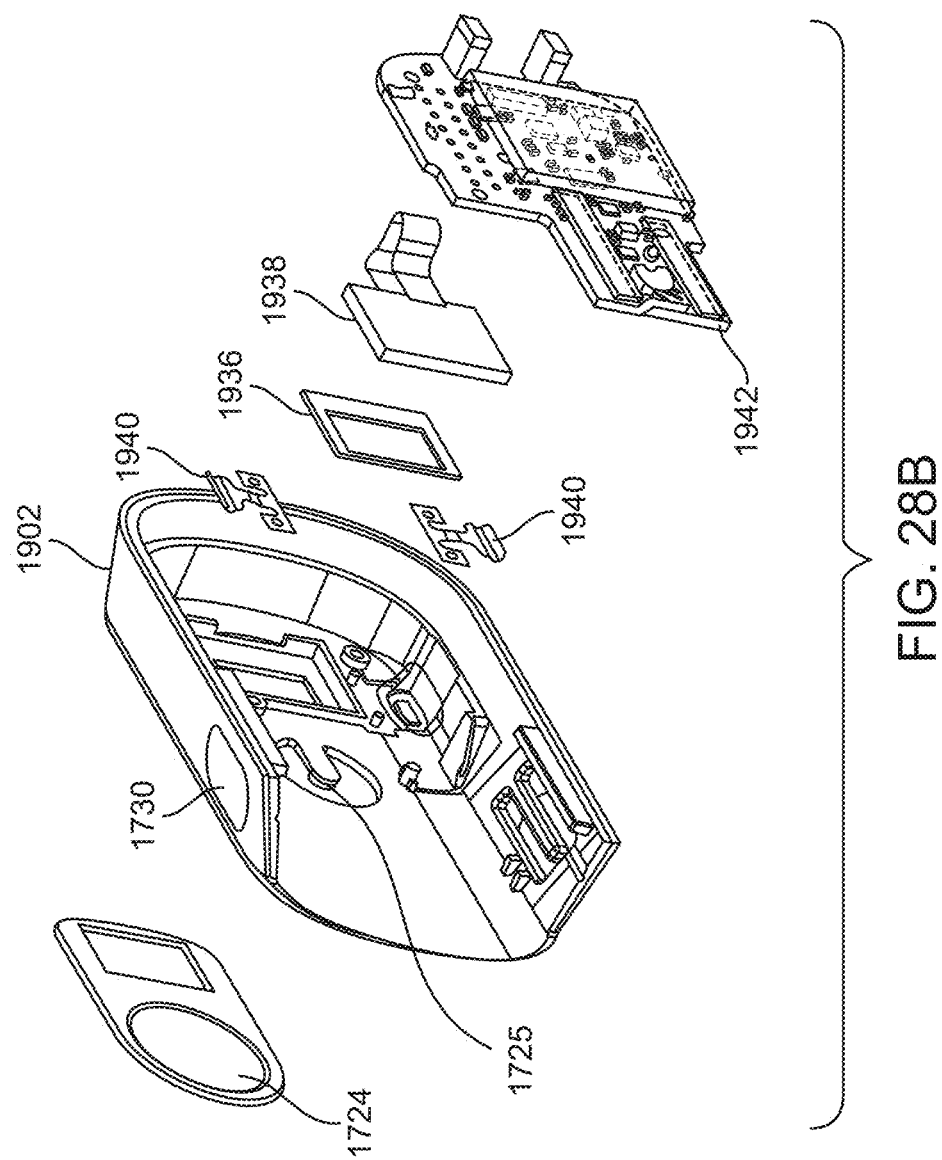

As shown in FIGS. 28A-C, the reusable part 1706 has an upper housing 1902 and a lower housing 1904. Wire pairs 1932 and bendable metal components 1940 connect buttons 1726 and 1728 to the printed circuit board 1942. Button 1724 moves the cantilever 1725 formed in housing 1902 into contact with a switch on the PCB 1942. An adhesive member 1936 attaches the display 1938 to the housing.

A battery 1950 and battery spacer 1948 rest in a lower housing 1904. The battery 1950 power a valve motor 1956. Valve motor 1956 connects to the valve in the reusable part view couplers 1958 and 1960. Springs 1952 and 1954 connect to the bolus chamber 1803 and reservoir 1801, respectively, of the disposable part 1708 (shown in FIG. 28D). A movable contact switch 1962 moves inward when the reusable part 1706 is connected to the disposable part 1708 to depress a switch on the PCB 1942 to indicate that the two components have been connected.

Figure 28D:
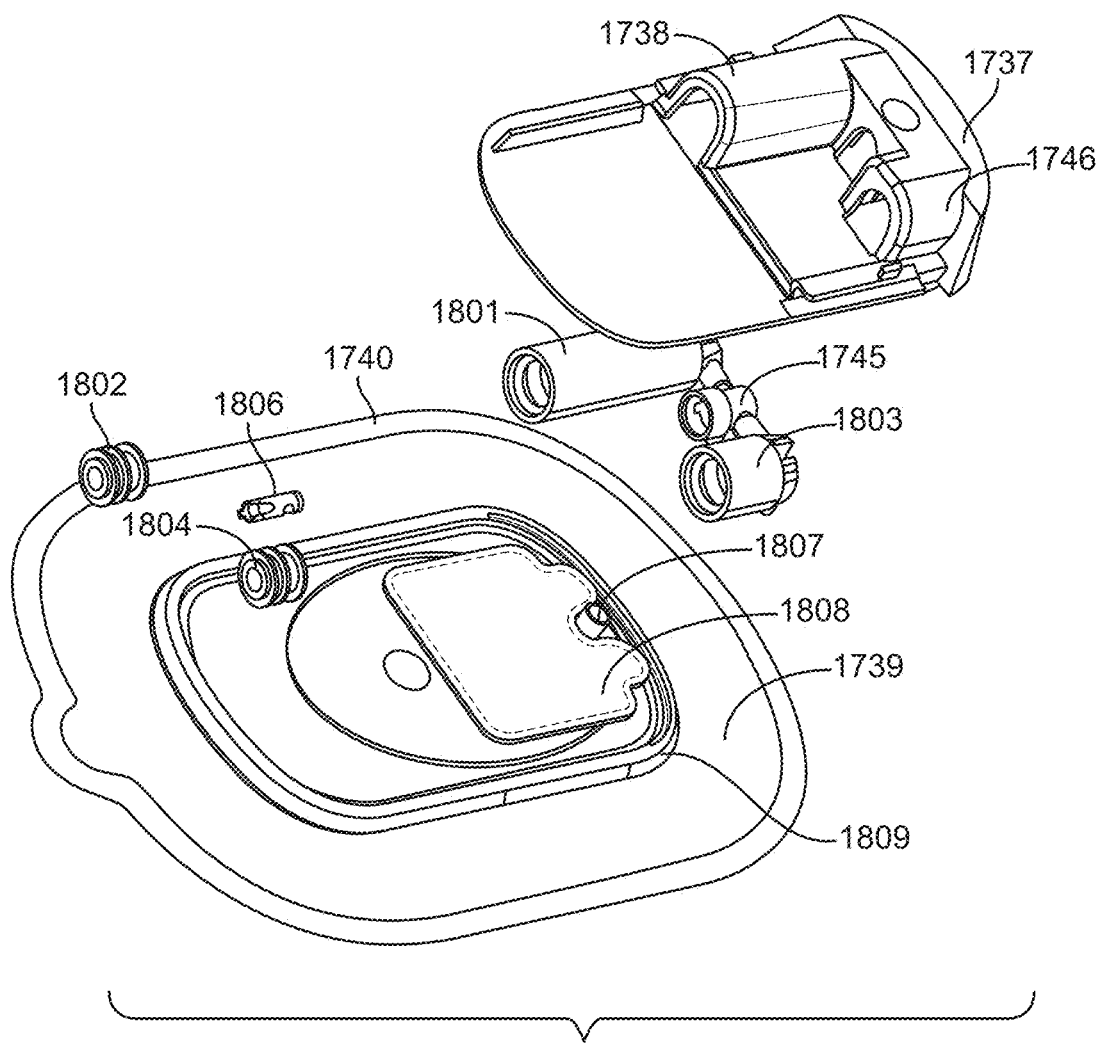
Figure 28E:
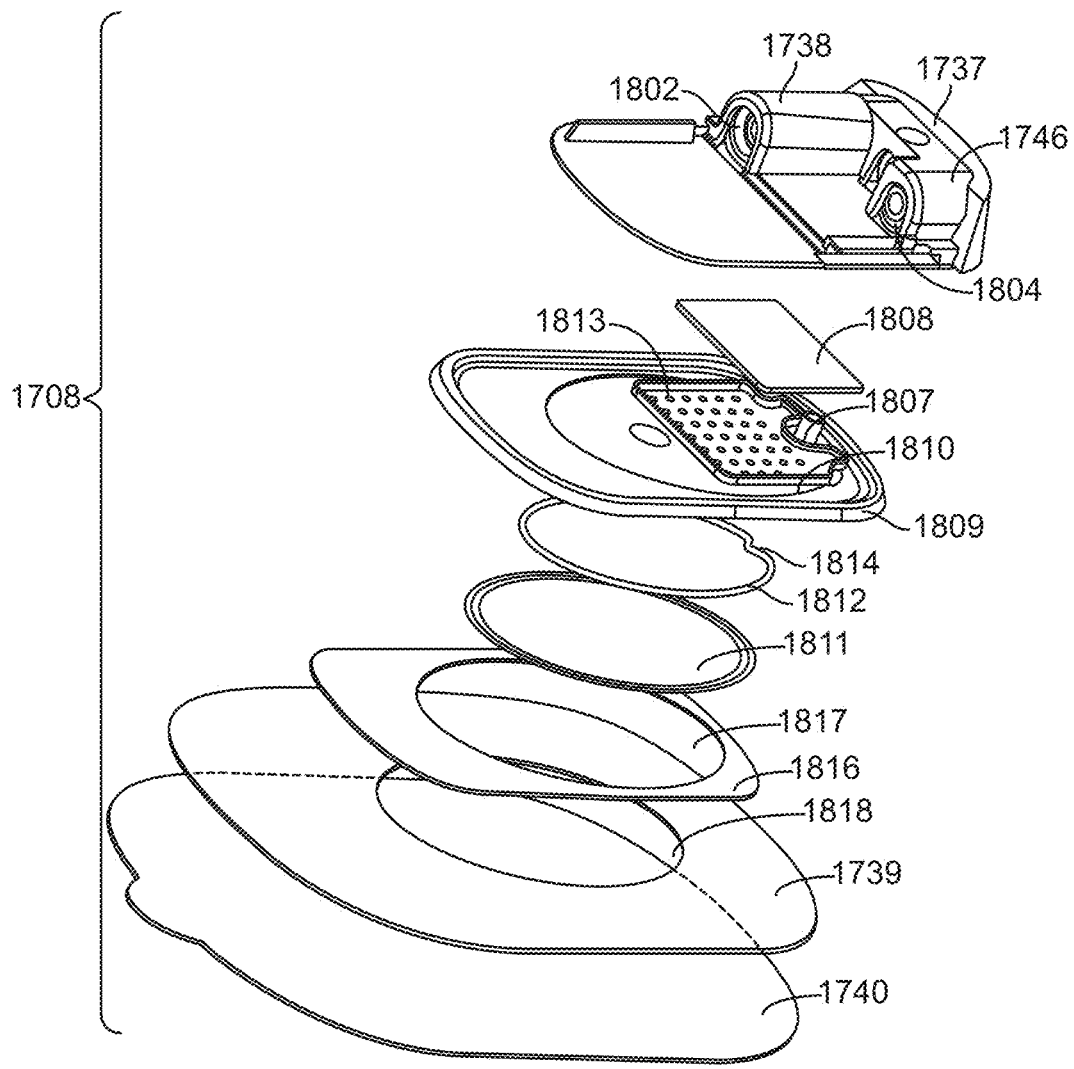
Figure 28F:
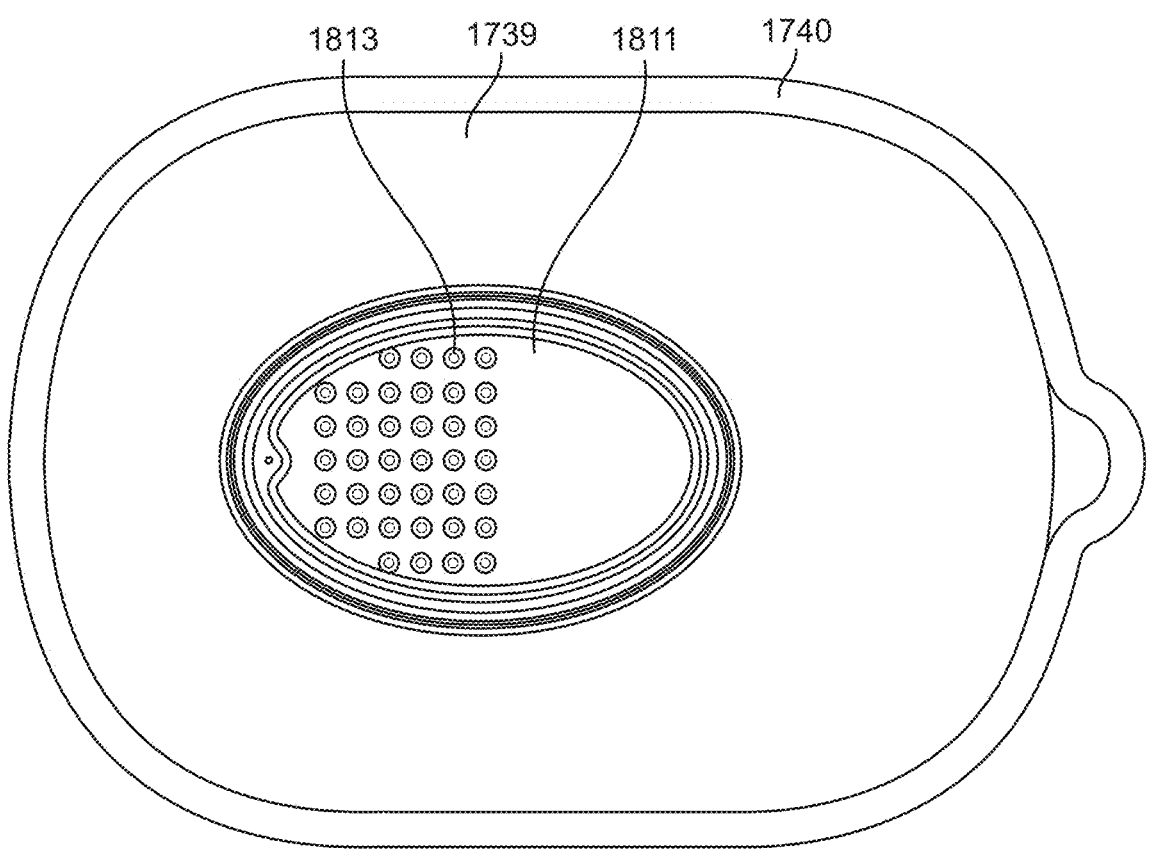

FIGS. 28D-F show aspects of the disposable part 1708. Housing 1737 has compartments 1738 and 1746 containing the reservoir 1801 and bolus chamber 1803. Pistons 1802 and 1804 are disposed in the reservoir 1801 and bolus chamber 1803, respectively, and interact with springs 1954 and 1952, respectively, when the disposable part is connected to the reusable part. Housing 1737 also contains the valve housing 1745 and valve core 1806. Valve core connects to valve motor 1956 via couplers 1958 and 1960 (FIG. 28C) when the reusable part is connected to the disposable part.

Attached below housing 1737 is a membrane chassis 1809. Absorbent material, such as absorbent paper 1808, sits in a tray 1810 disposed in the top side of chassis 1809. A plurality of openings 1813 in tray 1810 extend through chassis 1809. Beneath the chassis 1809 are a transdermal membrane 1811 (such as, e.g., a polypropylene membrane, as described below) and a gas permeable membrane 1812 having pores size to permit gaseous solvent to pass through, as described elsewhere in this disclosure. A fluid passageway 1807 extends up from chassis 1809 into valve housing 1745 when chassis 1809 is attached to the underside of housing 1737 to provide a fluid flow path from valve core 1806 through a notch 1814 in gas permeable membrane 1812 to transdermal membrane 1811. In some embodiments, the outer perimeter of transdermal membrane 1811 is heat bonded to the bottom of chassis 1809, which holds the gas permeable membrane 1812 in place as well.

A device adhesive layer 1816 with double-sided adhesive attaches the membrane chassis 1809 to a skin adhesive layer 1739 formed, e.g., from foamed tape. Openings 1817 and 1818 in the device adhesive layer 1816 and skin adhesive layer 1739, respectively, expose the underside of transdermal membrane 1811, as shown in FIG. 28F, in which the release liner 1740 is shown to be transparent in order to view the layers above it. A removable release liner 1740 covers the adhesive side of skin adhesive layer 1739 and the exposed portion of transdermal membrane 1811 until the device is ready to be adhesively attached to a user's skin to transdermally deliver nicotine or other bioactive agent to the user.

In use, when the reusable part 1706 is connected to the disposable part 1708, switch 1962 moves to indicate to the device's microcontroller that the two pieces have been connected. A microcontroller and memory on the PCB 1942 logs the time of connection. In some embodiments, the PCB includes a wireless transmitter (using, e.g., the Bluetooth communication protocol) for communicating the fact and timing of connection to a remote device, such as a smart phone running a monitoring application. This information may also be sent to a remote location for monitoring daily compliance by a user. Connecting the two components also compresses springs 1954 and 1952 against pistons 1802 and 1804, respectively, to pressurize the contents of the reservoir 1801 and bolus chamber 1803, such as a solution of bioactive agent (e.g., nicotine) and solvent (e.g., alcohol).

Release lining 1740 may then be removed to expose the skin adhesive beneath skin adhesive layer 1739 and the underside of the transdermal membrane 1811. The combined device 1706 and 1708 is then attached to an exposed portion of the user's skin. The valve motor 1956 turns the valve core 1806 under the control of the device's microprocessor to deliver the contents of bolus chamber 1803 through passageway 1807 to transdermal membrane 1811. As the bioactive agent passes through transdermal membrane 1811 to the user's skin, solvent evaporates from the bioactive agent solution, passes through gas permeable membrane 1812 and openings 1813 into the absorbent material 1808. Removing solvent vapor during delivery of bioactive agent helps the device control the delivery profile of the bioactive agent, as described, e.g., in U.S. Pat. Nos. 8,252,321; 8,440,221; and 7,780,981.

Buttons 1726 and 1728 may be used to set program timing for delivery of the bioactive agent. For example, when delivering nicotine in a nicotine replacement therapy protocol, the user may program in a wake time so that a bolus of nicotine can be delivered before the user awakes. These buttons may also be used to toggle through screens, set up Bluetooth connections with remote devices, turn the display on and off, etc.

Button 1724 can be depressed by the user to indicate a craving, such as a craving for a cigarette. The system controller logs actuation of the crave button 1724 and sends craving information via the wireless transmitter to a remote device (such as a smart phone). An application on the remote device can then coach the user through the craving experience, display historical craving data, etc. Craving information from multiple users can be aggregated at a central location (e.g., over the internet via WiFi or a cellular network) to help refine dosage and usage patterns. Support information can also be sent back to the user's smartphone application, such as a text message saying, "We received your craving indication. Concentrate on breathing deeply for 30 seconds until craving passes." More details of the psychological support that can be provided through the device may be found in US 2014/0207048.

The device can also note and log when a first bolus of nicotine or other active compound is delivered. In that way, the device can generate a notice to replace the disposable part a set time after the first bolus has been delivered. This information and other information about the operation of the device (e.g., self-test results) can be sent to a remote device (such as a smart phone) via the device's wireless transmitter.

Figure 29:
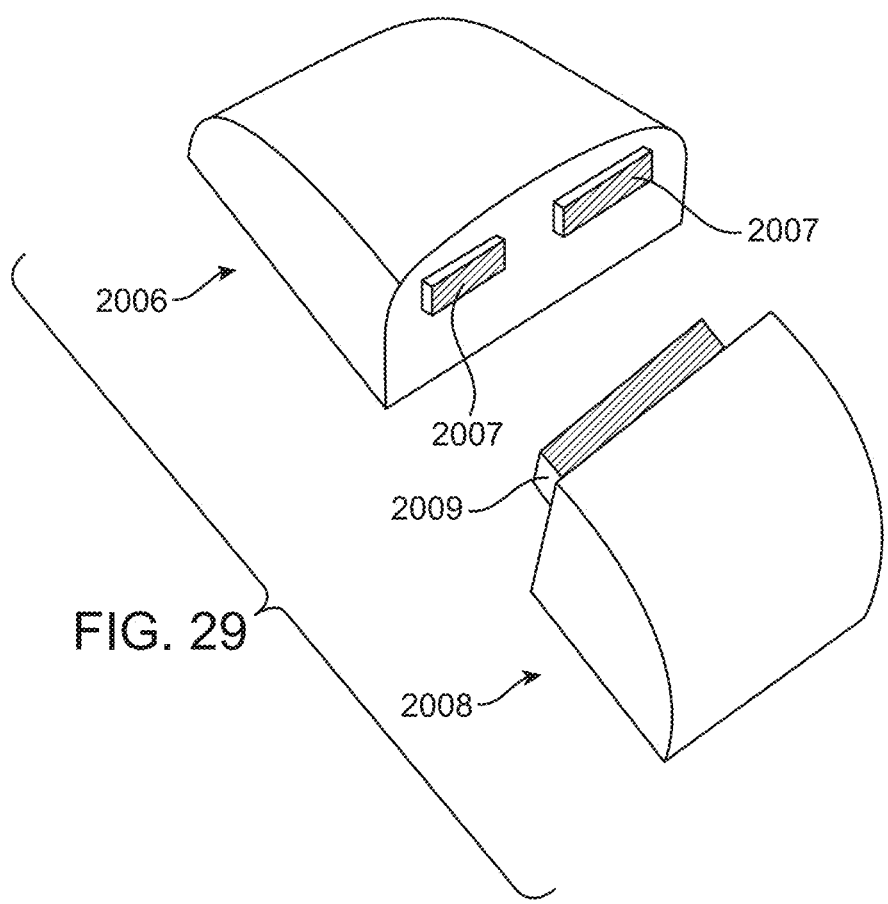
FIG. 29 is a schematic drawing illustrating a connection feature of the system of FIG. 26A.

FIG. 29 illustrates an embodiment of a transdermal delivery device including a reusable part 2006 with a control unit and a disposable part 2008. As an alternative to the switch 1962 to show a connection between the reusable part and the disposable part, this embodiment employs conductive elements on the exterior of the two housings to close a circuit, which sends a signal to the device electronics that the two components have been connected. In the illustrated embodiment, the reusable part 2006 includes a conductive elastomer 2007, and the disposable part 2008 includes a conductive elastomer 2009. The conductive elastomer 2007 and conductive elastomer 2009 complete an electrical connection when the reusable part 2006 and disposable part 2008 are engaged with each other.

A bioactive agent delivery system as described herein may be useful for delivering a bioactive agent to any part on or in a user's body. In some particular variations, a bioactive agent delivery system as described herein may deliver a bioactive agent topically or transdermally to or through a user's skin. For example a bioactive agent delivery system may be useful for delivering any type of bioactive agent to a user topically or transdermally or with another method, such as for delivering alprazolam, apomorphine, azelastine, buprenorphine, bupropion, clonidine, enalpril, estradiol, ethinyl estradiol, fentanyl, granisetron, another hormone, insulin, lidocaine, memantine, methylphenidate, methamphetamine, nitroglycerine, nicotine, norethisterone acetate (NETA), norelgestromine, oxybutynin, another pain management agent, pergolide, phenteramine, pramipexole, ramipril, ropinirole, rotifotine, scopolamine, selegiline, tecrine, testosterone, timolol, tolterodine, etc. Transdermal delivery may be especially useful for small lipids or oil-soluble substances. In some variations, a bioactive agent may penetrate (e.g., move across) skin on its own (passive diffusion). The skin provides a strong barrier against material transfer (such as bioactive agent penetration) however, and many bioactive agents penetrate the skin very poorly. In some variations, topical or transdermal transfer of a bioactive agent may be enhanced. In some examples, movement of a bioactive agent across skin may be enhanced by a chemical enhancer such as, for example, using ethosomes (phospholipid-based elastic nanovesicles containing a high ethanol content (e.g., 20-45%), liposomes, niosomes (non-ionic surfactant vesicles), a pro-drug, solid lipid nanoparticles, supersaturation (such as by decreasing or increasing bioactive agent and/or solvent pressure, temperature, volume, etc.), transferosome (e.g., an elastic or deformable vesicles). In some examples, movement of a bioactive agent across skin (or otherwise into a body) may be enhanced by a physical enhancer, such as, for example, using acoustical methods, electrophoresis, electroporation, heat assisted delivery, iontophoresis, light or another electromagnetic enhancer, magnetophoresis, microneedles, nanoporation, needle-free injection, piezoelectric droplet jet dispersion, a pump short-duration shock wave, sonophoresis, skin abrasion, another subcutaneous delivery method, thermal droplet jet dispersion, ultrasound (low-frequency ultrasound), etc. In some examples, insulin or nicotine is delivered, such as using a transdermal patch for nicotine delivery or a pump for insulin delivery. A needle or microneedle may be configured to penetrate a person's skin to any depth to deliver a bioactive agent, but in general a microneedle may be especially useful for penetrating a top layer of a person's skin sufficient to get past the skin barrier function, but not so deep as to reach nerve endings and cause pain. A needle or microneedle(s) may be solid or non-solid, and may be hollow or contain pores or holes. A patient contact portion may include a single needle or microneedle or a plurality of needles or microneedles such as 2 or more, 5 or more, 10 or more, 20 or more, 50 or more, 100 or more 500 or more or any number in between these. The needles or microneedles may be contained in an array measuring less than 5 cm×5 cm, less than 1 cm×1 cm, less than 500 mm×500 mm, less than 100 mm×100 mm. a bioactive agent may flow or move around an outside of a microneedle or may flow or move through the inside of a microneedle. A needle or microneedle may have (e.g., contain or be coated with) or not have an initial dose of a bioactive agent and a dose or subsequent dose may be supplied to the needle or microneedle by a bioactive agent delivery device as described herein. A microneedle may for example, be generally tapered and may have a bevel, sharp end, or taper at a delivery end configured for penetrating a body tissue such as an outer layer of skin. A microneedle may be less than 250 µm at its base, less than 450 µm height, have an opening less than 80 µm down to less than 10 µm or less than 1 µm. A pitch of a needle center to needle center may be less than 400 µm. A microneedle that is relatively larger in one or more of its dimensions may reduce clogging and improve fluid (bioactive agent) flow. A smaller needle may smaller than a microorganism (such as a bacterium) to prevent (or reduce the likelihood of) a microbiological infection. A microneedle may be used for any bioactive agent delivery but may be especially useful for delivering a drug, a genetic material, a peptide, a protein, a vaccine, etc. that does not readily diffuse or penetrate through an outer skin layer.

In general bioactive agent delivery as described herein includes delivery of a bolus (dose) of a bioactive agent from a delivery device to a person. Delivery from a delivery device may be pre-set (predetermined) or may be on-demand. Pre-set delivery may be pre-programmed into a delivery device or may be user-controllable. Bioactive agent delivery may be made at regular times (intervals), such as multiple times during a day or at the same time of day but on different days (periodic). Bioactive agent delivery may be pre-set but connected to a regularly occurring temporal event such as at a certain time every day, every week, on a particular day, every month, etc. Such a temporal event may happen at the same time every day or may happen at different times. For example, bioactive agent delivery may be based on (connected to) an alarm or to an event such as to an event on a calendar. Bioactive agent delivery in response to an alarm configured to wake a person from sleep may be especially useful for delivering a bioactive agent for an event that correlates with a person's daily schedule or daily biorhythms and to a person waking up. For example, heart attacks, migraine headaches, nicotine cravings, strokes and other events commonly occur in the morning. Some of these have been correlated with biological changes (endocrine or hormonal changes) in going from sleeping to being awake. Strokes have been shown to occur more frequently on Mondays than any other day of the week and also to occur more commonly in the winter. Some women experience migraine headaches that correlate with their menstrual cycle, which are referred to as "menstrual migraines" and are thought to be related to the normal (predictable) drop in the levels of estrogen during the woman's monthly menstrual cycle. In a particular example, a bioactive agent may be a nicotine cessation substance and a delivery device may be configured to deliver the substance before an alarm wakes the person from sleep (or to deliver the bioactive agent before the time the person generally awakens). An alarm may be set at the same time(s) on two or more days (such as consecutive, weekly, monthly, etc.) or may be set at different times.

A delivery profile or delivery device may be configured to deliver a relatively constant amount of a bioactive agent to an individual or to deliver varying amounts. In some variations, a delivery profile may be configured to provide a relatively constant level of bioactive agent in the bloodstream. For example, delivery may be pulsatile or over intervals and may be controlled by a rate of the transdermal patch diffusion. In other variations, a bioactive agent delivery profile may be configured to provide varying levels of bioactive agent in the blood stream. For example, nicotine cravings come and go based on various factors, such as the time of day, food intake, the person's activities, and so on. Cravings are often greater in the morning or after dinner. Nicotine cravings are generally not a problem while the person is sleeping; however they may be a problem as soon as the person wakes up. Thus, a user may benefit from having a smoking cessation agent delivered when it is needed (e.g., shortly before or shortly after waking up) to minimize or prevent an expected craving and not having it delivered at other times (e.g., in the middle of the night). For example, pain can be severe during the night, and thus providing bioactive agent to manage pain during the night may be helpful. A bioactive agent delivery system as described herein may provide such an agent when it is needed (e.g., at night as well as during the day). Providing a bioactive agent only when it is needed may reduce drug metabolic load in the liver for processing the bioactive agent, may prevent tolerance to a bioactive agent from building up, and so on. Bioactive agent delivery may also or instead be continuous such as at a continuous but relatively low level. For example, a transdermal delivery apparatus or other delivery apparatus may be configured to transfer bioactive agent to a user over a period of time (e.g., an hour, two hours, four hours, etc.).

As indicated elsewhere, a reusable part of an active agent delivery system is generally configured to work with a plurality of disposable parts and a single reusable part can be used by a user with a plurality of disposable parts (e.g., first, second, third, etc.) over time to deliver multiple doses of a bioactive agent to the user at different times or different days over weeks or months of time. Such disposable parts may be substantially the same as each other or may be different from each other. For example, two or more disposable parts for use with a single reusable part may have the same configuration as each other or may have different configurations as long as they can work with the reusable part. Two or more disposable parts configured to work with a (the same) reusable part may contain the same active agent or different active agents (or may contain the same active agent but at different concentrations). Additionally, a single disposable part may be configured to work with a plurality of differently configured reusable parts. For example, different reusable parts may have different power sources (batteries, etc.), different user interfaces, different configurations, etc. but may still be configured to work with the (same) disposable part.

Any of the components described herein can also or instead be used with other components in addition to or instead of the components shown in order to delivery bioactive agent to a user. For example, any of the transdermal patches described herein can be used with another disposable part or a different bioactive agent delivery system, etc. In some variations, a transdermal delivery apparatus could be separate from a disposable part. In some examples, a transdermal delivery apparatus could be used with an entirely different bioactive agent delivery system. In some variations, a bioactive agent delivery system as described herein may not be readily separable into two or more pieces. Rather, it may be configured as a single apparatus and not have a separate (or readily separable) reusable part and disposable part. In some variations, a component(s) as described herein as being part of a reusable part (or part a disposable part) may instead be in the disposable part (or a reusable part). For example, a power source (e.g., battery) may be in a disposable part rather than in a reusable part. This may be helpful, for example, for supplying a fresh power source (battery) with a disposable part when a new (replacement) disposable part is placed on a reusable part. In some variations, an active agent delivery system may have a plurality of disposable or a plurality of reusable parts that work together but the parts may be configured to be separately placed on a reusable part. For example, a power source (e.g., battery) or other component may be separately removable and replaceable with a fresh power source (e.g., battery) and both a disposable part and a power source may be separately replaceable (e.g., as two separate disposable parts) on a reusable part.

In some variations, a disposable part may be configured to be recharged. For examples, a disposable part may be refillable with an additional quantity of bioactive agent and may be reusable. A disposable part may be refilled with an additional quantity of bioactive agent while in place on a reusable part or may be removed from a reusable part, refilled with an additional quantity of bioactive agent, and placed back into the reusable part (e.g., replaced). Refilling a disposable part may be useful, for example, for keeping a wearable active agent system relatively small by minimizing the amount of active agent in the system at any one time. The systems, devices and methods as described herein may be used for or configured to be used for delivering a bioactive agent to any user, such as a person, an animal, a domesticated animal, a wild animal, a cat, a cow, a dog, a horse, a swine, etc.

In some embodiments the solvent solution includes water, alcohol, and a drug or bioactive agent. In some embodiments the alcohol can be one or more of isopropanol, ethanol, and methanol. The solvent solution can also include one or more of a: surfactant, excipient, or other component intended to enhance permeation or decrease skin sensitivity or skin reaction.

The solvent solution can have a ratio of water to alcohol of about 40:60 to about 60:40. The solvent solution can have a ratio of water to alcohol of about 45:55 to about 55:45. The solvent solution can have a ratio of water to alcohol of about 46:54 to about 54:46. The solvent solution can have a ratio of water to alcohol of about 47:53 to about 53:47. The solvent solution can have a ratio of water to alcohol of about 48:52 to about 52:48. The solvent solution can have a ratio of water to alcohol of about 49:51 to about 51:49.

A variety of different drugs or bioactive agents can be used with the systems described herein. In some embodiments the bioactive agent includes nicotine. For example, nicotine can be present in the solvent solution from about 0.5% to about 20% by volume. In some embodiments nicotine can be present in the solvent solution from about 0.5% to about 10% by volume. In some embodiments nicotine can be present in the solvent solution from about 0.5% to about 5% by volume. In some embodiments nicotine can be present in the solvent solution from about 0.5% to about 3% by volume.

Other examples of bioactive agents include: Acamprosate, Acetaminophen, Acetaminophen+Oxycodone, Alevicyn SG, Alfentanil, Allopurinol, Almotriptan, Alprazolam, Alprazolam XR, Amitriptylinem, Amoxapine, Apomorphine, Aripiprazole, Armodafinil, Asenapine maleate, Atomoxetine, Azelastine HCL, Baclofen, Benzbromarone, Benzydamine, Brexpiprazole, Budesonide, Bupivacaine, Buprenorphine, Buprenorphine+Nalaxone, Bupropion, Bupropion Hydrobromide, Bupropion Hydrochloride, Bupropion SR, Bupropion XR, Buspirone, Cabergoline, Capsaicin, Carbamazepine CR, Carbamazepine XR, Carbidopa+Levodopa Er, Carisprodol, Celecoxib, Citalopram, Clobazam, Clonazepam, Clonidine Patch, Clonidine SR, Clopidogrel, Colchicine, Cyclobenzaprine ER, Cyclobenzaprine PO, Dalteparin sodium, Desvenlafaxine, Desvenlafaxine ER, Dexamfetamine, Dexmethylphenidate Hcl, Dexmethylphenidate Hcl LA, Diazepam, Diclofenacm, Diclofenac Gel, Diclofenac IR, Diclofenac IV, Diclofenac Potassium IR, Diclofenac Potassium XR, Diclofenac Transdermal, Disulfiram, Divalproex Sodium, Dolasetron Mesilate, Doxepin, Dronabinol, Droxidopa, Duloxetine, Eletriptan, Entacapone, Escitalopram oxalate, Eslicarbazepine Acetate, Esomeprazole/naproxen, Estradiol, Estrogen, Eszopiclone, Ethosuximide, Etodolac, Ezogabine, Febuxostat, Felbamate, Fenbufen, Fentanyl Citrate, Fentanyl Oral, Fentanyl Patch, Fentanyl SL, Flunisolide, Fluorouracil, Fluoxetine, Fluticasone propionate, Fluvoxamine Cr, Formoterol, Fosphenytoin, Frovatriptan, Gabapentin, Gabapentin ER, Granisetron ER, Guanfacine, Hydrocodone Bitartrate CR, Hydrocodone+Acetaminophen, hydrocortisone, Hydromorphone Hcl, Hydroxyzine, Hypericum Extract, Ibuprofen, Indometacin, Ketorolac, Lacosamide, Lamotrigine, Lamotrigine CDT, Lamotrigine ODT, Lamotrigine XR, Levetiracetam, Levetiracetam IR, Levetiracetam XR, Levomilnacipran, Levosalbutamol, Lidocaine Patch, Lidocaine/Tetracaine, Lisdexamfetamine, Lithium Carbonate, Lorazepam, Lorcaserin, Hydrochloride, Losartan, Loxapine, Meclizine, Meloxicam, Metaxalone, Methylphenidate, Methylphenidate Hydrochloride, Methylphenidate LA, Methylphenidate MR, Methylphenidate Patch, Milnacipran, Mirtazapine, Modafinil, Morphine, Morphine CR, Morphine ER, Nabilone, Nadolol, Naltrexone, Naproxen, Naratriptan, Nedocromil, Nefazodone, Nitroglycerin, Nitroglycerin Ointment, Olanzapine, Olanzapine IM, Olanzapine LA, Ondansetron, Ondansetron ODFS, Ondansetron ODT, Orlistat, Oxaprozin, Oxcarbazepine, Oxcarbazepine ER, Oxybutynin, Oxybutynin Gel, Oxycodone, Oxycodone+Acetaminophen, Oxycodone Hydrochloride, Oxycodone IR, Oxymorphone, Oxymorphone ER, Palonosetro, Pamidronate, Paroxetine, Paroxetine Mesylate, Perampanel, Phentermine+Topiramate, Phentermine Hydrochloride, Phentolamine Mesylate, Pramipexole, Pramipexole-Er, Prasugrel, Prazepam, Prednisone, Pregabalin, Promethazine, Propofol, Quetiapine, Quetiapine Fumarate, Quetiapine Fumarate XR, Ramelteon, Rasagiline Mesylate, Remifentanil, Risperidone, Rivastigmine Tartrate, Rizatriptan, Ropinirole, Ropinirole XL, Ropivacaine, Rotigotine, Rufinamide, Salbutamol, Scopolamine, Selegiline, Selegiline ODT, Selegiline Transdermal, Sertraline, Sodium Oxybate, Strontium, Sufentanil-Ent, Sumatriptan Autoinjector, Sumatriptan Needle-free, Sumatriptan Succinate, Suvorexant, Tapentadol, Tapentadol ER, Tasimelteon, Temazepam, Testosterone, Tetracaine+Lidocaine, Theophylline, Tiagabine, Tiotropium, Tirofiban HcL, Tolcapone, Topiramate, Topiramate XR, Tramadol, Tramadol+Acetaminophen, Tramadol ER, Trazodone Cr, Triazolam, Trimipramine Maleate, Valproate Semisodium ER, Valproate Sodium, Venlafaxine, Venlafaxine ER, Vigabatrin, Vilazodone, Vortioxetine, Zaleplon, Zileuton, Ziprasidone, Zolmitriptan Oral, Zolmitriptan ZMT, Zolpidem, Zolpidem Spray, Zolpidem Tartrate CR, Zolpidem Tartrate Low dose SL, Zolpidem Tartrate SL, norethisterone acetate (NETA), enapril, ethinyl estradiol, insulin, memantine, methamphetamine, norelgestromine, pergolide, Ramipril, tecrine, timolol, tolterodine and Zonisamide.

The pore size and porosity of the vapor permeable membrane and the transdermal membrane can be tailored to achieve a desired flow of drug through membrane and the desired solvent flow rate. The transdermal membranes for use with the embodiments described above can be made from a material that is compatible with contact with the skin. In some embodiments the membrane that contacts the skin can comprise polypropylene. In some embodiments the membrane that contacts the skin can comprise polytetrafluoroethylene (PTFE). In some embodiments the membrane that contacts the skin can comprise ethylene vinyl acetate (EVA). In some embodiments the membrane that contacts the skin can comprise polyester and/or fluoropolymer coated polyester films. In some embodiments the membrane that contacts the skin can comprise an ethylene-vinyl acetate copolymer membrane. In some embodiments the membrane that contacts the skin can comprise an ethylene vinyl acetate copolymer (EVAC). In some embodiments the membrane that contacts the skin can comprise a polyethylene (PE) membrane. In some embodiments the membrane that contacts the skin can comprise a vinyl chloride copolymer or terpolymer. In some embodiments the membrane that contacts the skin can comprise any type of polymeric film. In some embodiments the membrane that contacts the skin can comprise a polyethersulfone (PES) compound. In some embodiments the membrane that contacts the skin can comprise a polyolefin. In some embodiments the membrane that contacts the skin can comprise a silicone matrix with a rate-controlling membrane.

In some embodiments the pore size of the transdermal membrane is selected to achieve a desired permeation rate of the bioactive agent. In some embodiments the average pore diameter of the transdermal membrane is about 0.02 µm to about 0.10 µm. In some embodiments the average pore diameter of the transdermal membrane is about 0.02 µm to about 0.085 µm. In some embodiments the average pore diameter of the transdermal membrane is about 0.02 µm to about 0.070 µm. In some embodiments the average pore diameter of the transdermal membrane is about 0.02 µm to about 0.060 µm. In some embodiments the average pore diameter of the transdermal membrane is about 0.02 µm to about 0.050 µm. In some embodiments the average pore diameter of the transdermal membrane is about 0.03 µm to about 0.050 µm. In some embodiments the average pore diameter of the transdermal membrane is about 0.04 µm to about 0.050 µm.

The porosity of the transdermal membrane can be expressed as a percentage of open surface area for the plurality of pores to the surface area of the membrane configured to contact the skin. In some embodiments the porosity of the transdermal membrane is about 25% to about 75%. In some embodiments the porosity of the transdermal membrane is about 30% to about 70%. In some embodiments the porosity of the transdermal membrane is about 30% to about 65%. In some embodiments the porosity of the transdermal membrane is about 30% to about 60%. In some embodiments the porosity of the transdermal membrane is about 35% to about 60%. In some embodiments the porosity of the transdermal membrane is about 35% to about 65%. In some embodiments the porosity of the transdermal membrane is about 35% to about 55%. In some embodiments the porosity of the transdermal membrane is about 35% to about 50%. In some embodiments the porosity of the transdermal membrane is about 40% to about 50%. In some embodiments the porosity of the transdermal membrane is about 40% to about 45%. In some embodiments the porosity of the transdermal membrane is about 40% to about 42%.

In some embodiments the transdermal membrane can be treated to change the wettability or other properties of the membrane. For example, the transdermal membrane can be surfactant treated, plasma treated, or other treatments to change wettability and other properties of the transdermal membrane.

The geometry of the plurality of pores of the transdermal membrane can vary. In some embodiments the plurality of pores can have a circular cross-section. In some embodiments the plurality of pores of the membrane have a non-circular cross section. In some cases the plurality of pores of the membrane can include longitudinal slits having a longitudinal cross section. A plurality of different pore shapes and sizes can also be used in some cases.

The transdermal membrane can have a surface area selected to deliver the desired amount of drug or bioactive agent to the skin of the wearer. In some embodiments the transdermal membrane has a surface area that is less than about 15 cm². In some embodiments the membrane has a surface area that is less than about 10 cm². In some embodiments the membrane has a surface area that is from about 15 cm² to about 30 cm².

Specific examples of membrane materials that can be used in the drug delivery systems disclosed herein include a variety of different Celgard® products.

In some embodiments the transdermal membrane is Celgard® 2325. Celgard® 2325 has an average pore size of 0.028 µm and a porosity of 39%.

In some embodiments the transdermal membrane is Celgard® 2340. Celgard® 2340 has an average pore size of 0.035 µm and a porosity of 45%.

In some embodiments the transdermal membrane is Celgard® 2400. Celgard® 2400 has an average pore size of 0.043 µm and a porosity of 41%.

In some embodiments the transdermal membrane is Celgard® 2500. Celgard® 2500 has an average pore size of 0.064 µm and a porosity of 55%.

In some embodiments the transdermal membrane is Celgard® 2325. Celgard® 2325 has an average pore size of 0.028 µm and a porosity of 39%.

In some embodiments the transdermal membrane is Celgard® 3400. Celgard® 3400 has an average pore size of 0.043 µm and a porosity of 41%. Celgard® 3400 is surfactant coated to improve wettability of the membrane.

In some embodiments the transdermal membrane is Celgard® 3401. Celgard® 3401 has an average pore size of 0.043 µm and a porosity of 41%. Celgard® 3401 is surfactant coated to improve wettability of the membrane.

In some embodiments the transdermal membrane is Celgard® 3500. Celgard® 3500 has an average pore size of 0.064 µm and a porosity of 55%. Celgard® 3500 is surfactant coated to improve wettability of the membrane.

In some embodiments the transdermal membrane is Celgard® 3501. Celgard® 3501 has an average pore size of 0.064 µm and a porosity of 55%. Celgard® 3501 is surfactant coated to improve wettability of the membrane.

In some embodiments the transdermal membrane is Celgard® 4550. Celgard® 4550 has an average pore size of 0.035 µm and a porosity of 45%. Celgard® 4550 includes a trilayer construction of polypropylene/polyethylene/polypropylene.

In some embodiments the transdermal membrane is Celgard® 4560. Celgard® 4560 has an average pore size of 0.064 µm and a porosity of 55%.

In some embodiments the transdermal membrane is Celgard® 5550. Celgard® 5550 has an average pore size of 0.064 µm and a porosity of 55%.

The vapor permeable membrane can be made of a material with a porosity and pore size selected to minimize or substantially block the flow of liquid phase solvent and liquid phase drug while permitting vapor phase solvent to pass through. In some embodiments the vapor permeable membrane has an average pore size of less than about 10 microns (µm). In some embodiments the vapor permeable membrane has an average pore size of about 0.1 microns to about 10 microns.

The porosity can also be selected to achieve the desired vapor flow characteristics across the vapor permeable membrane. The porosity can be expressed as a ratio of the open surface area of the plurality of pores of the vapor permeable membrane to the surface area of the vapor permeable membrane. In some embodiments the porosity is less than about 50%. In some embodiments the porosity is from about 25% to about 50%. In some embodiments the porosity is from about 25% to about 40%. In some embodiments the porosity is from about 30% to about 40%.

In some embodiments the vapor permeable membrane is made out of PTFE. In some embodiments the vapor permeable membrane can be POREX®. POREX® has an average pore size of 5 microns and a porosity of about 35%.

A variety of different drug delivery system configurations are illustrated in FIGS. 4-14. The systems can include one or more reservoirs, such as reservoir 38 and bolus chamber 46, configured to hold the bioactive agent and/or the solvent composition. The agent reservoir can refer to either of the bolus/dose reservoir and main reservoir.

A dose of the bioactive agent can be provided to the space between the transdermal membrane and the vapor permeable membrane. The system is configured to move the bioactive agent in the solvent solution from the agent reservoir to a virtual space between the vapor permeable membrane and the transdermal membrane. The dose is preferably provided such that the dose quickly and evenly spreads across the transdermal membrane. The transdermal membrane can be treated to improve wettability of the membrane. In some cases the transdermal membrane can be tautly spread to reduce the likelihood of pooling of the dose or poor distribution of the dose across the transdermal membrane. In some embodiments the dose of the bioactive agent and solvent solution is provided to a substantially centrally located section of the membrane. In some embodiments the dose of the bioactive agent and solvent solution is provided to an off-center section of the membrane. In some embodiments the dose of the bioactive agent and solvent solution is provided through multiple orifices onto the membrane.

The distribution of the dose across the membrane can also be improved by providing a specific volume of the dose per surface area of the transdermal membrane. In some embodiments the dose of the bioactive agent and solvent solution has a volume of less than about 250 µL per 10 cm² of surface area of the membrane. In some embodiments the dose of the bioactive agent and solvent solution has a volume of between about 75 µL to about 250 µL per 10 cm² of surface area of the membrane. In some embodiments the dose of the bioactive agent and solvent solution has a volume of less than about 150 µL per 10 cm² of surface area of the membrane.

The systems can include enough bioactive agent for a single dose, a full day's worth of dosing, or enough doses to cover multiple days. The bioactive drug and solvent composition can be provided in a main reservoir and moved to a dosing/bolus chamber prior to drug delivery as described herein.

The volume of the agent reservoir (e.g. reservoir 38) can vary based on the dosage size, number of doses, and concentration of the bioactive agent. The agent reservoir can have a volume of less than about 3 ml. In some embodiments the agent reservoir has a volume of about 5 µL to about 3 ml. In some embodiments the agent reservoir can have a volume of less than about 2 ml. In some embodiments the agent reservoir can have a volume of less than about 1 ml. In some embodiments the agent reservoir has a volume of less than about 750 µL. In some embodiments the agent reservoir has a volume of less than about 500 µL. In some embodiments the agent reservoir has a volume of less than about 250 µL.

A second reservoir (e.g. bolus/bolus chamber) can have a volume of less than 3 ml. In some embodiments the second reservoir has a volume of less than about 1 ml. In some embodiments the second reservoir has a volume of less than about 750 µL. In some embodiments the second reservoir has a volume of less than about 500 µL. In some embodiments the second reservoir has a volume of less than about 250 µL.

The agent reservoir can be provided in a removable and disposable portion. In some embodiments the disposable portion includes both the agent reservoir and the second reservoir (e.g., dosing/bolus chamber). The systems can include a sensor configured to determine when the removable portion is connected to the bioactive agent delivery system.

The systems include a control unit configured to control the bioactive agent delivery system to provide a dose of the bioactive agent and solvent solution from the agent reservoir to the membrane. The control unit can be configured to carry out any of the steps described herein. For example, the control unit can provide a bio-synchronous drug delivery protocol to the wearer of the bioactive agent delivery system.

The control unit can be configured to record a time of administration of the bioactive agent, a dosage amount of the bioactive agent, and a time at which dosing ceased. In some embodiments the system can include a wireless data transfer unit configured to wirelessly transmit the time of administration of the bioactive agent, the dosage amount of the bioactive agent, and the time at which dosing ceased to a remote network or device.

In some embodiments the systems can provide a psychological support to the wearer. The psychological support can be an encouraging messaging or advice about dealing with cravings. The control unit can be configured to gather wearer data during the bio-synchronous drug delivery protocol and to provide the psychological support based on specific patient data. Patient data can include patient emotional state data, such as cravings, and patient compliance. Patient compliance can include determining whether the drug delivery device was removed, a treatment in a drug delivery protocol was missed, or if the drug delivery protocol was interrupted.

The drug delivery systems described herein can include a solvent recovery chamber. The vapor phase solvent solution can be passed in the vapor phase through the vapor permeable membrane into the solvent recovery chamber of the drug delivery device. The movement of the vapor phase solvent from the space between the transdermal membrane and vapor permeable membrane can increase the concentration of the remaining drug or bioactive agent to help promote the drug or bioactive agent permeation across the transdermal membrane.

The solvent recovery chamber can include a desiccant, absorbent material, or external vent. In some embodiments the vapor phase solvent condenses and is collected within the solvent recovery chamber by the desiccant or absorbent material. In some embodiments blotting paper is used as an absorbent material. The solvent recovery chamber can be part of the disposable unit.

Figure 30:
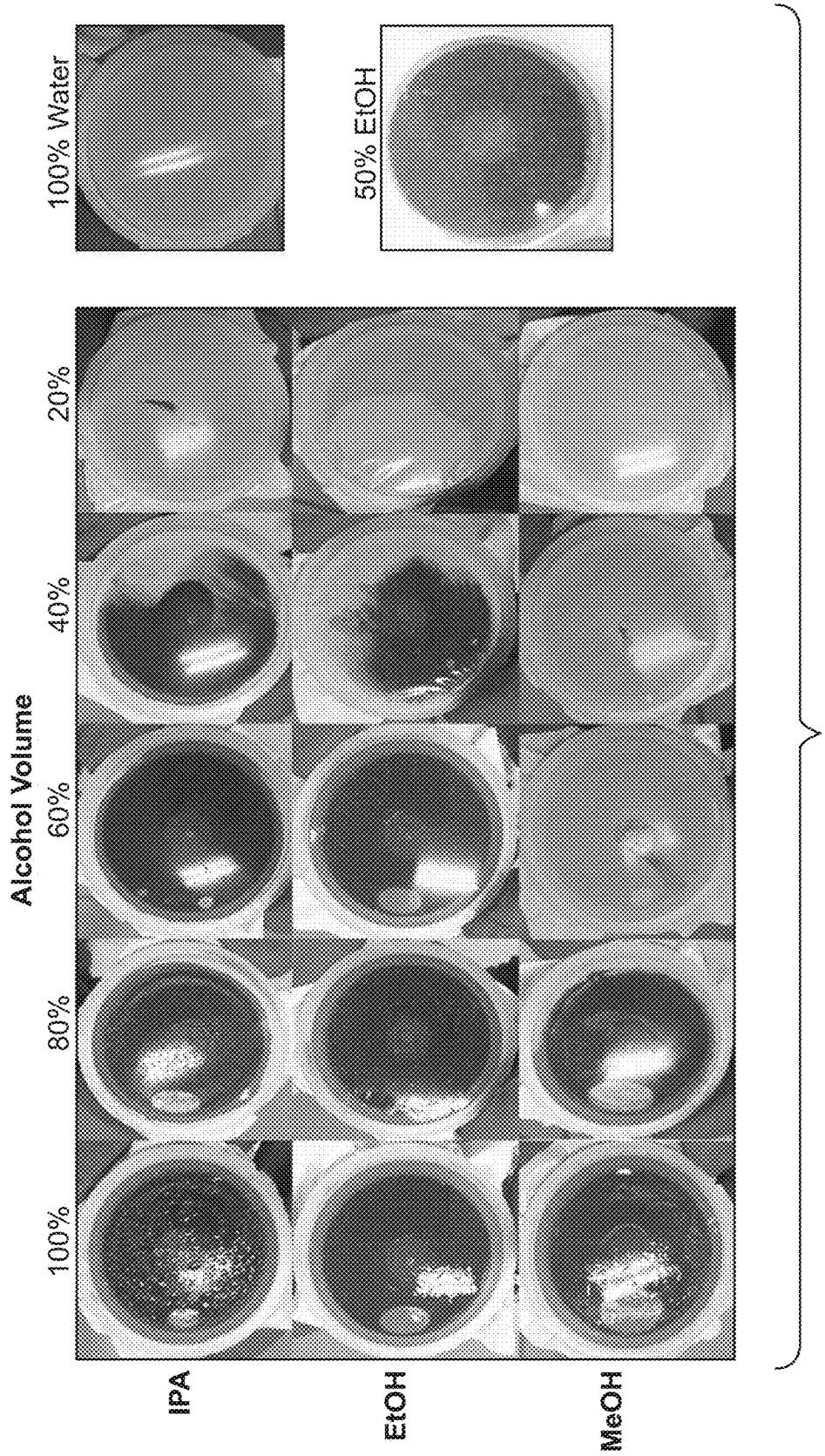
FIG. 30 is a photograph of various solvent and drug compositions interacting with a Celgard® 2400 membrane.
Figure 31:
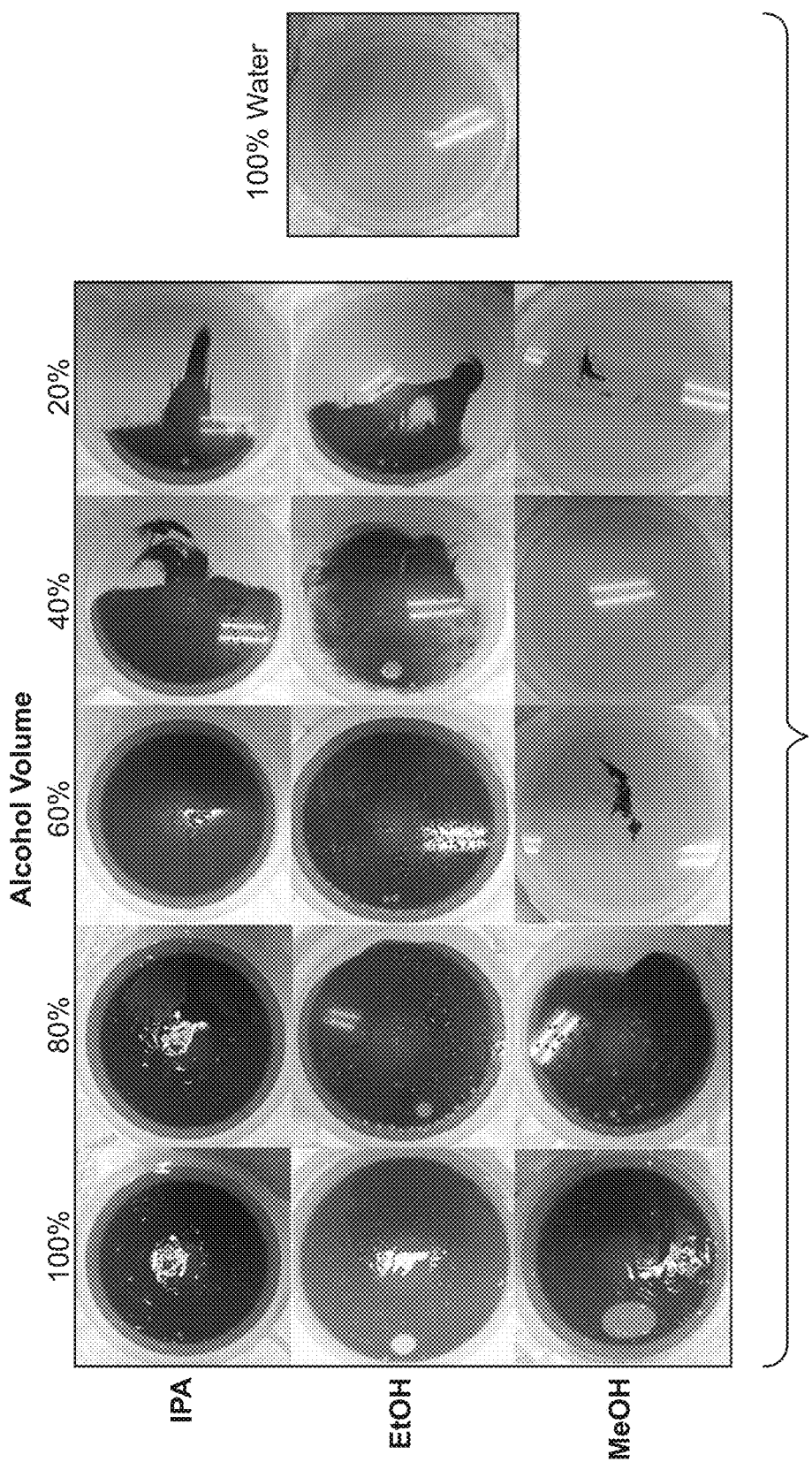
FIG. 31 is a photograph of various solvent and drug compositions interacting with a Celgard® 2500 membrane.
Figure 32:
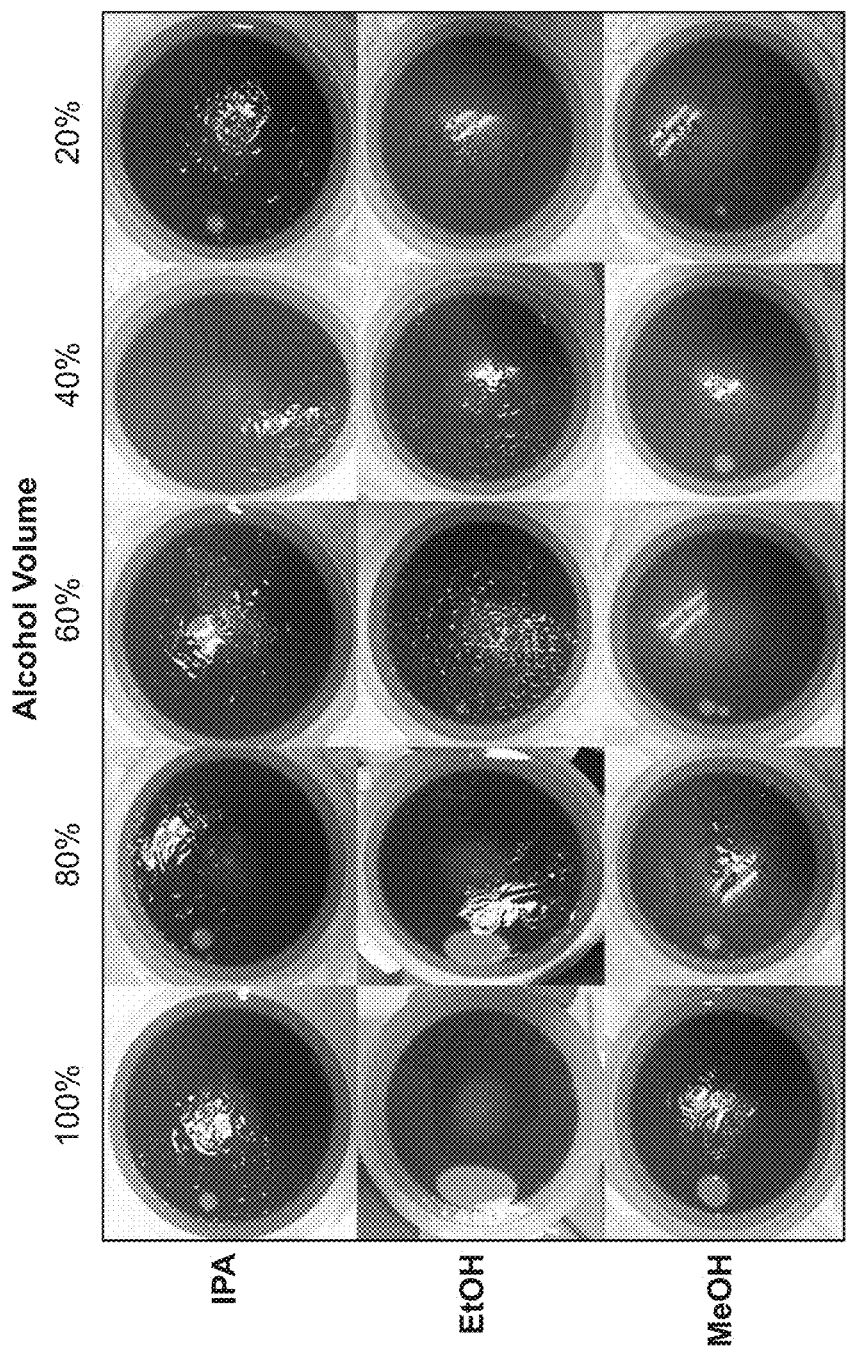
FIG. 32 is a photograph of various solvent and drug compositions interacting with a Celgard® 3501 membrane.

FIGS. 30-32 illustrate different transdermal membrane materials being tested with different solvents and solvent compositions. Solutions of water and different alcohols, including isopropanol, ethanol, and methanol were tested. The water to alcohol content was varied between 0/100 and 100/0 (by v/v) and tested with different membrane materials. For the tests 1.6 mL of solution was injected into the area between the transdermal membrane and the vapor permeable membrane. The transdermal membrane was observed to view the wetting and permeability of the membrane to the tested solvent solution. The membranes were observed approximately 90 seconds after providing the solvent solution to the space between the transdermal membrane and the vapor permeable membrane. A white membrane indicates no permeation of the solvent solution across the membrane. A darkening of the membrane preceded permeation. Three different transdermal membrane materials were tested including Celgard® 2400 (FIG. 30), Celgard® 2500 (FIG. 31), and Celgard® 3501 (FIG. 32). Celgard® 2400 has an average pore diameter of about 0.041 µm and a porosity of 41%. Celgard® 2500 has an average pore diameter of about 0.064 µm and a porosity of 55%. Celgard® 3501 has an average pore diameter of about 0.064 µm and a porosity of 55%.

FIG. 30 shows results for 100% isopropanol, 80% isopropanol/20% water, 60% isopropanol/40% water, 40% isopropanol/60% water, 20% isopropanol/80% water, and 100% water. The 100% water and 20% isopropanol solutions showed white membranes indicative of no permeation. For the isopropanol and water solutions permeation was visible for 40% isopropanol and greater. Liquid visibly passed through the membrane for 80% isopropanol compositions and greater. FIG. 30 also shows results for 100% ethanol (EtOH), 80% ethanol/20% water, 60% ethanol/40% water, 50% ethanol/50% water, 40% ethanol/60% water, and 20% ethanol/80% water. No permeation was observed for 20% ethanol/80% water. Some permeation was observed for 40% ethanol/60% water. 50% ethanol/50% water showed a good balance between permeation and permeation rate. FIG. 30 also shows results for 100% methanol (MeOH), 80% methanol/20% water, 60% methanol/40% water, 40% methanol/60% water, and 20% methanol/80% water. No permeation was observed for 20% methanol, 40% methanol, and 60% methanol compositions. Some permeation was observed for 80% methanol and 100% methanol. For Celgard® 2400, the composition of 50% ethanol and 50% water (v/v) exhibited the best combination of permeation and permeation rate.

FIG. 31 shows results Celgard® 2500 for 100% isopropanol, 80% isopropanol/20% water, 60% isopropanol/40% water, 40% isopropanol/60% water, and 20% isopropanol/80% water. The 20% isopropanol and 40% isopropanol compositions showed minimal permeation. For the isopropanol and water solutions permeation was visible for 60% isopropanol and greater. Liquid visibly passed through the membrane for 80% isopropanol compositions and greater. FIG. 31 also shows results for 100% ethanol (EtOH), 80% ethanol/20% water, 60% ethanol/40% water, 40% ethanol/60% water, and 20% ethanol/80% water. Minimal permeation was observed for 20% ethanol/80% water. Some permeation was observed for 40% ethanol/60% water. FIG. 31 also shows results for 100% methanol (MeOH), 80% methanol/20% water, 60% methanol/40% water, 40% methanol/60% water, and 20% methanol/80% water. No permeation was observed for 20% methanol, 40% methanol, and 60% methanol compositions. Some permeation was observed for 80% methanol and 100% methanol.

FIG. 32 shows results for Celgard® 3501 for 100% isopropanol, 80% isopropanol/20% water, 60% isopropanol/40% water, 40% isopropanol/60% water, and 20% isopropanol/80% water. All of the isopropanol solutions showed permeation of the Celgard® 3501 membrane. FIG. 32 also shows results for 100% ethanol (EtOH), 80% ethanol/20% water, 60% ethanol/40% water, 40% ethanol/60% water, and 20% ethanol/80% water. All ethanol compositions showed permeation for Celgard® 3501. FIG. 32 also shows results for 100% methanol (MeOH), 80% methanol/20% water, 60% methanol/40% water, 40% methanol/60% water, and 20% methanol/80% water. All compositions of methanol showed permeation with Celgard® 3501. The increased permeation with Celgard® 3501 could be due to a combination of the larger pore size and surfactant coating.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed. The term "about" when used with a quantity or measurement means±10%.

What is claimed is:

1. A two-part bioactive agent delivery system, the system comprising:
 a disposable part comprising:
  a bioactive agent reservoir, the bioactive agent reservoir comprising an agent reservoir piston movable relative to the bioactive agent reservoir,
  a bolus chamber, the bolus chamber comprising a bolus piston movable relative to the bolus chamber, the volume of the bolus chamber being less than the volume of the bioactive agent reservoir,
  an agent outlet in fluid communication with a transdermal membrane, and
  a valve having a first position communicating the bioactive agent reservoir with the bolus chamber and a second position communicating the bolus chamber with the agent outlet; and
 a reusable part comprising a valve driver, a power source and control electronics, the control electronics being adapted to control the valve driver to actuate the valve to move to the first position or to the second position to deliver bioactive agent from the bioactive agent reservoir to the agent outlet; and
 an agent reservoir loading component extending between the agent reservoir piston and the reusable part, the loading component configured to apply force to the agent reservoir piston to enable the valve to release a dose of bioactive agent from the bioactive agent reservoir to the bolus chamber when the disposable part is connected to the reusable part.

* * * * *